(12) United States Patent
Anderson et al.

(10) Patent No.: US 8,314,250 B2
(45) Date of Patent: Nov. 20, 2012

(54) SULTAM DERIVATIVES

(75) Inventors: Kevin W. Anderson, Hackettstown, NJ (US); Paul Gillespie, Westfield, NJ (US); Nicholas J. S. Huby, Scotch Plains, NJ (US); Norman Kong, West Caldwell, NJ (US); John L. Roberts, Budd Lake, NJ (US); Pamela L. Rossman, Nutley, NJ (US); Sung-Sau So, Verona, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 119 days.

(21) Appl. No.: 12/905,120

(22) Filed: Oct. 15, 2010

(65) Prior Publication Data
US 2011/0124686 A1 May 26, 2011

Related U.S. Application Data

(60) Provisional application No. 61/263,979, filed on Nov. 24, 2009.

(51) Int. Cl.
*C07D 285/01* (2006.01)
*C07D 417/06* (2006.01)
*A61K 31/425* (2006.01)
*A61K 31/4535* (2006.01)
*A61K 31/4523* (2006.01)

(52) U.S. Cl. ......... 548/214; 546/209; 514/326; 514/372
(58) Field of Classification Search .................. None
See application file for complete search history.

(56) References Cited

U.S. PATENT DOCUMENTS
7,897,629 B2 * 3/2011 Burk et al. ............... 514/372
2007/0155705 A1 * 7/2007 Castro et al. ............. 514/109
2007/0161690 A1 7/2007 Castro et al.

FOREIGN PATENT DOCUMENTS
WO 2006009869 1/2006
WO 2007075387 7/2007

OTHER PUBLICATIONS

Cherney RJ et al: Journal of Medicinal Chemistry (2004) 47:12 2981-2983.
International Search Report for 26079 WO dated Feb. 25, 2011.

* cited by examiner

*Primary Examiner* — Kamal Saeed
*Assistant Examiner* — Nyeemah A Grazier
(74) *Attorney, Agent, or Firm* — George W. Johnston; Patricia S. Rocha-Tramaloni

(57) ABSTRACT

The present invention relates to compounds according to formula 1,

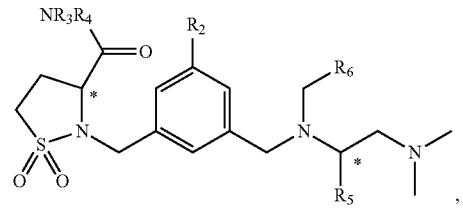

Formula 1 which exhibit cytotoxic activity. The compounds may be used in the treatment of cancer.

37 Claims, No Drawings

SULTAM DERIVATIVES

CROSS-REFERENCE TO RELATED APPLICATIONS

This application is entitled to the benefit of U.S. provisional patent application Ser. No. 61/263,979 filed on Nov. 24, 2009, the disclosure of which is incorporated herein by reference.

FIELD OF THE INVENTION

The present invention relates to compounds according to formula 1,

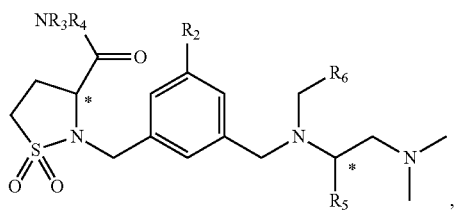

Formula 1 and pharmaceutically-acceptable salts thereof, wherein $R_2$, $R_3$, $R_4$, $R_5$, and $R_6$ are as defined herein.

These compounds have cytotoxic activity. As such, they are useful in the treatment or control of proliferative disorders such as cancer, in particular solid tumors.

This invention is also directed to a composition and a unit dose formulation comprising a compound of the present invention, methods of making such compounds, and methods for using such compounds in the treatment of proliferative disorders, such as cancer, in particular solid tumors, and most particularly breast tumor, lung tumor, colon tumor, and prostate tumor.

BACKGROUND OF THE INVENTION

Many disease states are characterized by uncontrolled proliferation and differentiation of cells. These disease states encompass a variety of cell types and maladies such as cancer, atherosclerosis, and restenosis.

The term cancer is used to describe a class of diseases characterized principally by uncontrolled cell growth. Cancer is currently one of the leading causes of death in the world, and is projected to become the leading cause of death in the next few years. By 2030, it is projected that there will be more than 20 million new cancer diagnoses per annum, with at least 13 million deaths.

There are many different forms of cancer, and many of these types require different forms of treatment. The current main forms of treatment for cancer include surgery, radiation therapy, bone marrow transplantation, immunotherapy, anti-angiogenic therapy, and treatment with cytotoxic agents (commonly known as chemotherapy). A large number of cytotoxic agents have been used for the treatment of cancer over the last 70 years, including nitrogen mustards such as chloromethine and estramustine; anthracyclines such as doxorubicin, daunorubicin, and idarubicin; platinum-containing compounds such as cisplatin, carboplatin and oxaliplatin; antimetabolites such as dacarbazine, capecitabine, fludarabine, 5-fluorouracil, gemcitabine, methotrexate, and pemetrexed; topoisomerase inhibitors such as topotecan and irinotecan; inhibitors of tubulin polymerization such as vinblastine and vincristine; and inhibitors of tubulin depolymerization such as paclitaxel and docetaxel.

Although many cytotoxic agents are known and have achieved considerable success as therapeutic agents for the treatment of a variety of cancers, there is still a significant unmet need for new therapies, and a need for new cytotoxic agents.

SUMMARY OF THE INVENTION

The present invention relates to compounds according to formula 1,

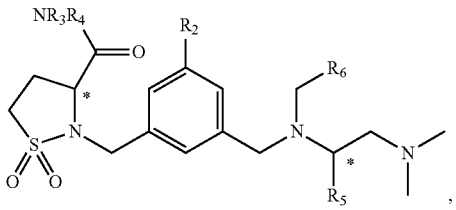

Formula 1 and pharmaceutically-acceptable salts thereof, wherein $R_2$, $R_3$, $R_4$, $R_5$, and $R_6$ are as defined herein.

These compounds have cytotoxic activity. As such, they are useful in the treatment or control of proliferative disorders such as cancer, in particular solid tumors.

DETAILED DESCRIPTION OF THE INVENTION

The term "alkenyl", as used herein, refers to a straight- or branched-chain hydrocarbon group having at least one double bond and from 2 to 6, preferably 2 to 4, carbon atoms. Examples of "alkenyl groups" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The terms "alkoxy" and "alkoxyl", as used herein, each refer to a group in which an alkyl (as defined below) is attached to an oxygen atom. The term "lower alkoxy" refers to a group in which a lower alkyl (as defined below) is attached to an oxygen atom. Typical lower alkoxy groups include methoxy, ethoxy, isopropoxy or propoxy, butyloxy and the like.

The term "alkyl", as used herein, refers to a straight- or branched-chain saturated hydrocarbon group having from 1 to about 20 carbon atoms, and, in certain embodiments, from 1 to about 7 carbon atoms. The term "lower alkyl" refers to an alkyl group having from 1 to 6 carbon atoms, and, in certain embodiments, from 1 to 4 carbon atoms. Examples of alkyl groups include, but are not limited to, methyl, ethyl, n-propyl, i-propyl, n-butyl, s-butyl, t-butyl, n-pentyl, 2,2-dimethylpentyl, and s-pentyl.

The term "alkynyl", as used herein, refers to a straight- or branched-chain hydrocarbon group having at least one triple bond and from 2 to 6, preferably 2 to 4, carbon atoms. Examples of "alkynyl groups" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "aryl", as used herein, refers to a monocyclic or bicyclic aromatic hydrocarbon group, preferably containing 6 to 10 ring carbon atoms. Preferred aryl groups include, but are not limited to, phenyl, naphthyl, tolyl, and xylyl.

The term "azole", as used herein, refers to a 5-membered heteroaryl (defined below) wherein at least one of the heteroatoms (defined below) is nitrogen. An "oxadiazole" is an azole having three heteroatoms with two being nitrogen and one being oxygen. A "triazole" is an azole having three heteroatoms with all three being nitrogen. A "tetrazole" is an azole having four heteroatoms with all four being nitrogen.

The term "carrier", as used herein, refers to a pharmaceutically inert vehicle (e.g., a solvent, suspending agent) useful in delivering an active compound, for example, a compound of the present invention, to a patient.

The term "cycloalkenyl", as used herein, refers to a stable monocyclic or polycyclic, non-aromatic, hydrocarbon group which is unsaturated and which contains 5 to 10 ring atoms. Examples of cycloalkenyls include, but are not limited to, cyclopentenyl or cyclohexenyl.

The term "cycloalkyl", as used herein, refers to a stable monocyclic or polycyclic, non-aromatic, saturated, hydrocarbon group containing 3 to 10 ring atoms. Examples of cycloalkyls include, but are not limited to, cyclopropyl, cyclobutyl, cyclopentyl, cyclohexyl, cycloheptyl, adamantyl, cyclooctyl, bicycloalkyls, including bicycloheptyls such as bicyclo[3.1.1]heptyl and bicyclo[2.2.1]heptyl.

The term "excipient", as used herein, refers to a pharmaceutically-inert substance.

The term "halogen", as used herein, refers to fluorine, chlorine, bromine, or iodine, preferably fluorine and chlorine.

The term "heteroaryl", as used herein, refers to an aromatic mono- or bicyclic group which contains at least one heteroatom. The term "heteroatom", as used herein, refers to a ring atom that is nitrogen, oxygen, or sulfur. Preferred heteroaryl groups include, but are not limited to, thienyl, furyl, indolyl, pyrrolyl, pyridinyl, pyrazinyl, oxazolyl, oxadiazolyl, thiazolyl, quinolinyl, pyrimidinyl, imidazoyl, triazolyl, and tetrazolyl. In the case of a bicyclic heteroaryl group, it should be understood that the ring atoms of one ring may all be carbon while the other ring may contain a heteroatom.

The term "heterocycle", as used herein, refers to 4- to 8-membered mono- or bicyclic, saturated or partially unsaturated, non-aromatic group which contains 1 to 3 heteroatoms. Examples of heterocycles include pyrrolidin-2-yl; pyrrolidin-3-yl; piperidinyl; morpholin-4-yl and the like. In the case of a bicyclic heterocycle, it should be understood that the ring atoms of one ring may all be carbon while the other ring may contain a heteroatom.

The term "$IC_{50}$", as used herein, refers to the concentration of a particular compound required to inhibit 50% of a specific measured activity. $IC_{50}$ can be measured, inter alia, as described subsequently.

The term "$IC_{90}$", as used herein, refers to the concentration of a particular compound required to inhibit 90% of a specific measured activity. $IC_{90}$ can be measured, inter alia, as described subsequently.

As used herein, a compound is said to exhibit "cytotoxic activity" if the percentage of inhibition, as measured using the assay of Example 36, is at least about 50%. In a preferred embodiment, the percentage of inhibition as measured using such an assay is at least about 75% and even more preferably at least about 95%.

The term "pharmaceutically-acceptable", as used herein in reference to a compound (e.g., a carrier, a salt, an ester, etc.), means that the compound is pharmacologically acceptable and substantially non-toxic to the subject to which the particular compound is administered.

With the context of the aforementioned definition of "pharmaceutically-acceptable", a "pharmaceutically-acceptable salt" of a compound is a conventional acid-addition salt or a base-addition salt that retains the biological effectiveness and properties of the compound and that is formed from a suitable non-toxic organic or inorganic acid or base. Sample acid-addition salts include those derived from inorganic acids such as hydrochloric acid, hydrobromic acid, hydriodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, lithium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) pgs. 456-457.

With the context of the aforementioned definition of "pharmaceutically-acceptable", a "pharmaceutically-acceptable ester" of a compound is a conventional ester of the compound which contains a hydroxyl or carboxyl group; the ester retains the biological effectiveness and properties of the compound and is capable of being cleaved in vivo (in the organism) to the corresponding active alcohol or carboxylic acid respectively.

The term "substituted", as used herein to describe any of the above chemical groups (e.g., substituted alkyl, substituted aryl, substituted heteroaryl), refers to a chemical group in which 1 to 5 hydrogen atoms, preferably 1 to 3, have been independently replaced with a substituent.

The term "unit dose formulation", as used herein, refers to a pharmaceutical preparation (e.g., tablet, capsule) comprising an active agent, for example, a compound of the present invention, in stable form and capable of being administered to a patient as a single dose.

The present invention relates to a compound according to formula 1,

Formula 1

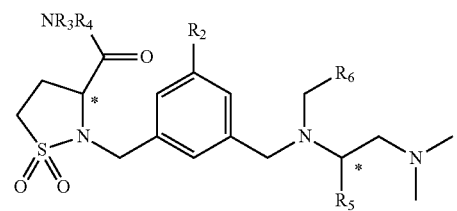

and pharmaceutically-acceptable salts of such a compound, wherein the compound exhibits cytotoxic activity and:
$R_2$ is hydrogen or dimethylamino;
$R_3$ is hydrogen;
$R_4$ is cycloalkyl optionally substituted with alkyl, or
benzyl optionally substituted with halogen;
or $R_3$ and $R_4$, together with the nitrogen atom to which they are attached, form piperidinyl substituted with one or more substituents independently selected from the group consisting of: hydroxyl and phenyl optionally substituted with halogen;

$R_5$ is 2,2-dimethylpropyl or benzyl optionally substituted with halogen; and $R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

In an embodiment of the present invention, the compound is a compound of formula 1 that exhibits cytotoxic activity, or a pharmaceutically-acceptable salt thereof, wherein $R_2$ is hydrogen.

In another embodiment of the present invention, the compound is a compound of formula 1 that exhibits cytotoxic activity, or a pharmaceutically-acceptable salt thereof, wherein $R_2$ is dimethylamino.

In another embodiment of the present invention, the compound is a compound of formula 1 that exhibits cytotoxic activity, or a pharmaceutically-acceptable salt thereof, wherein $R_4$ is cycloalkyl optionally substituted with alkyl.

In another embodiment of the present invention, the compound is a compound of formula 1 that exhibits cytotoxic activity, or a pharmaceutically-acceptable salt thereof, wherein $R_4$ is benzyl optionally substituted with halogen.

In another embodiment of the present invention, the compound is a compound of formula 1 that exhibits cytotoxic activity, or a pharmaceutically-acceptable salt thereof, wherein $R_3$ and $R_4$, together with the nitrogen atom to which they are attached, form piperidinyl substituted with one or more substituents independently selected from the group consisting of: hydroxyl and phenyl optionally substituted with halogen.

In another embodiment of the present invention, the compound is a compound of formula 1 that exhibits cytotoxic activity, or a pharmaceutically-acceptable salt thereof, wherein $R_5$ is 2,2-dimethylpropyl.

In another embodiment of the present invention, the compound is a compound of formula 1 that exhibits cytotoxic activity, or a pharmaceutically-acceptable salt thereof, wherein $R_5$ is benzyl optionally substituted with halogen.

In another embodiment of the present invention, the compound is a compound of formula 1 that exhibits cytotoxic activity, or a pharmaceutically-acceptable salt thereof, wherein $R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

In another embodiment of the present invention, the compound is a compound of formula 1 that exhibits cytotoxic activity, or a pharmaceutically-acceptable salt thereof, wherein $R_4$ is bicycloheptyl substituted three times with methyl.

In another embodiment of the present invention, the compound is a compound of formula 1 that exhibits cytotoxic activity, or a pharmaceutically-acceptable salt thereof, wherein $R_4$ is adamantanyl.

In another embodiment of the present invention, the compound is a compound of formula 1 that exhibits cytotoxic activity, or a pharmaceutically-acceptable salt thereof, wherein $R_4$ is bicyclo[3.1.1]hept-3-yl.

In another embodiment of the present invention, the compound is a compound of formula 1 that exhibits cytotoxic activity, or a pharmaceutically-acceptable salt thereof, wherein:

$R_2$ is hydrogen;
$R_3$ is hydrogen;
$R_4$ is 2,6,6-trimethyl-bicyclo[3.1.1]hept-3-yl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

Examples of such compounds include:

2-(3-{[(5-Chloro-2-hydroxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide;

2-(3-{[((S)-1-Dimethylaminomethyl-3,3-dimethyl-butyl)-(2-iodo-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-ethoxy-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(5-isopropyl-2-methoxy-benzyl)-amino]-methyl}-benzyl)-1,1-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(2-Difluoromethoxy-benzyl)-((S)-1-dimethylaminomethyl-3,3-dimethyl-butyl)amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-[3-({((S)-1-Dimethylaminomethyl-3,3-dimethyl-butyl)-[2-(4-fluoro-phenoxy)-benzyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-p-tolyloxy-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(4'-fluoro-biphenyl-2 ylmethyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-hydroxy-4-methylbenzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-hydroxy-5-methyl-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2'-methyl-biphenyl-2ylmethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-fluoro-6-phenoxy-benzyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2,3,6-trifluoro-benzyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt;

2-(3-{[(6-Bromo-2-hydroxy-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt;

2-(3-{[(6-Chloro-2-fluoro-3-methyl-benzyl)-((S)-1-dimethylaminomethyl-3,3-dimethyl butyl)-amino]-methyl}-benzyl)-1,1-dioxo-1λ⁶-isothiazolidine-3-carboxylic acid ((1S,2S,3S,5R)-2,6,6-trimethyl-bicyclo[3.1.1]hept-3-yl)-amide trifluoroacetate salt;

2-(3-{[[2-(4-Cyano-phenoxy)-benzyl]-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt;

2-(3-{[(3-Bromo-2,6-difluoro-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt;

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid ((1R,2R,3R,5S)-2,6,6-trimethyl-bicyclo[3.1.1]hept-3-yl)-amide; and 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid ((1S,2S,3S,5R)-2,6,6-trimethyl-bicyclo[3.1.1]hept-3-yl)-amide.

In another embodiment of the present invention, the compound is a compound of formula 1 that exhibits cytotoxic activity, or a pharmaceutically-acceptable salt thereof, wherein
R₂ is hydrogen;
R₃ is hydrogen;
R₄ is adamantanyl;
R₅ is 2,2-dimethylpropyl; and
R₆ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

Examples of such compounds include:
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid adamantan-1-ylamide;

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid adamantan-2-ylamide; and 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid adamantan-1-ylamide.

In another embodiment of the present invention, the compound is a compound of formula 1 that exhibits cytotoxic activity, or a pharmaceutically-acceptable salt thereof, wherein:
R₂ is hydrogen;
R₃ is hydrogen;
R₄ is 2,6,6-trimethyl-bicyclo[3.1.1]hept-3-yl;
R₅ is 2,2-dimethylpropyl; and
R₆ is benzodioxolyl.

An example of such a compound is 2-(3-{[Benzo[1,3]dioxol-4-ylmethyl-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt.

In another embodiment of the present invention, the compound is a compound of formula 1 that exhibits cytotoxic activity, or a pharmaceutically-acceptable salt thereof, wherein:
R₂ is hydrogen;
R₃ is hydrogen;
R₄ is 2,6,6-trimethyl-bicyclo[3.1.1]hept-3-yl;
R₅ is benzyl optionally substituted with halogen; and
R₆ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

Examples of such compounds include:
2-(3-{[(6-Chloro-2-fluoro-3-methoxy-benzyl)-((S)-1-dimethylaminomethyl-2-phenyl-ethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide;

2-[3-({(6-Chloro-2-fluoro-3-methoxy-benzyl)-[(S)-2-(3-chloro-phenyl)-1-dimethylaminomethyl-ethyl]-amino}-methyl)-benzyl]-1,1-dioxo-1λ⁶-isothiazolidine-3-carboxylic acid((1S,2S,3S,5R)-2,6,6-trimethyl-bicyclo[3.1.1]hept-3-yl)-amide;

2-[3-({(6-Chloro-2-fluoro-3-methoxy-benzyl)-[(S)-2-(4-chloro-phenyl)-1-dimethylaminomethyl-ethyl]-amino}-methyl)-benzyl]-1,1-dioxo-1λ⁶-isothiazolidine-3-carboxylic acid((1S,2S,3S,5R)-2,6,6-trimethyl-bicyclo[3.1.1]hept-3-yl)-amide; and 2-(3-{[(2,3-Difluoro-6-methoxy-benzyl)-((S)-1-dimethylaminomethyl-2-phenyl-ethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide.

In another embodiment of the present invention, the compound is a compound of formula 1 that exhibits cytotoxic activity, or a pharmaceutically-acceptable salt thereof, wherein
R₂ is hydrogen;
R₃ and R₄, together with the nitrogen atom to which they are attached, form piperidinyl substituted with one or more substituents independently selected from the group consisting of: hydroxyl and phenyl optionally substituted with halogen;
R₅ is 2,2-dimethylpropyl; and $R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

Examples of such compounds include:
[2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-(4-phenyl-piperidin-1-yl)-methanone; and
[2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-[4-(4-chlorophenyl)-4-hydroxy-piperidin-1-yl]-methanone.

In another embodiment of the present invention, the compound is a compound of formula 1 that exhibits cytotoxic activity, or a pharmaceutically-acceptable salt thereof, wherein
$R_2$ is hydrogen;
$R_3$ is hydrogen;
$R_4$ is benzyl optionally substituted with halogen;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

An example of such a compound is 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid 4-chloro-benzylamide.

In another embodiment of the present invention, the compound is a compound of formula 1 that exhibits cytotoxic activity, or a pharmaceutically-acceptable salt thereof, wherein
$R_2$ is hydrogen;
$R_3$ is hydrogen;
$R_4$ is bicyclo[2.2.1]hept-3-yl optionally substituted with lower alkyl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and aryl optionally substituted with alkyl or halogen.

Examples of such compounds include:
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((S)-1,7,7-trimethyl-bicyclo[2.2.1]hept-2-yl)-amide;
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1R,2R,3R,4S)-3-isopropyl-bicyclo[2.2.1]hept-2-yl)-amide; and
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,4R)-3-isopropyl-bicyclo[2.2.1]hept-2-yl)-amide;

In another embodiment of the present invention, the compound is a compound of formula 1 that exhibits cytotoxic activity, or a pharmaceutically-acceptable salt thereof, wherein:
$R_2$ is dimethylamino;
$R_3$ is hydrogen;
$R_4$ is 2,6,6-trimethyl-bicyclo[3.1.1]hept-3-yl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

An example of such a compound is 2-(3-{[(6-Chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide hydrochloride salt.

In another embodiment of the present invention, the compound is a compound of formula 1 that exhibits cytotoxic activity, or a pharmaceutically-acceptable salt thereof, wherein:
$R_2$ is hydrogen or dimethylamino;
$R_3$ is hydrogen;
$R_4$ is a bicyclic or tricyclic cycloalkyl with 7 to 10 ring atoms which optionally substituted with lower alkyl or 4-chlorobenzyl;
or $R_3$ and $R_4$, together with the nitrogen atom to which they are attached, form 4-phenyl-piperidine or 4-(4-chloro-phenyl)-4-hydroxy-piperidine;
$R_5$ is selected from the group consisting of: 2,2-dimethylpropyl; benzyl; 3-chlorobenzyl; and 4-chlorobenzyl;
$R_6$ is

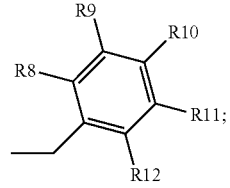

$R_8$ is selected from the group consisting of: bromo; cyanophenoxy; difluoromethoxy; ethoxy; fluoro; hydroxyl; iodo; methoxy; phenyl optionally substituted by one substituent which is halogen or lower alkyl; and phenoxy optionally substituted by one substituent which is selected from the group consisting of halogen, cyano, and lower alkyl;
$R_9$ is selected from the group consisting of hydrogen; methoxy; methyl; fluoro; and bromo;
or $R_8$ and $R_9$, taken together are —O—CH$_2$—O—;
$R_{10}$ is hydrogen or methyl;
$R_{11}$ is selected from the group consisting of: chloro; fluoro; hydrogen; isopropyl; and methyl; and
$R_{12}$ is selected from the group consisting of: chloro; fluoro; hydrogen; hydroxyl; methoxy; and phenoxy.

In another embodiment of the present invention, the compound is a compound of formula 1 that exhibits cytotoxic activity, or a pharmaceutically-acceptable salt thereof, wherein:
$R_2$ is hydrogen;
$R_3$ is hydrogen;
$R_4$ is a bicyclic or tricyclic cycloalkyl with 7 to 10 ring atoms which optionally substituted with lower alkyl or 4-chlorobenzyl;

or $R_3$ and $R_4$, together with the nitrogen atom to which they are attached, form 4-phenyl-piperidine or 4-(4-chloro-phenyl)-4-hydroxy-piperidine;
$R_5$ is selected from the group consisting of: 2,2-dimethylpropyl; benzyl; 3-chlorobenzyl; and 4-chlorobenzyl;
$R_6$ is

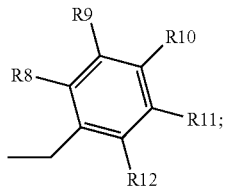

$R_8$ is selected from the group consisting of: bromo; cyanophenoxy; difluoromethoxy; ethoxy; fluoro; hydroxyl; iodo; methoxy; phenyl optionally substituted by one substituent which is halogen or lower alkyl; and phenoxy optionally substituted by one substituent which is selected from the group consisting of halogen, cyano, and lower alkyl;
$R_9$ is selected from the group consisting of hydrogen; methoxy; and bromo;
or $R_8$ and $R_9$, taken together are —O—CH$_2$—O—;
$R_{10}$ is hydrogen or methyl;
$R_{11}$ is selected from the group consisting of: chloro; fluoro; hydrogen; isopropyl; and methyl; and
$R_{12}$ is selected from the group consisting of: chloro; fluoro; hydrogen; and hydroxyl.

In another embodiment of the present invention, the compound is a compound of formula 1 that exhibits cytotoxic activity, or a pharmaceutically-acceptable salt thereof, wherein:
$R_2$ is hydrogen or dimethylamino;
$R_3$ is hydrogen;
$R_4$ is a bicyclic or tricyclic cycloalkyl with 7 to 10 ring atoms which optionally substituted with lower alkyl or 4-chlorobenzyl;
or $R_3$ and $R_4$, together with the nitrogen atom to which they are attached, form 4-phenyl-piperidine or 4-(4-chloro-phenyl)-4-hydroxy-piperidine;
$R_5$ is selected from the group consisting of: 2,2-dimethylpropyl; benzyl; 3-chlorobenzyl; and 4-chlorobenzyl;
$R_6$ is

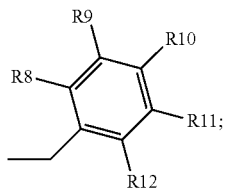

$R_8$ is selected from the group consisting of: bromo; difluoromethoxy; ethoxy; fluoro; iodo; phenyl substituted by one substituent which is halogen or lower alkyl; and phenoxy optionally substituted by one substituent which is selected from the group consisting of halogen, cyano, and lower alkyl;
$R_9$ is selected from the group consisting of hydrogen; methoxy; methyl; methylenedioxy; fluoro; and bromo;
or $R_8$ and $R_9$, taken together are —O—CH$_2$—O—;
$R_{10}$ is hydrogen;
$R_{11}$ is hydrogen; and $R_{12}$ is selected from the group consisting of: chloro; fluoro; hydrogen; hydroxyl; methoxy; and phenoxy.

In another embodiment of the present invention, the compound is a compound of formula 1 that exhibits cytotoxic activity, or a pharmaceutically-acceptable salt thereof, wherein
$R_2$ is hydrogen or dimethylamino;
$R_3$ is hydrogen;
$R_4$ is a bicyclic or tricyclic cycloalkyl with 7 to 10 ring atoms which optionally substituted with lower alkyl or 4-chlorobenzyl;
or $R_3$ and $R_4$, together with the nitrogen atom to which they are attached, form 4-phenyl-piperidine or 4-(4-chloro-phenyl)-4-hydroxy-piperidine;
$R_5$ is selected from the group consisting of: 2,2-dimethylpropyl; benzyl; 3-chlorobenzyl; and 4-chlorobenzyl; and
$R_6$ is selected from the group consisting of:
2-bromo-6-hydroxy-3-methoxyphenyl;
6-chloro-2-fluoro-3-methoxyphenyl;
6-chloro-2-fluoro-3-methylphenyl;
5-chloro-2-hydroxyphenyl;
2-(4-cyanophenoxy)-phenyl;
2,6-difluoro-3-bromophenyl;
2,3-difluoro-6-methoxyphenyl;
2-difluoromethoxyphenyl;
2-ethoxyphenyl;
4'-fluoro-biphenyl-2-yl;
2-fluoro-6-phenoxyphenyl;
2-(4-fluorophenoxy)-phenyl;
2-hydroxy-4-methylphenyl;
2-hydroxy-5-methylphenyl;
2-iodophenyl;
5-isopropyl-2-methoxyphenyl;
2'-methyl-biphenyl-2-yl;
2,3-methylenedioxyphenyl;
2-(4-methylphenoxy)-phenyl; and
2,3,6-trifluorophenyl.

The compounds of the present invention have cytotoxic activity. As such, they may be useful in the treatment or control of a cell proliferative disorder, such as cancer, in particular solid tumors, and most particularly breast tumor, lung tumor, colon tumor, and prostate tumor.

The compound of the present invention may exist as a racemic mixture, mixtures of diastereoisomers, a scalemic mixture, or as an isolated stereoisomer. The stereoisomer may be isolated by known separation methods, for example, by chromatography.

The compound of the present invention may exhibit tautomerism or structural isomerism. It is intended that the invention encompasses any tautomeric or structural isomeric form of the compound of the present invention, or mixtures of such forms, and is not limited to any one tautomeric or structural isomeric form depicted in the above formulas.

The present invention also relates to a composition comprising a therapeutically-effective amount of a compound according to formula 1 that exhibits cytotoxic activity, or a pharmaceutically-acceptable salt thereof, and a carrier.

The present invention also relates to a unit dose formulation comprising a therapeutically-effective amount of a compound according to formula 1 that exhibits cytotoxic activity, or a pharmaceutically-acceptable salt thereof, and a carrier.

A therapeutically-effective amount of a compound of the present invention is an amount of the compound that is effective to prevent, alleviate or ameliorate symptoms of disease or prolong the survival of the subject being treated. The therapeutically-effective amount or dosage can vary within wide limits and may be determined in a manner known in the art.

Such dosage will be adjusted to the individual requirements in each particular case including the specific compound(s) being administered, the route of administration, the condition being treated, as well as the patient being treated. In general, in the case of oral or parenteral administration of the compound of the present invention to adult humans weighing approximately 70 kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or, for parenteral administration, it may be given as a continuous infusion.

The present invention relates also to a process for the preparation of the compound of the present invention. The compounds of the present invention can be prepared by any conventional means. Suitable processes for synthesizing these compounds are provided in the Examples.

Preferably, the compounds of formula 1 can be prepared from the compounds of the formula 2, formula 5 and formula 9 by following Scheme 1: wherein $R_2$, $R_3$, $R_4$ and $R_5$, $R_6$ are as defined above and $R_1$ is alkyl.

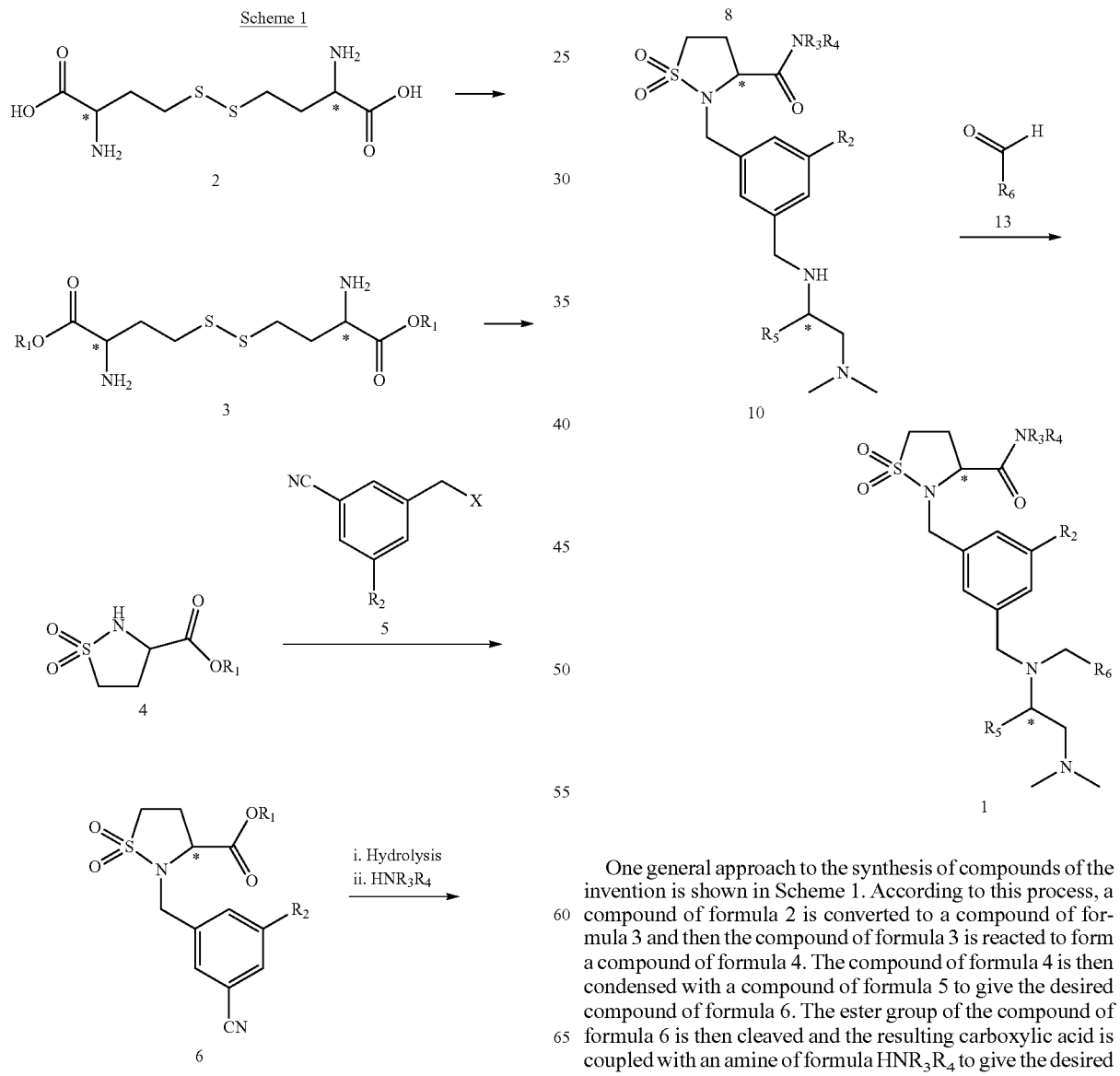

One general approach to the synthesis of compounds of the invention is shown in Scheme 1. According to this process, a compound of formula 2 is converted to a compound of formula 3 and then the compound of formula 3 is reacted to form a compound of formula 4. The compound of formula 4 is then condensed with a compound of formula 5 to give the desired compound of formula 6. The ester group of the compound of formula 6 is then cleaved and the resulting carboxylic acid is coupled with an amine of formula $HNR_3R_4$ to give the desired compound of formula 7. The compound of formula 7 is then converted to a compound of formula 8, which is condensed with a compound of formula 9 to provide a compound of formula 10. The compound of formula 10 is converted to the desired compound of formula 1.

Compounds of formula 2 are commercially available. The racemic acid, DL-homocystine, is available for example from Sigma-Aldrich, St. Louis, Mo., USA. The homochiral materials L-homocystine and D-homocystine are also available from Sigma.

The reaction of a compound of the formula 2 to give a compound of the formula 3 can be carried out using a variety of conditions that are well known in the art, for example, by treating a compound of formula 2 with thionyl chloride in an alcoholic solvent such as, for example, methyl alcohol or ethyl alcohol at a temperature between 0° C. and 25° C. to give the corresponding ester where the $R_1$ group depends on the alcohol used to carry out the reaction. For example, when the reaction is carried out in ethyl alcohol, the resulting compound is a compound of formula 3 where $R_1$ represents ethyl. Examples of conditions for this reaction can be found in the literature, for example, in A. Kelleman et al., *Biopolymers* 2003, 71, 686-695, in O. Busnel et al. *Bioorg. Med. Chem.* 2005, 13, 2373-2379.

The reaction of compound of the formula 3 to give a compound of the formula 4 can be carried out using a variety of conditions that are well known to the art, for example, by treating a compound of formula 3 with an oxidant (for example, chlorine) in water or an alcoholic solvent (for example, methanol) followed by treatment with a tertiary alkyl amine (for example, triethylamine) at a temperature of −5° C. to 25° C. Examples of conditions for this reaction can be found in the literature, for example, in G. Luisi et al. *Archiv der Pharmazie* 1993, 326, 139-141; in R. J. Cherney et al. *J. Med. Chem.* 2004, 47, 2981-2983; and in Z. Chen et al. *Bioorg. Med. Chem. Lett.* 2001, 11, 2111-2115.

The reaction of the compound of formula 4 with a compound of formula 5 (availability and preparation thereof discussed hereinafter), where X is a suitable leaving group such as a halide (for example, bromine, chlorine, iodine), alkyl or aryl sulfonate ester (for example, methane sulfonate or toluene sulfonate), to provide a compound of formula 6 can be carried out using a variety of conditions that are well known to one of ordinary skill in the art. For example, the compound of formula 4 can be reacted with a compound of formula 5 in the presence of an appropriate base, such as a metal carbonate (for example, potassium carbonate, cesium carbonate, sodium carbonate or lithium carbonate, preferably potassium carbonate) or a metal hydride (for example, sodium hydride or potassium hydride) in a suitable solvent such as N,N-dimethylformamide and/or tetrahydrofuran. The reaction can be carried out between about 0° C. and room temperature, preferably at room temperature. As another example, the compound of formula 4 may be reacted with a compound of formula 5, where X is a hydroxyl group, in the presence of a trisubstituted phosphine, such as triphenylphosphine or polymer-bound triphenylphosphine, a coupling agent such as 1,2-diazenedicarboxylic acid, 1,2-diethyl ester in an inert solvent, such as tetrahydrofuran, at a temperature between 0° C. and about room temperature, preferably at room temperature. Examples of conditions for this reaction can be found in the literature, for example, in R. J. Cherney et al. *Bioorg. Med. Chem. Lett.* 2006, 16, 1028-1031; and R. J. Cherney et al. *J. Med. Chem.* 2004, 47, 2981-2983.

The hydrolysis of a compound of formula 6 where R1 represents lower alkyl to the corresponding carboxylic acid is of formula 6 where R1 represents hydrogen may be carried out using conditions that are well known in the field of organic synthesis, many of which are outlined in "Protective Groups in Organic Synthesis" [T. W. Greene and P. G. M. Wuts, $2^{nd}$ Edition, John Wiley & Sons, N.Y. 1991]. For example, in the case where $R_1$ represents methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about room temperature, preferably at about room temperature. As another example, in the case where $R_1$ represents a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of a inert organic solvent (such as dichloromethane) and at a temperature between about 0° C. and about room temperature, preferably at room temperature. As a final (but not limiting) example, in the case where $R_1$ represents a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

The coupling of a carboxylic acid derived from the compound of formula 6 where $R_1$ represents hydrogen with an amine of structure $HNR_3R_4$ (availability and preparation thereof discussed hereinafter), according to Scheme 1, can be achieved using methods well known to one of ordinary skill in the art. For example, the transformation can be carried out by reaction of a carboxylic acid of formula 6 where $R_1$ represents hydrogen or of an appropriate derivative thereof such as an activated ester, with an amine of structure $HNR_3R_4$ or a corresponding acid addition salt (e.g., the hydrochloride salt) in the presence, if necessary, of a coupling agent (many examples are well known in peptide chemistry). The reaction is conveniently carried out by treating the carboxylic acid of structure 6 where $R_1$ represents hydrogen with the hydrochloride of the amine of structure $HNR_3R_4$ in the presence of the appropriate base, such as diisopropylethylamine, a coupling agent such as O-(benzotriazol-1-yl)-1,1,3,3-tetramethyluronium hexafluorophosphate or TSTU and in the optional additional presence of a substance that increases the rate of the reaction, such as 1-hydroxybenzotriazole or 1-hydroxy-7-azabenzotriazole, in an inert solvent, such as chlorinated hydrocarbon (e.g., dichloromethane) or N,N-dimethylformamide or N-methylpyrrolidinone, at a temperature between about 0° C. and about room temperature, preferably at room temperature. Alternatively, the reaction can be carried out by converting the carboxylic acid of formula 6 where $R_1$ represents hydrogen to an activated ester derivative, such as the N-hydroxysuccinimide ester, and subsequently reacting this with the amine of structure $HNR_3R_4$ or a corresponding acid addition salt. This reaction sequence can be carried out by reacting the carboxylic acid of formula 6 where $R_1$ represents hydrogen with N-hydroxysuccinimide or 1-hydroxybenzotriazole in the presence of a coupling agent such as N,N'-dicyclohexylcarbodiimide or 1-ethyl-3-(3'-dimethylaminopropyl)carbodiimide in an inert solvent such as tetrahydrofuran or dichloromethane at a temperature between about 0° C. and room temperature. The resulting N-hydroxysuccinimide ester or 1-hydroxybenzotriazole ester is then treated with the amine of structure $HNR_3R_4$ or a corresponding acid addition salt, in the presence of a base, such as an organic base (e.g., triethylamine or diisopropylethylamine or the like) in a suitable solvent such as N,N-dimethylformamide at around room temperature.

Conversion of the nitrile of formula 7 to the aldehyde of formula 8 can be carried out using any conventional means. For example the nitrile may be subjected to hydrogenation in the presence of Raney nickel in an inert solvent such as aqueous formic acid at about 100° C. Examples of precise conditions suitable for carrying out such a reaction can be found in the literature, for example in A. Tanaka et al. *J. Med. Chem.* 1998, 41, 2390-2410; or in R. J. Sundberg et al. *J. Heterocyclic Chem.* 1988, 25, 129-137. Alternatively, the nitrile may be treated with diisobutylaluminum hydride in an inert solvent such as toluene or a mixture of dichloromethane and hexane at a temperature between about −5° C. and about 0° C. Examples of precise conditions suitable for carrying out such a reaction can be found in the literature, for example in E. Fischer WO 2007147547; in T. Komatsu et al. *Bioorg. Med. Chem.* 2007, 15, 3115-3126; in R. E. Gawley et al. *J. Org. Chem.* 2007, 72, 2187-2191; or in C. Hardouin et al. *J. Med. Chem.* 2007, 50, 3359-3368.

The reaction of the aldehyde of formula 8 with the amine of formula 9 (preparation thereof described hereinafter) can be carried out using one of a number of well known reactions, in a process known as reductive amination. For example, the aldehyde of formula 8 may be treated with the amine of formula 9 to give an intermediate imine which can be reduced to give the compound of formula 10. The reduction can be carried out using hydrogenation under noble metal catalysis, or it can be carried out by treating the imine with a reducing agent such as sodium borohydride or sodium cyanoborohydride or preferably sodium triacetoxyborohydride. The imine formation and reduction can be carried out as two separate steps, or they can be combined in a single step. The one-step approach is convenient and is well known to one of average skill in the art of organic synthesis. A review on this reaction with particular focus on the use of sodium triacetoxyborohydride as the reducing agent has recently been published (A. F. Abdel-Magid and S. J. Mehrman *Org. Process Res. Dev.* 2006, 10, 971-1031). The reaction is conveniently carried out by treating the aldehyde of formula 8 with the amine of formula 9 in an inert solvent such as a halogenated hydrocarbon (for example dichloromethane or 1,2-dichloroethane) in the optional additional presence of an agent that absorbs water such as molecular sieves, at about room temperature. A reducing agent such as sodium cyanoborohydride or preferably sodium triacetoxyborohydride is added either at the same time as the aldehyde of formula 8 and the amine of formula 9 are combined, or after an interval, such as about one hour. Examples of conditions that can be used for this reaction can be found in the literature, for example in W. Sallem et al. *Bioorg. Med. Chem.* 2006, 14, 7999-8013; in WO 2006014133; in E. Bogatcheva et al. *J. Med. Chem.* 2006, 49, 3045-3048; and in D. H. Boschelli et al. *J. Med. Chem.* 2004, 47, 6666-6668.

The reaction of the secondary amine of formula 10 with an aldehyde of formula 13 (availability and preparation thereof discussed hereinafter) is another example of a reductive amination (of the aldehyde of formula 13). This reaction can be carried out under reactions conditions analogous to those described above for the conversion of the aldehyde of formula 8 to the secondary amine of formula 10.

In addition to the process outlined in Scheme 1, compounds of formula 1 can be prepared by the process shown in Scheme 2.

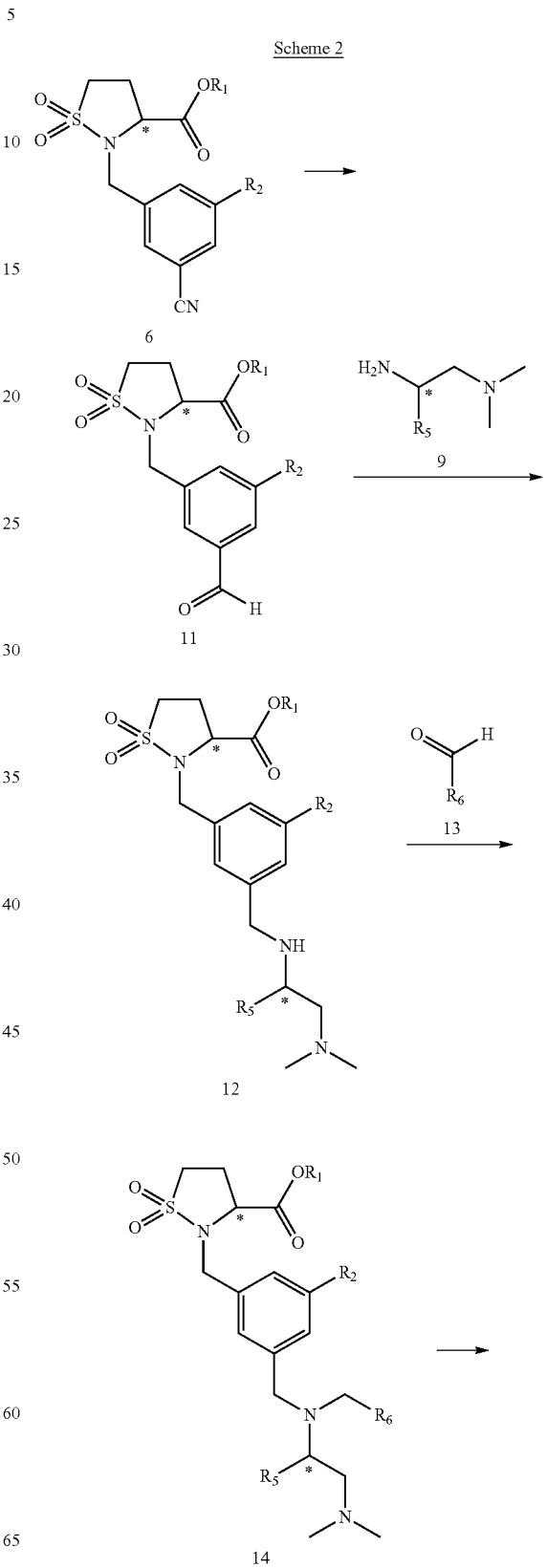

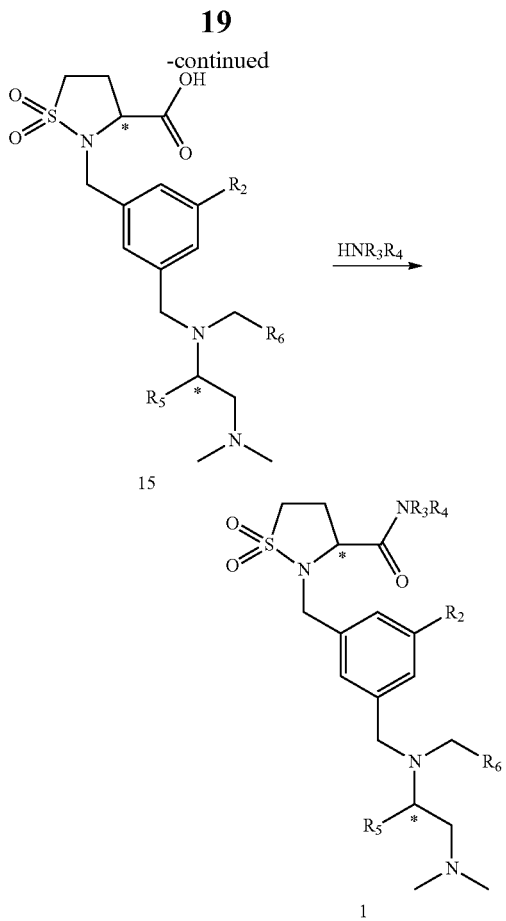

According to this process, the intermediate of formula 6 (as described in Scheme 1) can be converted to the aldehyde of formula 11. Reductive amination of the aldehyde gives the secondary amine of formula 12. Reductive alkylation of the amine with an aldehyde of formula 13 gives the tertiary amine of formula 14. Hydrolysis of the ester followed by coupling with an amine of formula HNR$_3$R$_4$ then gives the compound of formula 1.

Conversion of the nitrile of formula 6 to the aldehyde of formula 11 can be carried out using any conventional means. For example the nitrile may be subjected to hydrogenation in the presence of Raney nickel in an inert solvent such as aqueous formic acid at about 100° C. Examples of precise conditions suitable for carrying out such a reaction can be found in the literature, for example in A. Tanaka et al. *J. Med. Chem.* 1998, 41, 2390-2410; or in R. J. Sundberg et al. *J. Heterocyclic Chem.* 1988, 25, 129-137. Alternatively, the nitrile may be treated with diisobutylaluminum hydride in an inert solvent such as toluene or a mixture of dichloromethane and hexane at a temperature between about −5° C. and about 0° C. Examples of precise conditions suitable for carrying out such a reaction can be found in the literature, for example in E. Fischer WO 2007147547; in T. Komatsu et al. *Bioorg. Med. Chem.* 2007, 15, 3115-3126; in R. E. Gawley et al. *J. Org. Chem.* 2007, 72, 2187-2191; or in C. Hardouin et al. *J. Med. Chem.* 2007, 50, 3359-3368.

The reaction of the aldehyde of formula 11 with the amine of formula 9 (preparation thereof described hereinafter) can be carried out using one of a number of well known reactions, in a process known as reductive amination. For example, the aldehyde of formula 11 may be treated with the amine of formula 9 to give an intermediate imine which can be reduced to give the compound of formula 12. The reduction can be carried out using hydrogenation under noble metal catalysis, or it can be carried out by treating the imine with a reducing agent such as sodium borohydride or sodium cyanoborohydride or preferably sodium triacetoxyborohydride. The imine formation and reduction can be carried out as two separate steps, or they can be combined in a single step. The one-step approach is convenient and is well known to one of average skill in the art of organic synthesis. A review on this reaction with particular focus on the use of sodium triacetoxyborohydride as the reducing agent has recently been published (A. F. Abdel-Magid and S. J. Mehrman *Org. Process Res. Dev.* 2006, 10, 971-1031). The reaction is conveniently carried out by treating the aldehyde of formula 11 with the amine of formula 9 in an inert solvent such as a halogenated hydrocarbon (for example dichloromethane or 1,2-dichloroethane) in the optional additional presence of an agent that absorbs water such as molecular sieves, at about room temperature. A reducing agent such as sodium cyanoborohydride or preferably sodium triacetoxyborohydride is added either at the same time as the aldehyde of formula 11 and the amine of formula 9 are combined, or after an interval, such as about one hour. Examples of conditions that can be used for this reaction can be found in the literature, for example in W. Sallem et al. *Bioorg. Med. Chem.* 2006, 14, 7999-8013; in WO 2006014133; in E. Bogatcheva et al. *J. Med. Chem.* 2006, 49, 3045-3048; and in D. H. Boschelli et al. *J. Med. Chem.* 2004, 47, 6666-6668.

The reaction of the secondary amine of formula 12 with an aldehyde of formula 13 (availability and preparation thereof described hereinafter) is another example of a reductive amination (of the aldehyde of formula 13). This reaction can be carried out under reactions conditions analogous to those described above for the conversion of the aldehyde of formula 11 to the secondary amine of formula 12.

The hydrolysis of the ester functionality in the tertiary amine of formula 14 can be carried out using conditions that are well known in the field of organic synthesis, many of which are outlined in "Protective Groups in Organic Synthesis" [T. W. Greene and P. G. M. Wuts, 2$^{nd}$ Edition, John Wiley & Sons, N.Y. 1991]. For example, in the case where R$_1$ represents methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about room temperature, preferably at about room temperature.

The coupling of a carboxylic acid of formula 15 with an amine of structure HNR$_3$R$_4$ (availability and preparation thereof described hereinafter), according to Scheme 2, can be achieved using methods well known to one of ordinary skill in the art. For example, the transformation can be carried out by reaction of a carboxylic acid of formula 15 or of an appropriate derivative thereof such as an activated ester, with an amine of structure HNR$_3$R$_4$ or a corresponding acid addition salt (e.g., the hydrochloride salt) in the presence, if necessary, of a coupling agent (many examples are well known in peptide chemistry). The reaction is conveniently carried out by treating the carboxylic acid of formula 15 with the hydrochloride of the amine of structure HNR$_3$R$_4$ in the presence of the appropriate base, such as diisopropylethylamine, a coupling agent such as O-(benzotriazol-1-yl)-1,1,3,3-tetramethyluronium hexafluorophosphate or TSTU and in the optional addition presence of a substance that increases the rate of the reaction, such as 1-hydroxybenzotriazole or 1-hydroxy-7- azabenzotriazole, in an inert solvent, such as chlorinated hydrocarbon (e.g., dichloromethane) or N,N-dimethylformamide or N-methylpyrrolidinone, at a temperature between about 0° C. and about room temperature, preferably at room temperature. Alternatively, the reaction can be carried out by converting the carboxylic acid of formula 15 to an activated ester derivative, such as the N-hydroxysuccinimide ester, and subsequently reacting this with the amine of structure HNR$_3$R$_4$ or a corresponding addition salt. This reaction sequence can be carried out by reacting the carboxylic acid of formula 15 with N-hydroxysuccinimide or 1-hydroxybenzotriazole in the presence of a coupling agent such as N,N'-dicyclohexylcarbodiimide or 1-ethyl-3-(3'-dimethylaminopropyl)carbodiimide in an inert solvent such as tetrahydrofuran or dichloromethane at a temperature between about 0° C. and room temperature. The resulting N-hydroxysuccinimide ester or 1-hydroxybenzotriazole ester is then treated with the amine of structure HNR$_3$R$_4$ or a corresponding acid addition salt, in the presence of a base, such as an organic base (e.g., triethylamine or diisopropylethylamine or the like) in a suitable solvent such as N,N-dimethylformamide at around room temperature.

Scheme 3 outlines an alternative process which can be used to convert the intermediate of formula 12 to the compound of the invention of formula 1.

Scheme 3

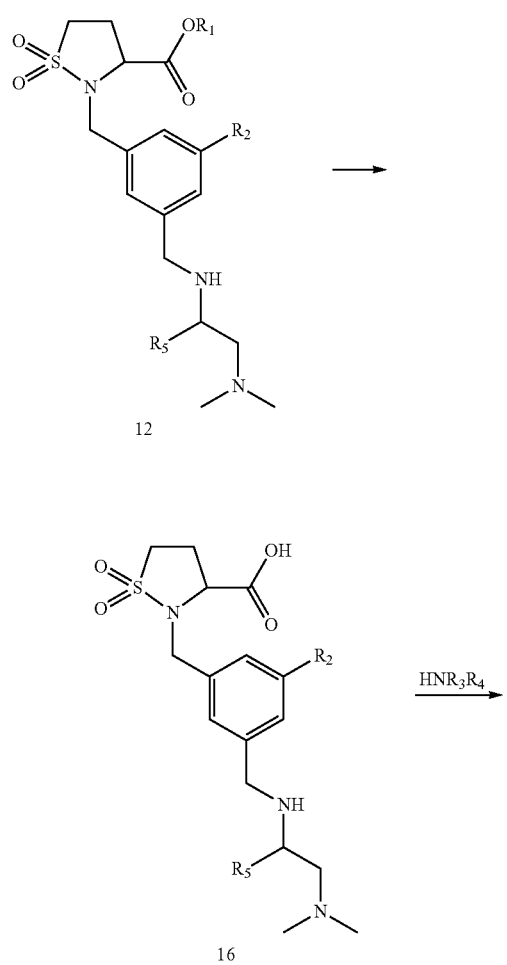

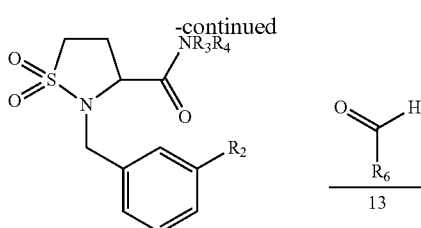

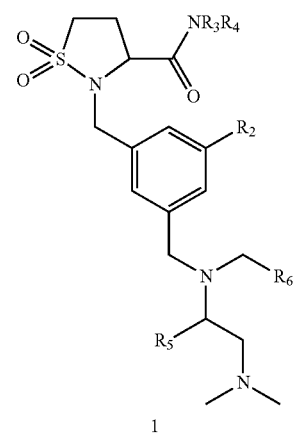

According to the process shown in Scheme 3, the ester group in the compound of formula 12 is cleaved to give the acid of formula 16. Coupling with an amine of formula HNR$_3$R$_4$ then gives the amide of formula 17, and a reductive alkylation of the secondary amine then gives the compound of formula 1.

The hydrolysis of the ester functionality in the secondary amine of formula 12 can be carried out using conditions that are well known in the field of organic synthesis, many of which are outlined in "Protective Groups in Organic Synthesis" [T. W. Greene and P. G. M. Wuts, $2^{nd}$ Edition, John Wiley & Sons, N.Y. 1991]. For example, in the case where R$_1$ represents methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about room temperature, preferably at about room temperature.

The coupling of a carboxylic acid of formula 16 with an amine of structure HNR$_3$R$_4$ (availability and preparation thereof described hereinafter), according to Scheme 3, can be achieved using methods well known to one of ordinary skill in the art. For example, the transformation can be carried out by reaction of a carboxylic acid of formula 16 with an amine of structure HNR$_3$R$_4$ or a corresponding acid addition salt (e.g., the hydrochloride salt) in the presence of a coupling agent, many examples are well known in peptide chemistry. The reaction is conveniently carried out by treating the carboxylic acid of formula 16 with the free base or with the hydrochloride of the amine of structure HNR$_3$R$_4$ in the presence of an appropriate base, such as diisopropylethylamine, a coupling agent such as O-(benzotriazol-1-yl)-1,1,3,3-tetramethyluronium hexafluorophosphate or TSTU and in the optional addition presence of a catalyst such as 1-hydroxybenzotriazole or 1-hydroxy-7-azabenzotriazole, in an inert solvent, such as chlorinated hydrocarbon (e.g., dichloromethane) or N,N-dimethylformamide or N-methylpyrrolidinone, at a temperature between about 0° C. and about room temperature, preferably at room temperature. Many alternative coupling procedures are well known in the field of synthetic chemistry and some have been outlined above, for example in the description of conditions for the conversion of the compound of formula 15 to the compound of formula 1.

The reaction of the aldehyde of formula 13 (availability and preparation thereof described hereinafter) with the amine of formula 17 can be carried out using one of a number of well known reactions, in a process known as reductive amination. For example, the aldehyde of formula 13 may be treated with the amine of formula 17 to give an intermediate imine which can be reduced to give the compound of formula 1. The imine formation and reduction can be carried out as two separate steps, or they can be combined in a single step. The one-step approach is convenient and is well known to one of average skill in the art of organic synthesis. A review on this reaction with particular focus on the use of sodium triacetoxyborohydride as the reducing agent has recently been published (A. F. Abdel-Magid and S. J. Mehrman *Org. Process Res. Dev.* 2006, 10, 971-1031). The reaction is conveniently carried out by treating the aldehyde of formula 13 with the amine of formula 17 in an inert solvent such as dichloromethane in the optional additional presence of an agent that absorbs water such as molecular sieves, at about room temperature. A reducing agent such as sodium cyanoborohydride or sodium triacetoxyborohydride is added either at the same time as the aldehyde of formula 13 and the amine of formula 17 are combined, or after an interval, such as about one hour. Examples of conditions that can be used for this reaction can be found in the literature, for example in W. Sallem et al. *Bioorg. Med. Chem.* 2006, 14, 7999-8013; in WO 2006014133; in E. Bogatcheva et al. *J. Med. Chem.* 2006, 49, 3045-3048; and in D. H. Boschelli et al. *J. Med. Chem.* 2004, 47, 6666-6668.

Compounds of the invention where $R_2$ represents dimethylamino may also be prepared using the route outlined in Scheme 4.

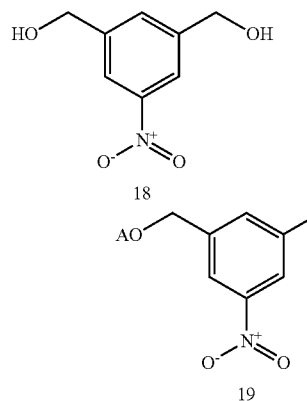

Scheme 4

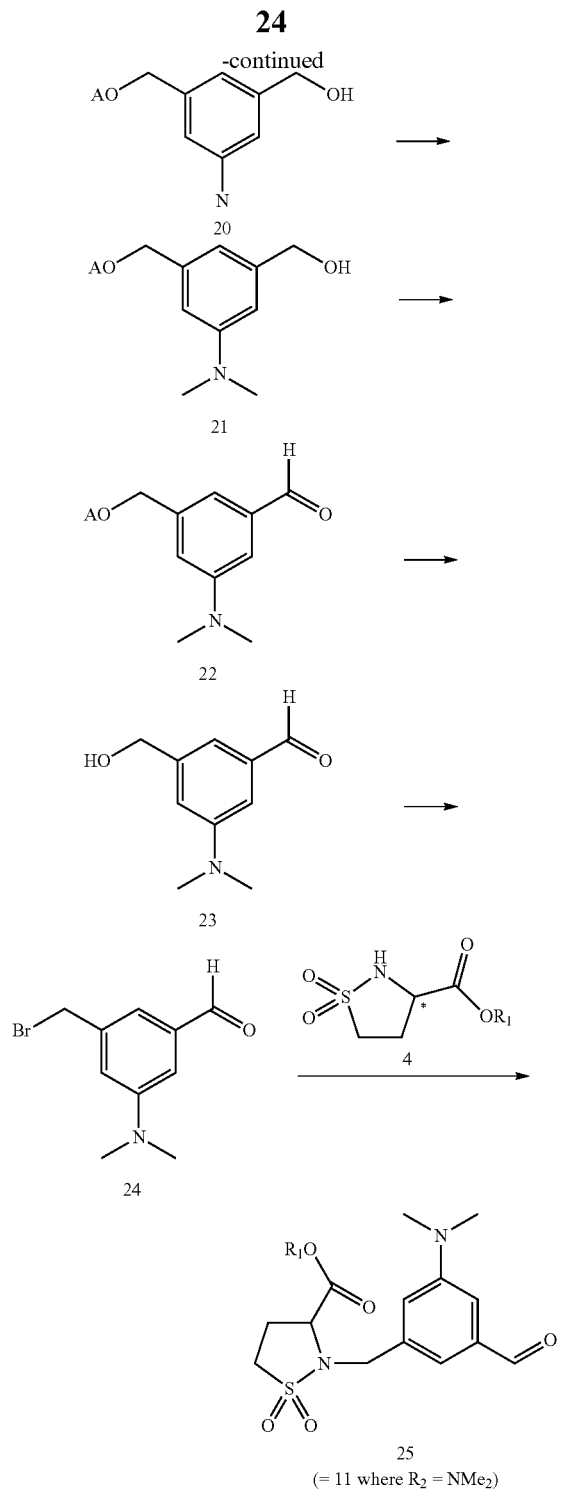

According to this process, the compound of formula 18, (3-hydroxymethyl-5-nitro-phenyl)-methanol, is mono-protected to give the compound of formula 19, where A represents a protective group. Reduction of the nitro group then gives aniline 20, and dimethylation of the aniline nitrogen gives the dimethylamino compound 21. Oxidation of the benzylic alcohol in 21 gives aldehyde 22. Removal of the protective group gives alcohol 23. The alcohol is converted to the benzyl bromide to give intermediate 24. Reaction of intermediate 24 with sultam 4 then gives compound 25, which is also a compound of formula 11 where $R_2$ represents dimethylamino. Compound 25 may then be converted to a compound of formula 1 using the sequence of steps outlined in Scheme 2.

The compound of formula 18 is commercially available. For example, it may be purchased from Aldrich Chemical Co., Milwaukee, Wis., USA. The conversion of the diol of formula 18 to the monoprotected alcohol of formula 19 may be achieved by any conventional means using one of a number of protective groups for alcohols that are well known in the field of organic synthesis. For example, many suitable groups are outlined in "Protective Groups in Organic Synthesis" [T. W. Greene and P. G. M. Wuts, $2^{nd}$ Edition, John Wiley & Sons, N.Y. 1991]. One such suitable group is the tert-butyldimethylsilyl (TBDMS) group. This may be conveniently installed by treating the diol with tert-butyldimethylsilyl chloride in an inert solvent such as dichloromethane in the presence of imidazole between about 0° C. and about room temperature. In this case, the reaction mixture will be converted into a statistical mixture of starting material, monoprotected diol, and diprotected diol in a ratio of approximately 1:2:1 if one equivalent of tert-butyldimethylsilyl chloride is used. The desired monoprotected compound of formula 19 is then isolated from this mixture using techniques that are obvious to one of average skill in the art of organic chemistry such as by silica gel chromatography.

The reduction of the nitro group in the compound of formula 19 to give the aniline derivative of formula 20 may be achieved using one of a variety of processes well known to an organic chemist, such as those outlined in "Comprehensive Organic Transformations: A Guide to Functional Group Preparations" [R. C. Larock, VCH Publishers, Inc. New York, 1989], for example on pages 412-415. A convenient process is to treat a solution of the compound of formula 19 with hydrogen gas in an inert solvent such as ethanol in the presence of a noble metal catalyst such as palladium-on-carbon at about room temperature.

The aniline of formula 20 may be converted to the dimethylamino derivative of formula 21 by treatment with formaldehyde in the presence of a reducing agent such as sodium cyanoborohydride in the presence of a Lewis acid catalyst such as zinc chloride in an inert solvent such as methanol at a temperature about room temperature. The formaldehyde may be generated by heating commercially available paraformaldehyde so that it forms a gas which can then be introduced into the reaction mixture. Examples of specific reaction conditions that can be used for such a reaction may be found in the literature, such as for example in R. G. Carter et al. WO 2008156656; in M. Ono et al. Bioorg. Med. Chem. 2008, 16, 6867-6872; in H. Sueoka et al. U.S. Pat. No. 6,288,061; and in B. D. Allison et al. J. Med. Chem. 2006, 49, 6371-6390.

The alcohol of formula 21 may then be converted to the aldehyde of formula 22 using one of a variety of well known reactions. Examples of precise conditions suitable for carrying out the oxidation of a benzylic alcohol to a benzaldehyde can be found in the literature, for example in J. S. Yadav et al. Tetrahedron 2004, 60, 2131-2135; in C. Kuhakam et al. Synth. Commun. 2006, 36, 2887-2892; in C. Theeraladanon et al. Tetrahedron 2004, 60, 3017-3035; in H. Zhao and A. Thurkauf Synth. Commun. 2001, 31, 1921-1926; in A. W. White et al. J. Med. Chem. 2000, 43, 4084-4097; in J. Clayden et al. Tetrahedron 2004, 60, 4399-4412; in N. Maezaki et al. Tetrahedron 2000, 56, 7927-7945; in A. P Combs et al. J. Med. Chem. 2006, 49, 3774-3789; and in R. M. Moriarty et al. J. Org. Chem. 2004, 68, 1890-1902.

The protected derivative of formula 22 may then be converted to the alcohol of formula 23 using one of a variety of conditions known to be useful for the deprotection of protected alcohols. These conditions depend on the nature of the protective group, and a list of suitable conditions may be found in "Protective Groups in Organic Synthesis" [T. W. Greene and P. G. M. Wuts, $2^{nd}$ Edition, John Wiley & Sons, N.Y. 1991]. For example, in the case where the protective group is tert-butyldimethylsilyl, the protective group may be removed by treating the compound of formula 21 with aqueous acetic acid at about room temperature.

The conversion of the alcohol of formula 23 to the benzyl bromide of formula 24 may be effected by treating a compound of formula 23 with phosphorus tribromide or a mixture of N-bromosuccinimide and triphenylphosphine or a mixture of carbon tetrabromide and triphenylphosphine in an inert solvent such as a halogenated alkane (e.g., methylene chloride or carbon tetrachloride or 1,2-dichloroethane) or tetrahydrofuran or N,N-dimethylformamide at a temperature between about 0° C. and the boiling point of the solvent, conveniently at about 0° C. Examples of precise conditions suitable for carrying out such a substitution reaction can be found in the literature, for example in S. Rapposelli et al. Heterocycles 2008, 75, 1467-1477; in W. Zeng and S. R. Chemler J. Org. Chem. 2008, 73, 6045-6047; in Nicolaou, K. C. et al. Tetrahedron 2008, 64, 4736-4757; and in P. Sehnal et al. J. Org. Chem. 2008, 73, 2074-2082.

The reaction of the compound of formula 4 with a compound of formula 24 to provide a compound of formula 25 can be carried out using a variety of conditions that are well known to one of ordinary skill in the art. For example, the compound of formula 4 can be reacted with a compound of formula 24 in the presence of an appropriate base, such as a metal carbonate (such as potassium carbonate, cesium carbonate, sodium carbonate or lithium carbonate, preferably potassium carbonate) or a metal hydride (such as sodium hydride or potassium hydride) in a suitable solvent such as N,N-dimethylformamide and/or tetrahydrofuran. The reaction can be carried out between about 0° C. and room temperature, preferably at room temperature. Examples of conditions for this reaction can be found in the literature, for example, in R. J. Cherney et al. Bioorg. Med. Chem. Lett. 2006, 16, 1028-1031; and R. J. Cherney et al. J. Med. Chem. 2004, 47, 2981-2983.

As mentioned above, the compound of formula 25 is an example of a compound of formula 11 where $R_2$ represents dimethylamino. Compounds of formula 25 may be converted to compounds of the invention of formula 1 where $R_2$ represents dimethylamino by following the sequence of steps described in Scheme 2 for the conversion of a compound of formula 11 to a compound of formula 1.

Availability of Nitrile Reagents of Formula 5

Two nitrile reagents of formula 5 are commercially available. 3-Cyano-benzyl bromide is available from Aldrich Chemical Company, Inc., Milwaukee, Wis., USA. 3-Cyano-benzyl alcohol is available from TCI America, Portland, Oreg., USA.

A nitrile of formula 5 in which $R_2$ represents dimethylamino may be conveniently prepared from 3-cyano-5-dimethylaminobenzoic acid, the synthesis of which is described in A. Slassi et al. WO 2002068417. According to this procedure the acid is treated with a chloroformate reagent such as methyl chloroformate or ethyl chloroformate in the presence of a base such as triethylamine in an inert solvent such as toluene at a temperature below about 0° C. The conditions described in J. A. Price and D. S. Tarbell Org. Syntheses 1957, 37, 20-23 may be used conveniently to effect this transformation. A solution of the resulting mixed anhydride in tetrahydrofuran may then be added to a solution of sodium borohydride in a mixture of tetrahydrofuran and water at a temperature between about 0° C. and about room temperature to effect reduction to the alcohol of formula 5 in which $R_2$ represents dimethylamino and X represents hydroxyl. This compound may be conveniently converted into the compound of formula 5 where $R_2$ represents dimethylamino and X represents bromine by treating it with phosphorus tribromide or a mixture of N-bromosuccinimide and triphenylphosphine as described above.

Alternative Preparation of Aldehydes of Formula 8

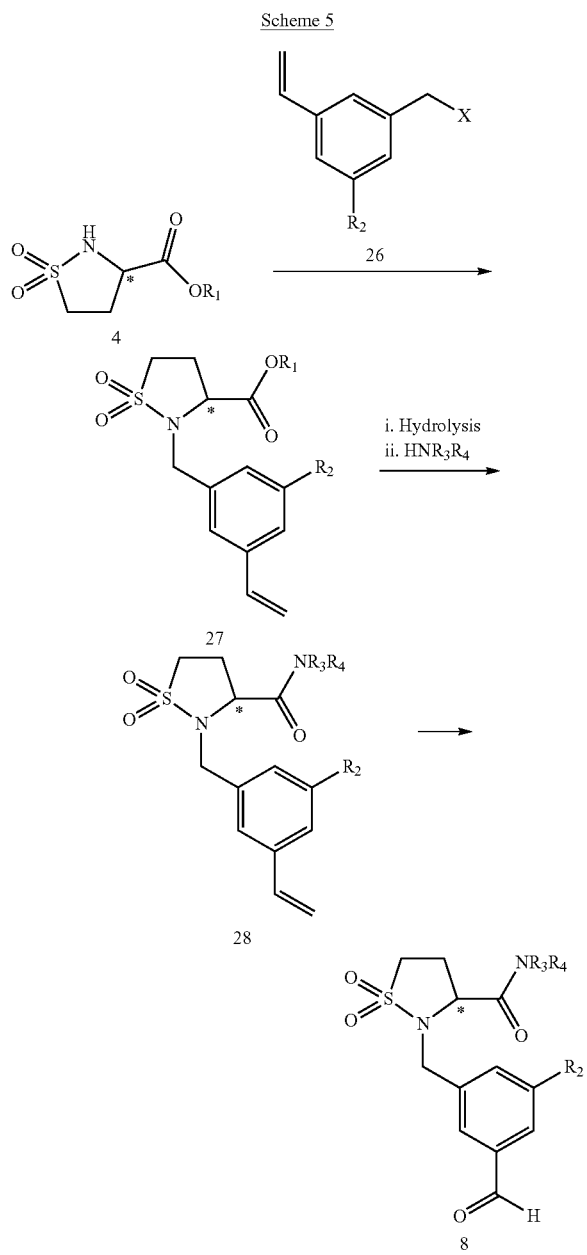

It will be readily apparent to one of average skill in the art of synthetic organic chemistry that the transformation of the reagent of formula 4 to the reagent of formula 8 can be carried out using processes other than that outlined in Scheme 1. For example, this transformation may be carried out by using the vinyl reagent of formula 26 (availability and preparation thereof discussed hereinafter), as shown in Scheme 5.

According to this process, the compound of formula 4 is alkylated with the reagent of formula 26 to give the intermediate of formula 27. Hydrolysis of the ester followed by amide coupling leads to the intermediate of formula 28, and then ozonolysis or oxidative cleavage is used to deliver the aldehyde of formula 8.

The reaction of the compound of formula 4 with a compound of formula 26, where $R_2$ is hydrogen or dimethylamino and X is a suitable leaving group such as a halide (for example, bromine, chlorine, iodine), alkyl or aryl sulfonate ester (for example, methane sulfonate or toluene sulfonate), to provide a compound of formula 27 can be carried out using a variety of conditions that are well known to one of ordinary skill in the art and which conditions are entirely analogous to those described above in connection with the preparation of the compound of formula 6.

The hydrolysis of a compound of formula 27 to the corresponding carboxylic acid is carried out using conditions that are well known in the field of organic synthesis, many of which are outlined in "Protective Groups in Organic Synthesis" [T. W. Greene and P. G. M. Wuts, $2^{nd}$ Edition, John Wiley & Sons, N.Y. 1991], and which are again entirely analogous to those described above in connection with the hydrolysis of the compound of formula 6.

The coupling of a carboxylic acid of formula 27 where $R_1$ represents hydrogen with an amine of structure $HNR_3R_4$ (availability and preparation thereof discussed hereinafter), according to Scheme 5, can be achieved using methods well known to one of ordinary skill in the art, and analogous to those described above for the preparation of a compound of formula 7 from a compound of formula 6 where $R_1$ represents hydrogen.

The reaction of the compound of formula 28 where $R_2$ is hydrogen or dimethylamino to provide a compound of formula 8 can be carried out using a variety of conditions that are well known to one of ordinary skill in the art. For example, the compound of formula 28 can be reacted with a mixture of osmium tetroxide and sodium periodate in an inert solvent such as a mixture of tetrahydrofuran and water or a mixture of acetone and water at about room temperature. Examples of specific conditions for such a reaction can be found in the literature, for example in C. Plisson et al. *J. Med. Chem.* 2007, 50, 4553-4560; in J.-U. Chung et al. *Bioorg. Med. Chem.* 2007, 15, 6043-6053; or in C. Flentge et al. US 20050131042. Alternatively, the compound of formula 28 can be treated with ozone gas in an inert solvent such as a mixture of acetone and ethanol or in dichloromethane at low temperature such as at about −10° C. or about −78° C., and the resulting ozonide can be treated without isolation with a reducing agent such as zinc powder in the presence of acetic acid or dimethyl sulfide to give the aldehyde of formula 8. Examples of specific conditions for such a reaction can be found in the literature, for example in H. Maeda et al. *J. Org. Chem.* 2005, 70, 9693-9701; in A. I. Hikari et al. *J. Med. Chem.* 2003, 46, 3152-3161; or in S. L. Swann et al. *J. Am. Chem. Soc.* 2002, 124, 13795-13805.

Bromomethyl-3-vinyl-benzene, the compound of formula 26 where $R_2$ represents hydrogen and X represents bromine may be conveniently prepared using the procedure disclosed in A. Naghipour et al. *Polyhedron* 2008, 27, 1947-1952.

Bromomethyl-3-dimethylamino-5-vinyl-benzene, the compound of formula 26 where $R_2$ represents dimethylamino and X represents bromine may be prepared in four steps from methyl 3-dimethylamino-5-hydroxybenzoate, the synthesis of which is described in R. W. Rickards et al. WO 1984000750. According to this procedure, methyl 3-dimethylamino-5-hydroxybenzoate is converted to the triflate by reaction with trifluoromethanesulfonic anhydride in the presence of a base such as triethylamine, diisopropylethylamine or pyridine in an inert solvent such as dichloromethane between about −10° C. and about room temperature. The triflate then undergoes a vinylation reaction using vinyltributyltin in the presence of a palladium catalyst such as bis(triphenylphosphine)palladium(II) chloride in an inert solvent such as dioxane at about 100° C. to give 3-dimethylamino-5-vinyl-benzoic acid methyl ester. The ester is reduced by treatment with lithium aluminum hydride in an inert solvent such as ether or tetrahydrofuran at a temperature between about 0° C. and about 35° C. to give (3-dimethylamino-5-vinyl-phenyl)-methanol. This compound may be conveniently converted into the compound of formula 26 where $R_2$ represents dimethylamino and X represents bromine by treating it with phosphorus tribromide or a mixture of N-bromosuccinimide and triphenylphosphine as described above for the preparation of compounds of formula 5 where X represents bromine.

Preparation of Amines of Formula 9

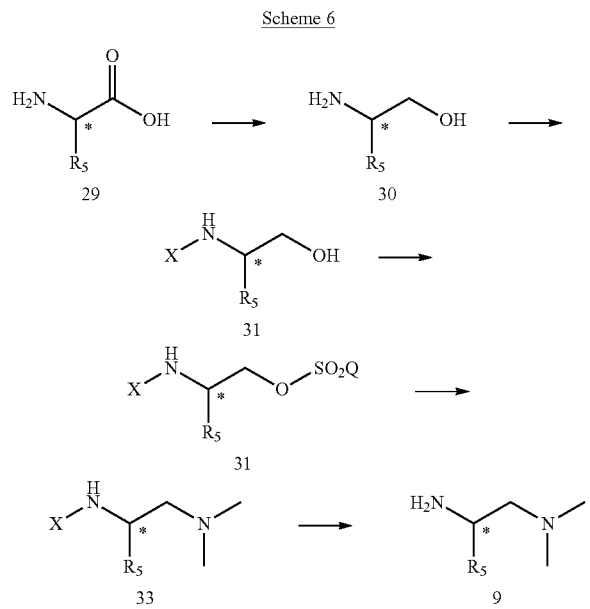

One general approach to the transformation of a compound of the formula 29 (availability and preparation thereof discussed hereinafter) to the compound of formula 9 is outlined in Scheme 6. The reaction of a carboxylic acid of the formula 29 to the alcohol of formula 30 can be achieved using methods well known to one of ordinary skill in the art. For example, the transformation can be carried out by reaction of a carboxylic acid of formula 29, or of an appropriate derivative thereof (such as an ester group), with a suitable reducing agent such as lithium aluminum hydride or lithium borohydride, preferably lithium borohydride, and the like and in a suitable ethereal solvent such as tetrahydrofuran, and the like, at a temperature between about 0° C. and about room temperature, preferably at room temperature, to provide a compound of formula 30. This reaction may be carried out in the presence of trimethylsilyl chloride. The amine of formula 30 is then converted to the protected derivative 31. Suitable nitrogen protective groups include tert-butoxycarbonyl, benzyl, and the like, and many appropriate groups can be found in T. Greene and P. Wuts, *Protective Groups in Organic Synthesis*, 3rd. Ed., John Wiley and Sons (1999). Protection of the amino group of the compound of formula 30 as the tert-butylcarbamate to give the compound of formula 31 where X represents tert-butoxycarbonyl, can be carried out using one of a number of well-known reactions. For example, the amine of formula 30 may be treated with di-tert-butyl dicarbonate or with 2-(Boc-oxyimino)-2-phenylacetonitrile (BOC—ON) in the presence of a base such as triethylamine or diisopropylethylamine in a solvent such as tetrahydrofuran or acetonitrile or a mixture of dioxane and water at about room temperature. References to procedures useful for protection of the amine with a variety of other protective groups can be found in Greene and Wuts (op. cit.).

Activation of the alcohol of formula 31 with toluenesulfonyl chloride, followed by substitution with a dialkylamine, preferably dimethylamine, provides a compound of the formula 33. The preparation of the toluenesulfonate of formula 32, wherein Q is p-tolyl, can be effected by treating the alcohol of formula 31 with p-toluenesulfonyl chloride in the presence of a base such as triethylamine or diisopropylethylamine or pyridine in an inert solvent such as dichloromethane at a temperature between about 0° C. and about room temperature. The conversion of the tosylate of formula 32 to the amine of formula 33 is conveniently carried out by treating the compound of formula 32 with dimethylamine or dimethylamine hydrochloride in the presence of a base such as triethylamine or diisopropylethylamine or pyridine in an inert solvent such as dichloromethane at a temperature between about 0° C. and about room temperature. Alternatively, the reaction may be carried out using pyridine as solvent in the absence of an additional solvent. Examples of specific conditions that may be used for this reaction can be found in J. Christoffers and A. Mann *Chem. Eur. J.* 2001, 7, 1014-1027.

Deprotection of a compound of the formula 33 to provide a compound of the formula 9, can be achieved using reactions well known by one of ordinary skill in the art. For example, reaction of a compound of the formula 33 with a protic acid (such as trifluoroacetic acid or hydrochloric acid), in an suitable inert solvent, such as dichloromethane or an ethereal solvent such as diethyl ether, and the like, at a temperature of 0° C. to room temperature, preferably at room temperature. Examples of specific conditions for such a reaction can be found in T. Greene and P. Wuts, *Protective Groups in Organic Synthesis*, 3rd. Ed., John Wiley and Sons (1999).

It will be readily apparent to one of ordinary skill in the art of synthetic organic chemistry that the transformation of the reagent of formula 29 to the reagent of formula 9 can be carried out using processes other than that outlined in Scheme 6. For example, this transformation may be carried out by using the reaction sequence outlined in Scheme 7.

Scheme 7

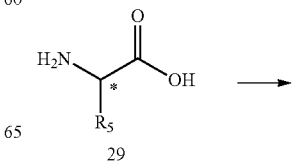

-continued

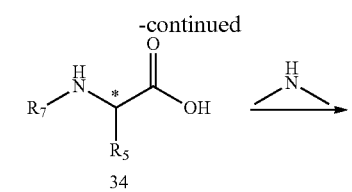
34

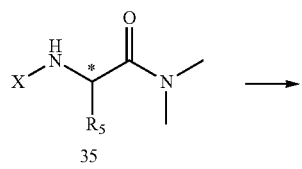
35

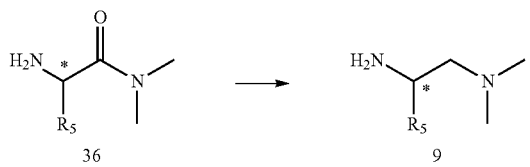
36 9

A compound of the formula 29 can be conveniently reacted with a suitable nitrogen protecting group. Suitable nitrogen protecting groups include tert-butoxycarbonyl, benzyl, and the like. Other amino protecting groups for a compound of the formula 29 can be found in T. Greene and P. Wuts, *Protective Groups in Organic Synthesis,* 3rd. Ed., John Wiley and Sons (1999). Protection of the amino group of the compound of formula 29 as the tert-butylcarbamate to give the compound of formula 34 where X represents tert-butoxycarbonyl, can be carried out using one of a number of well-known reactions. For example, the amine of formula 29 may be treated with di-tert-butyl dicarbonate or with 2-(Boc-oxyimino)-2-phenylacetonitrile (BOC—ON) in the presence of a base such as triethylamine or diisopropylethylamine in a solvent such as tetrahydrofuran or acetonitrile or a mixture of dioxane and water at about room temperature. References to procedures useful for protection of the amine with a variety of other protective groups can be found in Greene and Wuts (op. cit.).

The coupling of a carboxylic acid of formula 34 with dimethyl amine, according to Scheme 7, to provide a compound of the formula 35 can be achieved using methods well known to one of ordinary skill in the art. For example, the transformation can be carried out by reaction of a carboxylic acid of formula 34 or of an appropriate derivative thereof such as an activated ester, with an amine of structure $HNMe_2$ or a corresponding acid addition salt (e.g., the hydrochloride salt) in the presence, if necessary, of a coupling agent, many examples are well known in peptide chemistry. The reaction is conveniently carried out by treating the carboxylic acid of formula 34 with dimethylamine (either as the free base or as the hydrochloride salt) in the presence of an appropriate base, such as diisopropylethylamine, a coupling agent, such as O-(benzotriazol-1-yl)-1,1,3,3-tetramethyluronium hexafluorophosphate or TSTU, and optionally in the additional presence of a substance that increases the rate of the reaction, such as 1-hydroxybenzotriazole or 1-hydroxy-7-azabenzotriazole. The reaction is carried out in an inert solvent, such as a chlorinated hydrocarbon (e.g., dichloromethane) or N,N-dimethylformamide or N-methylpyrrolidinone, at a temperature between about 0° C. and about room temperature, preferably at room temperature. Alternatively, the reaction can be carried out by converting the carboxylic acid of formula 34 to an activated ester derivative, such as the N-hydroxysuccinimide ester, and subsequently reacting this with dimethylamine or a corresponding addition salt. This reaction sequence can be carried out by reacting the carboxylic acid of formula 34 with N-hydroxysuccinimide or 1-hydroxybenzotriazole in the presence of a coupling agent such as N,N'-dicyclohexylcarbodiimide or 1-ethyl-3-(3'-dimethylaminopropyl)carbodiimide in an inert solvent such as tetrahydrofuran or dichloromethane at a temperature between about 0° C. and room temperature. The resulting N-hydroxysuccinimide ester or 1-hydroxybenzotriazole ester is then treated with dimethylamine or a corresponding acid addition salt, in the presence of a base, such as an organic base (e.g., triethylamine or diisopropylethylamine or the like) in a suitable solvent such as N,N-dimethylformamide at around room temperature. Examples of specific reaction conditions that can be used to effect this transformation can be found in the literature, for example, in J. J. Baldwin et al. WO 2006042150.

Deprotection of a compound of the formula 35 to provide a compound of the formula 36, can be achieved by one of ordinary in the skill of the art using reaction conditions that depend on the nature of the protective group X. For example, the reaction can be carried out by treating a compound of the formula 35 where X represents tert-butoxycarbonyl with a protic acid (such as trifluoroacetic acid or hydrochloric acid) in an suitable inert solvent, such as dichloromethane or an ethereal solvent such as diethyl ether or the like, at a temperature of 0° C. to room temperature, preferably at room temperature. Examples of specific conditions for such a reaction can be found in T. Greene and P. Wuts, *Protective Groups in Organic Synthesis,* 3rd. Ed., John Wiley and Sons (1999).

The compound of the formula 36 can be conveniently reduced to the corresponding amine of the formula 9 using methods well known to those skilled in the art of organic synthesis. For example, reduction of the compound of the formula 36, with a suitable reducing agent, such as lithium aluminum hydride or lithium borohydride, preferably lithium aluminum hydride, and the like, and in a suitable ethereal solvent, such as tetrahydrofuran and the like, at a temperature between about 0° C. and about room temperature, preferably at room temperature, provides a compound of formula 9.

Alternative Preparation of Certain Aldehydes of Formula 11

Scheme 8

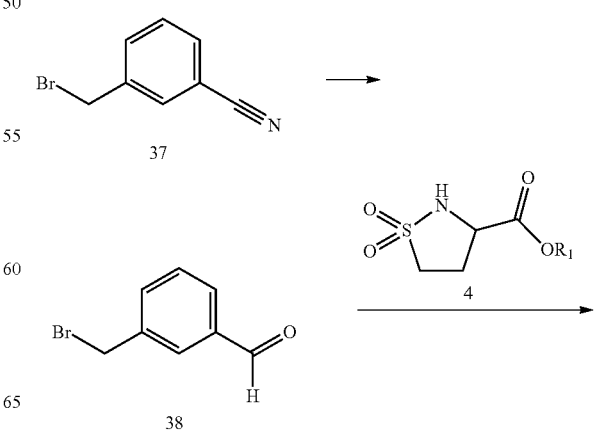

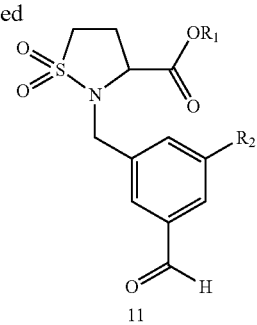

11

In the case where R₂ represents hydrogen, an additional option for the preparation of the compound of formula 11 is shown in Scheme 8. According to this process, 3-(bromomethyl)benzonitrile, which is the compound of formula 37, may be reduced to give the compound of formula 38. This intermediate may then be reacted with the sultam of formula 4 to give the compound of formula 11.

3-(Bromomethyl)benzonitrile, which is the compound of formula 37, is commercially available from vendors such as Aldrich Chemical Company, Inc., Milwaukee, Wis., USA.; Alfa Aesar, Ward Hill, Mass., USA; TCI America, Portland, Oreg., USA; and Acros Organics USA, Morris Plains, N.J., USA The reduction of the compound of formula 37 to give the aldehyde of formula 38 can be conveniently achieved by treating the compound of formula 37 with a reducing agent which is known in the art to be effective in reducing nitriles to aldehydes in the presence of a benzyl halide. An example of such a reducing agent is diisobutylaluminum hydride. The reaction may be carried out by dissolving the compound of formula 37 in an inert solvent such as chlorobenzene and adding a solution of diisobutylaluminum hydride in an inert solvent such as toluene or hexanes at a temperature of about 0° C. Specific conditions useful for carrying out this reaction can be found in the literature, for example in B. C. Bookser and T. C. Bruice *J. Am. Chem. Soc.* 1991, 113, 4208-4218.

The reaction of the compound of formula 4 with the compound of formula 38 to provide a compound of formula 11 can be carried out using a variety of conditions that are well known to one of ordinary skill in the art. For example, the compound of formula 4 can be reacted with a compound of formula 38 in the presence of an appropriate base, such as a metal carbonate (such as cesium carbonate, potassium carbonate, sodium carbonate or lithium carbonate, preferably cesium carbonate) in a suitable solvent such as N,N-dimethylformamide and/or tetrahydrofuran. The reaction can be carried out between about 0° C. and room temperature, preferably at about room temperature.

Availability of Aldehyde Reagents of Formula 13

Many aldehyde reagents of formula 13 are commercially available from a number of suppliers including the following:
- Acros Organics USA, 500 American Road, Morris Plains, N.J. 07950, USA
- Aldrich Chemical Company, Inc., 1001 West Saint Paul Avenue, Milwaukee, Wis. 53233, USA.
- Alfa Aesar, 26 Parkridge Road, Ward Hill, Mass. 01835, USA
- Apollo Scientific Ltd., Whitefield Road, Bredbury, Stockport, Cheshire SK6 2QR, UK.
- Matrix Scientific, P.O. Box 25067, Columbia, S.C. 29224-5067, USA
- Oakwood Products, Inc., 1741 Old Dunbar Road, West Columbia, S.C. 29172, USA.
- TCI America, 9211 N. Harborgate Street, Portland, Oreg. 97203, USA In addition to commercially available reagents, compounds of formula 13 may be made using a number of procedures that are widely known in the field of organic synthesis. A listing of many of these methods can be found in "Comprehensive Organic Transformations: A Guide to Functional Group Preparations" [R. C. Larock, VCH Publishers, Inc. New York, 1989], for example on pages 604-624. Some of the most common reactions used to prepare aldehydes of formula 13 include the oxidation of benzylic alcohols (for example using manganese dioxide, using Swern conditions, using the Dess-Martin periodinane, or using o-iodoxybenzoic acid); the reduction of carboxylic acid derivatives (for example, esters or nitriles) using diisobutylaluminum hydride, sodium bis(2-methoxyethoxy)-aluminum hydride (Red-Al) or the like; palladium-catalyzed carbonylation; lithium-halogen exchange followed by reaction of the anion with a formamide such as N-formyl piperidine or N,N-dimethylformamide; or by oxidative cleavage of the double bond of a vinyl-benzene derivative.

Examples of precise conditions suitable for carrying out the oxidation of a benzylic alcohol to a benzaldehyde can be found in the literature, for example in J. S. Yadav et al. *Tetrahedron* 2004, 60, 2131-2135; in C. Kuhakam et al. *Synth. Commun.* 2006, 36, 2887-2892; in C. Theeraladanon et al. *Tetrahedron* 2004, 60, 3017-3035; in H. Zhao and A. Thurkauf *Synth. Commun.* 2001, 31, 1921-1926; in A. W. White et al. *J. Med. Chem.* 2000, 43, 4084-4097; in J. Clayden et al. *Tetrahedron* 2004, 60, 4399-4412; in N. Maezaki et al. *Tetrahedron* 2000, 56, 7927-7945; in A. P Combs et al. *J. Med. Chem.* 2006, 49, 3774-3789; and in R. M. Moriarty et al. *J. Org. Chem.* 2004, 68, 1890-1902.

Examples of precise conditions suitable for carrying out the reduction of a carboxylate ester to a benzaldehyde can be found in the literature, for example in N. Nakane et al. *J. Org. Chem.* 2004, 69, 3538-3545; T. Abe et al. *Tetrahedron* 2001, 57, 2701-2710; and in R. Kanazawa and T. Tokoroyama *Synthesis* 1976, 526-527.

Examples of precise conditions suitable for carrying out the reduction of a nitrile to a benzaldehyde can be found in the literature, for example in D. Castellnou et al. *Tetrahedron* 2005, 61, 12111-12120; in T. Itoh et al. *J. Am. Chem. Soc.* 2006, 128, 957-967; E. David et al. *J. Org. Chem.* 2005, 70, 3569-3573; and in B. D. Roth et al. *J. Med. Chem.* 1990, 33, 21-31.

Examples of precise conditions suitable for carrying out the conversion of a bromo-benzene or iodo-benzene derivative to a benzaldehyde by metal-halogen exchange followed by formylation can be found in the literature, for example in T. Kliś and J. Serwatowski *Tetrahedron Lett.* 2007, 48, 1169-1173; C. G. Oliveri et al. *J. Am. Chem. Soc.* 2006, 128, 16286-16296; in S. Fergus et al. *J. Org. Chem.* 2004, 69, 4663-4669; and in S. Hibino et al. *Heterocycles* 1989, 28, 275-282.

Examples of precise conditions suitable for carrying out the palladium-catalyzed carbonylation of a halobenzene derivative or the like can be found in the literature, for example in K. Orito et al. *J. Org. Chem.* 1999, 64, 6583-6596; in R. W. Bates et al. *Tetrahedron* 1995, 51, 8199-9212; and in H. Iwamoto et al. *Tetrahedron Lett.* 2002, 43, 8191-8194.

Examples of precise conditions suitable for carrying out the oxidative cleavage of the double bond of a vinyl-benzene derivative can be found in the literature, for example in A. Srikrishna and G. Satyanarayana *Tetrahedron* 2006, 62, 2893-2900; H. Maeda et al. *J. Org. Chem.* 2005, 70, 9693-9701; in A. Hashimoto et al. *Bioorg. Med. Chem.* 2005, 13, 3627-3639; in S. Lai and D. G. Lee *Synthesis* 2001, 1645-1648; in Y.-Z. Hu and D. L. J. Clive *J. Chem. Soc. Perkin Trans.* 11997, 1421-1424; in S. Rao Kasibhatla et al. *J. Med. Chem.* 2000, 43, 1508-1518; and in D. Yang and C. Zhang *J. Org. Chem.* 2001, 66, 4814-4818.

A number of aldehydes of formula 13 may also be made from benzene derivatives with an acidic proton, such as for example a benzene derivative containing a hydrogen on a carbon adjacent to a carbon bearing a fluoro group. Such a benzene derivative may be treated with a strong amide base such as lithium diisopropylamide in an inert solvent such as tetrahydrofuran at low temperature such as between about −78° C. and about −50° C., followed by the addition of a formyl source such as N,N-dimethylformamide or N-formylpiperidine, again at a temperature of about −78° C. Examples of precise conditions suitable for carrying out this reaction can be found in the literature, for example in A. J. Bridges et al. *Tetrahedron Lett.* 1992, 33, 7499-7502; in A. J. Cantrell et al. *J. Med. Chem.* 1996, 39, 4261-4274; in T. Akama. *J. Med. Chem.* 1998, 41, 2056-2067; and in R. J. Mattson et al. *J. Org. Chem.* 1999, 64, 8004-8007.

Alternative Preparation of Carboxylic Acids of Formula 29

Many carboxylic acids or their lower alkyl esters of formula 29 wherein $R_5$ is alkyl, aryl or hydrogen are commercially available from a number of vendors including the following:

Acros Organics USA, Morris Plains, N.J. 07950, USA
Aldrich Chemical Company, Inc., Milwaukee, Wis. 53233, USA.
Alfa Aesar, Ward Hill, Mass. 01835, USA
Apollo Scientific Ltd., Stockport, Cheshire SK6 2QR, UK.
Bachem California Inc., Torrance, Calif., USA
Chem-Impex International, Inc., Wood Dale, Ill. 60191, USA
Oakwood Products, Inc., West Columbia, S.C. 29172, USA.
Sigma-Aldrich Corporation, St. Louis, Mo., USA
TCI America, Portland, Oreg. 97203, USA
3B Scientific Corporation, Libertyville, Ill. 60048, USA In cases where the compounds of formula 29 are not commercially available, they can be prepared using procedures that are well known in the fields of amino acid chemistry and peptide chemistry. A number of reviews have been published on the synthesis of amino acids, including the following: J.-A. Ma *Angew. Chem. Intl. Edn. Engl.* 2003, 42, 4290-4299; G. C. Barrett *Amino Acids, Pept. Prot.* 2001, 32, 1-106; F. A. Davis and B.-C. Chen *Chem. Soc. Rev.* 1998, 27, 13-18; N.J. Turner *Curr. Org. Chem.* 1997, 1, 21-36; M. J. Burk et al. *Pure Appl. Chem.* 1996, 68, 37-44; Y. N. Belokon *Pure Appl. Chem.* 1992, 64, 1917-1924; and H. E. Shoemaker et al. *Pure Appl. Chem.* 1992, 64, 1171-1175. These reviews describe a number of different processes that can be used to synthesize compounds of formula 29.

Availability of Amine Reagents of Formula $HNR_3R_4$

Many amines of formula $HNR_3R_4$ where $R_3$ is hydrogen and $R_4$ is cycloalkyl optionally substituted by alkyl are commercially available and examples are shown below.

The following are compounds of formula $HNR_3R_4$ where $R_3$ is hydrogen and $R_4$ is cycloalkyl optionally substituted by alkyl which are commercially available.

From Sigma-Aldrich Corporation, Saint Louis, Mo. 63178, USA: (−)-isopinocampheylamine; (+)-isopinocampheylamine; (R)-(+)-bornylamine; 1-adamantanamine; 2-methylcyclohexylamine; 4-methylcyclohexylamine; cyclobutylamine; cycloheptylamine; cyclohexylamine; cyclooctylamine; cyclopentylamine; cyclopropylamine; exo-2-aminonorbornane.

From Alfa-Aesar, Ward Hill, Mass., 01835, USA: 1-amino-2-methylcyclohexane; 4-tert-butylcyclohexylamine.

From Allichem LLC, Savage, Md., 20763-9504, USA: 3,3,5,5-tetramethyl-cyclohexylamine; 4,4-dimethylcyclohexylamine; trans-2-methylcyclohexylamine.

From APAC Pharmaceutical, LLC, Columbia, Md., 21045, USA: trans-2-methylcyclohexylamine.

From Aurora Fine Chemicals LLC, San Diego, Calif., 92126, USA: 2-ethylcyclopentanamine; 2-methylcyclopentanamine; hexahydro-2,5-methanopentalen-3a(1H)-amine.

From 3B Scientific Corporation, Libertyville, Ill. 60048, USA: (±)-2-endo-amino-3-exo-isopropylbicyclo[2.2.1]heptane hydrochloride; 2,6-dimethylcyclohexanamine; cis-1-amino-4-tert-butylcyclohexane; 1-menthylamine.

From ChemBridge Corporation, San Diego, Calif. 92127, USA: (1-isopropylcyclopropyl)amine; (3-ethyl-1-adamantyl)amine; (3-isopropyl-1-adamantyl)amine; bicyclo[2.2.1]heptan-2-amine.

From Chemgenx LLC, Rocky Hill, N.J., 08553, USA: cis-4-(1-methylethyl)-cyclohexanamine.

From Enamine, Kiev 01103, Ukraine: 2-ethylcyclohexanamine; 2-isopropyl-5-methylcyclohexanamine; decahydronaphthalen-2-amine.

From Matrix Scientific, Columbia, S.C. 29224-5067, USA: 1-methyl-cyclobutylamine; 2-tert-butylcyclohexanamine; 3,5,7-trimethyl-adamantan-1-ylamine; 4-(1,1-dimethylpropyl)cyclohexanamine; 4-ethylcyclohexanamine.

From SYNCHEM OHG, Felsberg-Altenburg, D-34587, Germany: 1-amino-3-methyladamantane; 2-amino-2-methyladamantane.

From TCI America, Portland, Oreg. 97203, USA: 3,3,5-trimethylcyclohexylamine; trans-4-methylcyclohexylamine.

From TimTec LLC, Newark, Del. 19711, USA: 2-aminoadamantane; 2-tert-butyl-cyclohexylamine; memantine.

From UkrOrgSynthesis, Kiev, 01133, Ukraine: 1-amino-1-methylcyclohexane; 4-propylcyclohexan-1-amine.

In addition to the amines of formula $HNR_3R_4$ where $R_3$ is hydrogen and $R_4$ is cycloalkyl optionally substituted by alkyl that are commercially available, many methods for the preparation of such amines are well known to one of ordinary skill in the art of organic synthesis. Many of these methods are enumerated in "The Chemistry of the Amino Group" [M. S. Gibson; S. Patai Ed.; John Wiley & Sons, Ltd. London 1968, 37-77], in "Advanced Organic Chemistry" [J. March, $3^{rd}$ Edition, John Wiley & Sons, Inc. New York, 1985], on pages 1153-1154, and in "Comprehensive Organic Transformations: A Guide to Functional Group Preparations" [R. C. Larock, VCH Publishers, Inc. New York, 1989] on pages 1061-1063. As one example of the preparation of an amine of formula $HNR_3R_4$, a ketone such as (1R)-(+)-camphor may be converted to the corresponding oxime by treating the ketone with hydroxylamine hydrochloride in an inert solvent such as ethanol at about the reflux temperature of the solvent. The corresponding oxime may then be dissolved in an alcohol such as amyl alcohol and then treated with sodium added in small pieces over an extended period such as about four hours at a temperature about the reflux temperature of the solvent, to give the amine of formula $HNR_3R_4$ which in this case is (−)-endo-bornylamine hydrochloride, a compound where $R_3$ represents hydrogen and $R_4$ represents the bornyl moiety.

Exact conditions for carrying out this reaction can be found in the literature, for example in L. A. Paquette and R. F. Doehner, Jr. *J. Org. Chem.* 1980, 45, 5105-5113.

Amines of formula $HNR_3R_4$ where $R_3$ is hydrogen and $R_4$ is cycloalkyl optionally substituted by alkyl may be made from a cyclic ketone by treating the ketone with hydrogen and ammonia in the presence of a noble metal catalyst such as palladium or ruthenium, either of which may optionally be supported on carbon, in the optional additional presence of ammonium chloride at a temperature of about 200° C. Exact conditions for such a reaction may be found in the literature, for example in T. Ikenaga et al. *Tetrahedron* 2005, 61, 2105-2109.

Amines of formula $HNR_3R_4$ where $R_3$ is hydrogen and $R_4$ is cycloalkyl optionally substituted by alkyl may be made from a cycloalkene by treating the cycloalkene with borane-tetrahydrofuran complex in an inert solvent such as tetrahydrofuran at about room temperature to form the corresponding organoborane, and then treating this material with chloramine in the presence of aqueous sodium hydroxide. Alternatively, the organoborane may be treated with hydroxylamine-O-sulfonic acid in diglyme at about 100° C. to give the amine of formula $HNR_3R_4$. Exact conditions for such a reaction may be found in the literature, for example in H. C. Brown et al. *Tetrahedron* 1987, 43, 4071-4078.

Amines of formula $HNR_3R_4$ where $R_3$ is hydrogen and $R_4$ is cycloalkyl optionally substituted by alkyl may be made from an alcohol of formula $HOR_4$ by conversion to the corresponding azide of formula $N_3R_4$, and subsequent reduction of the azide.

Displacement of the hydroxyl group of the alcohol of formula $HOR_4$ to give the corresponding azido analogue can be achieved by treating a mixture of the alcohol of formula $HOR_4$ and diphenylphosphoryl azide (DPPA) with 1,8-diazabicyclo[5.4.0]undec-7-ene (DBU) under anhydrous conditions at a temperature between about 0° C. and about 10° C. for approximately 18 hours in an inert solvent such as toluene or N,N-dimethylformamide. Exact conditions for carrying out such as reaction can be found in the literature, for example in P. Bremond et al. *Synthesis* 2009, 290-296; in P. Wyrebek et al. *Tetrahedron* 2009, 65, 1268-1275; in H. Ryu et al. *J. Med. Chem.* 2008, 51, 57-67; or in I. Izquierdo et al. *Tetrahedron* 2006, 63, 1440-1447.

Hydrogenation the above azido derivative to give the corresponding amine of formula $HNR_3R_4$ where $R_3$ is hydrogen and $R_4$ is cycloalkyl optionally substituted by alkyl can be carried out in the presence of 5% palladium on carbon under a pressure of hydrogen between about atmospheric pressure and about 350 psi, at room temperature for 1.5 hour, in an organic solvent such as ethyl acetate, methanol, or ethanol. Exact conditions for carrying out such as reaction can be found in the literature, for example in M. Enomoto and S. Kuwarahara *Angew. Chem. Intl. Edn. Engl.* 2009, 48, 1144-1148; in T. Ooi et al. US 2009131716; in X. Wang et al. *Tetrahedron* 2007, 63, 6141-6145; or in N. Ciliberti et al. *Bioorg. Med. Chem.* 2007, 15, 3065-3081.

Alternatively, the reduction of the azide group to give the amine of formula $HNR_3R_4$ where $R_3$ is hydrogen and $R_4$ is cycloalkyl optionally substituted by alkyl can be achieved by treating the azide with triphenylphosphine in an inert solvent such as tetrahydrofuran in the presence of water at a temperature between about room temperature and about 65° C. Exact conditions for carrying out such as reaction can be found in the literature, for example in B. Han et al. WO 2008148689; in G. Liu et al. *Org. Lett.* 2009, 11, 1143-1146; in X. Wang et al. *Tetrahedron* 2007, 63, 6141-6145; or in I. Shimada et al. *Bioorg. Med. Chem.* 2008, 16, 1966-1982.

Amines of formula $HNR_3R_4$ where $R_3$ is hydrogen and $R_4$ is cycloalkyl optionally substituted by alkyl may be made from a tertiary alcohol of formula $HOR_4$ using a Ritter reaction with hydrocyanic acid. According to this procedure, concentrated sulfuric acid is added to a mixture of the tertiary alcohol of formula $HOR_4$ and potassium cyanide in dibutyl ether and the mixture is heated at about 40° C. to give the amine of formula $HNR_3R_4$. Exact conditions for carrying out such as reaction can be found in the literature, for example in M. Mousseron et al. *Bull. Soc. Chim. France* 1957, 596-600 (Chemical Abstracts 51:76818).

Many amines of formula $HNR_3R_4$ where $R_3$ is hydrogen and $R_4$ is benzyl optionally substituted by halogen are commercially available and examples are shown below.

From Acros Organics, Geel, Belgium: 4-bromo-2-fluorobenzylamine.

From Sigma-Aldrich Corporation, Saint Louis, Mo. 63178, USA: 2,3-dichlorobenzylamine; 2,3-difluorobenzylamine; 2,4-dichlorobenzylamine; 2,4-difluorobenzylamine; 2,5-dichlorobenzylamine; 2,5-difluorobenzylamine; 2,6-difluorobenzylamine; 2-chlorobenzylamine; 2-fluorobenzylamine; 3,4-dichlorobenzylamine; 3,4-difluorobenzylamine; 3,5-difluorobenzylamine; 3-chlorobenzylamine; 3-fluorobenzylamine; 3-iodobenzylamine; 4-bromobenzylamine; 4-chlorobenzylamine; 4-fluorobenzylamine; 5-bromo-2-fluorobenzylamine hydrochloride; benzylamine.

From Alfa-Aesar, Ward Hill, Mass., 01835, USA: 2,3,4,6-tetrafluorobenzylamine hydrochloride; 2,3,4-trifluorobenzylamine; 2,3,5-trifluorobenzylamine; 2,3,6-trifluorobenzylamine; 2,3-dichloro-6-fluorobenzylamine; 2,4,5-trifluorobenzylamine; 2,4,6-trifluorobenzyl amine; 2,4-dichloro-5-fluorobenzylamine; 2,6-dichlorobenzylamine; 2-bromobenzylamine; 2-chloro-3,6-difluorobenzylamine; 2-chloro-4,5-difluorobenzylamine; 2-chloro-4-fluorobenzylamine; 2-chloro-5-fluorobenzylamine; 2-chloro-6-fluorobenzylamine; 3,4,5-trifluorobenzylamine; 3,5-dichlorobenzylamine; 3-bromo-4-fluorobenzylamine hydrochloride; 3-bromobenzylamine; 3-chloro-2,4-difluorobenzylamine; 3-chloro-2,6-difluorobenzylamine; 3-chloro-2-fluorobenzylamine; 3-chloro-4-fluorobenzylamine; 3-chloro-5-fluorobenzylamine; 4-chloro-2,6-difluorobenzylamine; 4-chloro-2-fluorobenzyl amine; 4-chloro-3-fluorobenzylamine; 4-iodobenzylamine; 5-chloro-2-fluorobenzylamine.

From Allichem LLC, Savage, Md., 20763-9504, USA: 5-bromo-2-(aminomethyl)-1,3-difluorobenzene; 5-bromo-2,3-difluorobenzyl amine.

From 3B Scientific Corporation, Libertyville, Ill. 60048, USA: 2-bromo-4-fluorobenzylamine hydrochloride; 2-bromo-5-fluorobenzylamine; 2-iodobenzylamine.

From Beta Pharma, Inc., New Haven, Conn. 06511, USA: 2,3,5-trichlorobenzylamine; 2,3,6-trichlorobenzylamine; 3,5-dibromobenzylamine; 3-bromo-5-fluorobenzylamine hydrochloride.

From Enamine, Kiev 01103, Ukraine: 1-(5-bromo-2-fluorophenyl)methanamine.

From Fluorochem Ltd., Old Glossop, Derbyshire SK13 7RY, United Kingdom: 5-chloro-2,4-difluorobenzylamine.

In addition to the amines of formula $HNR_3R_4$ where $R_3$ is hydrogen and $R_4$ is benzyl optionally substituted by halogen that are commercially available, many methods for the preparation of such amines are well known to one of ordinary skill in the art of organic synthesis. Many of these methods are enumerated in "The Chemistry of the Amino Group" [M. S. Gibson; S. Patai Ed.; John Wiley & Sons, Ltd. London 1968, 37-77], in "Advanced Organic Chemistry" [J. March, $3^{rd}$ Edition, John Wiley & Sons, Inc. New York, 1985], on pages 1153-1154, and in "Comprehensive Organic Transformations: A Guide to Functional Group Preparations" [R. C. Larock, VCH Publishers, Inc. New York, 1989] on pages 1061-1063.

One example of a method that can be used to prepare amines of formula $HNR_3R_4$ where $R_3$ is hydrogen and $R_4$ is benzyl optionally substituted by halogen (provided that the halogen is stable to the reaction conditions) is catalytic hydrogenation of benzonitriles. According to this process, the nitrile of formula ArCN where the aryl group Ar represents the aromatic portion of the benzyl group $R_4$, is treated with hydrogen in the presence of a noble metal catalyst such as palladium, nickel or cobalt, in an inert solvent such as ethanol at about room temperature. Exact conditions for carrying out such as reaction can be found in the literature, for example in L. Hegedus et al. *Appl. Catal. A.* 2005, 296, 209-215; or in F. E. Gould et al. *J. Org. Chem.* 1960, 25, 1658-1660.

Alternatively, the reduction of the nitrile of formula ArCN where the aryl group Ar represents the aromatic portion of the benzyl group $R_4$ may be carried out at elevated hydrogen pressure such as at about 50 bar in the presence of a homogeneous catalyst such as a mixture of bis(2-methylallyl)-1,5-cyclooctadieneruthenium(II), 1,1-bis(diphenylphosphino)ferrocene, and potassium tert-butoxide in toluene at about 80° C. using conditions similar to those disclosed in S. Enthaler et al. *Chem. Eur. J.* 2008, 14, 9491-9494.

As a further alternative, the reduction of the nitrile of formula ArCN where the aryl group Ar represents the aromatic portion of the benzyl group $R_4$ may be carried out by treating the nitrile with diisopropylaminoborane in the presence of catalytic amounts of lithium borohydride in an inert solvent such as tetrahydrofuran at a temperature about room temperature, using conditions similar to those disclosed in D. Haddenham et al. *J. Org. Chem.* 2009, 74, 1964-1970.

An example of a different method that can be used to prepare amines of formula $HNR_3R_4$ where $R_3$ is hydrogen and $R_4$ is benzyl optionally substituted by halogen is the conversion of a benzyl halide to a benzyl azide, followed by reduction of the azide to give the benzylamine. According to this process, the benzyl halide of formula $R_4X$ where X represents a leaving group such as a halide (for example, bromine, chlorine, iodine), alkyl or aryl sulfonate ester (for example, methane sulfonate or toluene sulfonate) is reacted with an alkali metal azide salt such as sodium azide in an inert solvent such as dimethylsulfoxide or ethanol at between about room temperature and about 80° C. Exact conditions for carrying out such as reaction can be found in the literature, for example in Y. Zhao et al. *Bioorg. Med. Chem.* 2008, 16, 6333-6337 (supplementary material); in M. Compain-Batissou et al. *Heterocycles* 2007, 71, 27-38; or in F. Tegtmeier et al. US 20080044354. The resulting azide group can be reduced using conditions that are similar to those described above for the preparation of an amine of formula $HNR_3R_4$ where $R_3$ is hydrogen and $R_4$ is cycloalkyl.

A number of amines of formula $HNR_3R_4$ where $R_3$ and $R_4$, together with the nitrogen atom to which they are attached, form piperidinyl substituted with one or more substituents independently selected from the group consisting of hydroxyl and phenyl optionally substituted with halogen are commercially available and examples are shown below.

From Sigma-Aldrich Corporation, Saint Louis, Mo. 63178, USA: piperidine; 4-hydroxypiperidine; 4-(4-chlorophenyl)-4-hydroxypiperidine; 3-hydroxypiperidine; 4-phenylpiperidine; 4-(4-bromophenyl)-4-piperidinol; 4-hydroxy-4-phenylpiperidine; (R)-3-hydroxypiperidine hydrochloride; (S)-3-hydroxypiperidine hydrochloride.

From Matrix Scientific, Columbia, S.C. 29224-5067, USA: 2-phenylpiperidine; 3-phenylpiperidine; 4-(3-fluorophenyl)-piperidine hydrochloride; 4-(4-fluoro-phenyl)-piperidine hydrochloride; 4-(4-fluorophenyl)-4-hydroxypiperidine; 4,4-diphenylpiperidine hydrochloride; 3-phenylpiperidine hydrochloride; 2-phenylpiperidine hydrochloride; 4-(2-fluorophenyl)piperidine hydrochloride; 3-(4-fluorophenyl)piperidine hydrochloride; 3-(3-fluorophenyl)piperidine hydrochloride; 3-(2-fluorophenyl)piperidine hydrochloride; 2-(4-fluorophenyl)piperidine; 2-(2-fluorophenyl)piperidine; 4-(2-fluoro-phenyl)-piperidin-4-ol.

From Oakwood Products, Inc., West Columbia, S.C., USA: 4-(4-chloro-phenyl)-piperidine hydrochloride; 4-(3-chlorophenyl)piperidine hydrochloride; 4-(4'-bromophenyl)piperidine; 4-(3-fluoro-phenyl)-piperidine; 4-(3,5-dichlorophenyl)-piperidine; 4-(2,4-difluorophenyl)piperidine; (S)-3-phenyl piperidine; 4-(4-fluoro-phenyl)-piperidin-4-ol hydrochloride; 4-(3,5-difluorophenyl)piperidine hydrochloride; 3-hydroxy-3-phenyl-piperidine; 4-(4-bromo-phenyl)-piperidine hydrochloride; 4-(3-bromo-phenyl)-piperidine hydrochloride From UkrOrgSynthesis, Kiev, 01133, Ukraine: 4-(4-fluorophenyl)piperidine; 4-(2-fluorophenyl)piperidine; 2-(3-fluorophenyl)piperidine; 4-(3,5-difluorophenyl)piperidine; 2-(2,4-difluorophenyl)piperidine; 2-(2,5-difluorophenyl)piperidine; 4-(3,4-difluorophenyl)piperidine; 2-(2,6-difluorophenyl)piperidine; 2-(3,4-difluorophenyl)piperidine; 4-(2,6-difluorophenyl)piperidine; 4-(2,5-difluorophenyl)piperidine.

From Chem-Impex International, Inc., Wood Dale, Ill. 60191, USA: 2-(4-chlorophenyl)piperidine hydrochloride; 4-(4-chlorophenyl)-4-phenylpiperidine hydrochloride; 3,3-diphenylpiperidine hydrochloride; 4-phenylpiperidine hydrochloride; 2-(4-fluorophenyl)piperidine hydrochloride; 2-(4-bromo-phenyl)-piperidine; 4-(4-fluorophenyl)-4-phenylpiperidine hydrochloride.

From 3B Scientific Corporation, Libertyville, Ill. 60048, USA: 4-(4-chlorophenyl)piperidine; 4-(2-chloro-phenyl)-piperidine hydrochloride; 4-(3,4-difluoro-phenyl)-piperidine hydrochloride; 1,5-dideoxy-1,5-imino-xylitol.

From Allichem LLC, Savage, Md., 20763-9504, USA: 4-(3-bromo-phenyl)-piperidine; 4-(3-chlorophenyl)piperidine.

From Beta Pharma, Inc., New Haven, Conn. 06511, USA: 4,4-diphenylpiperidine; 4-(4-bromophenyl)-4-(4-chlorophenyl)piperidine; 4,4-bis(4-chlorophenyl)piperidine.

From ChemBridge Corporation, San Diego, Calif. 92127, USA: 3-(4-chlorophenyl)piperidine.

In addition to the commercially available compounds of formula $HNR_3R_4$ where $R_3$ and $R_4$, together with the nitrogen atom to which they are attached, form piperidinyl substituted at the 4-position with a hydroxy group and a phenyl group optionally substituted with halogen mentioned above, further compounds of this type can be prepared using reactions that are well known in the field of organic synthesis.

For example, such a compound can be prepared by treating an aryl bromide with magnesium metal in ether at about room temperature to give the corresponding Grignard reagent or else with n-butyllithium in tetrahydrofuran at about −78° C. to give the corresponding organolithium reagent, either of which may then be treated with 1-tert-butoxycarbonyl-4-piperidone in the same solvent between about −78° C. and about room temperature to give the alcohol of formula 39. Exact conditions for carrying out such a reaction can be found in the literature, for example in M. Tomishima et al. *Bioorg. Med. Chem. Lett.* 2008, 18, 2886-2890; in C. Sonesson et al. US 20080269286; in G. Chang et al. US 20070213371; or in G. Chiu et al. US 20060217419. The tert-butoxycarbonyl protective group may then be removed in the usual fashion for example, either by treating it with HCl in dioxane, or with trifluoroacetic acid in dichloromethane at about room temperature to give the desired piperidine. Exact conditions for carrying out such as reaction can be found in the literature, for example in P. Zhang et al. US 20070088036; in Y. Jiang et al. *J. Med. Chem.* 2007, 50, 3870-3882; in C. Zhi et al. *J. Med. Chem.* 2005, 48, 7063-7074; and in G. Chiu et al. *Bioorg. Med. Chem. Lett.* 2007, 17, 3930-3934.

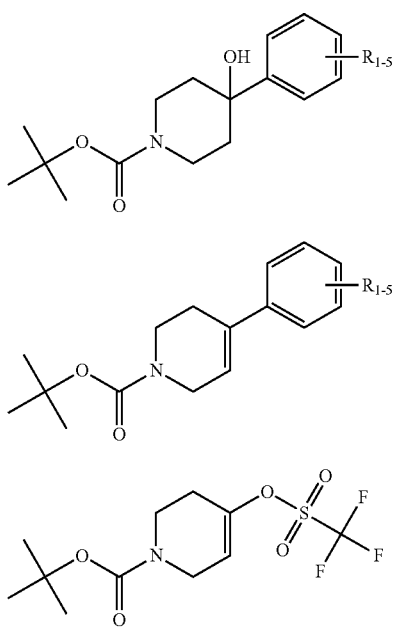

A compound of formula $HNR_3R_4$ where $R_3$ and $R_4$, together with the nitrogen atom to which they are attached, form piperidinyl substituted at the 4-position with a phenyl group optionally substituted with halogen can be prepared using reactions that are well known in the field of organic synthesis. For example, such a compound can be prepared from a compound of formula 39 by sequential dehydration, reduction, and removal of the tert-butoxycarbonyl protective group. The dehydration reaction may be effected by treating the compound of formula 39 with methanesulfonyl chloride and triethylamine in dichloromethane at a temperature of about −78° C. to give the compound of formula 40. The hydrogenation of the compound of formula 40 may be effected by treating the resulting olefin with hydrogen in the presence of a noble metal catalyst such as palladium-on-carbon in an inert solvent such as ethanol or ethyl acetate at a hydrogen pressure between about 14 psi and about 50 psi at about room temperature. Finally, the removal of the tert-butoxycarbonyl protective group may be effected as described in the paragraph above. Exact conditions for carrying out such as reaction sequence can be found in the literature, for example in G. Chiu et al. *Bioorg. Med. Chem. Lett.* 2007, 17, 3930-3934.

The compound of formula 40 may also be prepared by converting 1-tert-butoxycarbonyl-4-piperidone to the triflate derivative of formula 41. This reaction may be conveniently carried out as described in Receveur, J.-M. et al US 20090062317 where 1-tert-butoxycarbonyl-4-piperidone is added to a solution of lithium diisopropylamide in tetrahydrofuran at −78° C. for 30 minutes, adding N-phenyl-triflimide and stirring overnight. The resulting compound of formula 41 may then be reacted with one of a number of phenylboronic acids to give the compound of formula 40. This reaction, known to one of average skill in the art of organic synthesis as the Suzuki reaction, may be carried out by treating the triflate derivative of formula 41 with the phenylboronic acid in the presence of a catalyst such as tetrakis(triphenylphosphine)palladium(0) or bis(triphenylphosphine)palladium(II)dichloride, a base such as potassium carbonate in an inert solvent such as dimethoxyethane or dioxane, at a temperature about 80° C. Exact conditions for carrying out such as reaction can be found in the literature, for example in Receveur, J.-M. et al US 20090062317; in J. M. Goss and S. E. Schaus *J. Org. Chem.* 2008, 73, 7651-7656; or in M. R. Dobler et al. US 20080255149.

The present invention relates also to a composition and a unit dose formulation comprising the compound of the present invention. The composition and unit dose formulation comprise a therapeutically-effective amount of the compound of the present invention and a carrier. The compositions and unit dose formulation may also comprise additional accessory ingredients, for example, other excipients. Generally, from about 1 to about 99 percent of the composition or unit dose formulation consists of the compound of the present invention, preferably from about 5 to about 70 percent, and most preferably from about 10 to about 30 percent.

Lactose, corn starch or derivatives thereof, talc, stearic acids or its salts and the like can be used, for example, as carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance, no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The composition and unit dose formulation of the present invention can also comprise additional excipients, for example, preservatives, solubilizers, stabilizers, wetting agents, emulsifiers, sweeteners, colorants, flavorants, salts for use in varying osmotic pressure, buffers, masking agents, and antioxidants.

The composition and unit dose formulation of the present invention can also comprise additional therapeutically active agents.

Unit dose formulations of the present invention include those suitable for oral, nasal, topical (including buccal and sublingual), rectal, vaginal and/or parenteral administration. The formulation may be prepared by any method well known in the art of pharmacy.

Unit dose formulations of the present invention which are suitable for oral administration may be in the form of capsules, cachets, sachets, pills, tablets, lozenges (using a flavored basis, usually sucrose and acacia or tragacanth), powders, granules, elixirs, syrups, pastilles (using an inert base, such as gelatin and glycerin, or sucrose and acacia), mouth washes, and the like. The formulation may also be a solution or a suspension of the compound of the present invention in an aqueous or non-aqueous liquid. The formulation may also be an oil-in-water or water-in-oil liquid emulsion. The compound of the present invention may also be administered as a bolus, electuary or paste.

The present invention relates also to methods for preparing the composition and unit dose formulation of the present invention. Such methods comprise the step of bringing a compound of the present invention into association with a carrier and, optionally, one or more accessory ingredients. In general, the compositions and formulations of the present invention are prepared by uniformly and intimately bringing into association a compound of the present invention with a liquid carrier, a finely divided solid carrier, or both, and then, if necessary, shaping the product.

The present invention relates also to a method for treating a patient suffering from a proliferative disorder comprising the step of administering a compound of the present invention to the patient. The compound may be contained in a composition or unit dose formulation. In a preferred embodiment, the proliferative disorder is a solid tumor. In an especially preferred embodiment, the proliferative disorder is selected from the group consisting of breast tumor, lung tumor, colon tumor, and prostate tumor.

The following examples and references are provided to aid the understanding of the present invention, the true scope of which is set forth in the appended claims.

EXAMPLES

Reagents were purchased from Aldrich, Sigma, Maybridge, Advanced ChemTech, and Lancaster or other suppliers as indicated below and used without further purification. LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3 u 120 Å (3.2×30 mm) column cartridge; Mobile Phase A: Water (0.02% TFA) and Phase B: Acetonitrile (0.02% TFA); gradient 10% B to 90% B in 3-7 minutes; equilibration time of 1 minute; flow rate of 2 mL/minute.

Super critical fluid chromatography separations were performed using a Mettler-Toledo Minigram system with the following typical conditions: 100 bar, 30° C., 2.0 mL/min eluting a 12 mm AD column with 40% methanol in super critical fluid $CO_2$. In the case of analytes with basic amino groups, 0.2% isopropyl amine was added to the methanol modifier.

Preparation of Preferred Synthetic Intermediates

Intermediate 1

1,1-Dioxo-isothiazolidine-3-carboxylic acid methyl ester

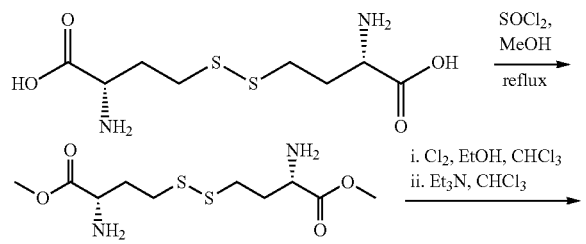

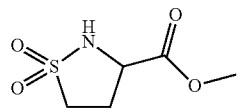

Step 1: (S)-2-Amino-4-((S)-3-amino-3-methoxycarbonyl-propyldisulfanyl)-butyric acid methyl ester. Thionyl chloride (0.5 mL, 8.20 mmol) was slowly added to a stirred solution of (S)-2-amino-4-((S)-3-amino-3-carboxy-propyldisulfanyl)-butyric acid (available from 3B Scientific Corporation, Libertyville, Ill. 60048, USA; 1.0 g, 3.73 mmol) in methanol (12.5 mL) at 0° C. The mixture was then subjected to reflux for 3 h, during which time the reaction went to completion (monitored by silica TLC). The reaction mixture was cooled to room temperature and solvent was distilled off under reduced pressure to give crude (S)-2-amino-4-((S)-3-amino-3-methoxycarbonyl-propyldisulfanyl)-butyric acid methyl ester (1.0 g, 90%) as white solid, which was carried on to the next step without further purification.

Step 2: 1,1-Dioxo-1$\lambda^6$-isothiazolidine-3-carboxylic acid methyl ester

A stream of chlorine was bubbled through a cooled solution of (S)-2-amino-4-((S)-3-amino-3-methoxycarbonyl-propyldisulfanyl)-butyric acid methyl ester (0.50 g, 1.68 mmol) in ethanol/chloroform (1:2, 15 mL) at 0° C. for 1 h. The solvent was distilled off under reduced pressure and the residue was left under high vacuum for 4 h. The residue was then diluted with chloroform (5 mL), cooled to −5° C., and triethylamine (1.4 mL, 9.88 mmol) was added dropwise at the same temperature. The reaction temperature was brought to room temperature and the mixture was stirred for 1 h. Solvents were distilled off in vacuo and the crude product was purified by silica gel column chromatography (100-200 mesh) using a gradient of 1-2% methanol/dichloromethane to give pure 1,1-dioxo-1$\lambda^6$-isothiazolidine-3-carboxylic acid methyl ester (0.250 g, 41%).

Intermediate 2

2-Benzyl-1,1-dioxo-1-$\lambda^6$-isothiazolidine-3-carboxylic acid

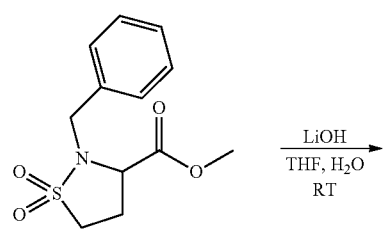

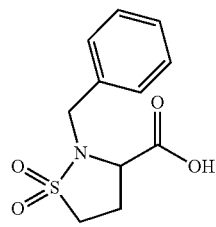

Step 1: To a stirring solution of 1,1-dioxo-1λ$^6$-isothiazolidine-3-carboxylic acid methyl ester (Intermediate 1, 0.200 g, 1.1 mmol) in N,N-dimethylformamide (5 mL) was added potassium carbonate (0.450 g, 3.2 mmol) at 0° C. After 10 min of stirring at the same temperature, benzyl chloride (0.153 g, 1.2 mmol) was added followed by tetra-n-butylammonium iodide (0.40 g, 1.1 mmol). After 5 h stirring at room temperature, the reaction mixture was diluted with ethyl acetate (25 mL) and washed with water (3×15 mL). The organic phase was dried over anhydrous sodium sulfate, and concentrated under reduced pressure to provide crude material, which was purified by silica gel column chromatography (100-200 mesh) to provide 2-benzyl-1,1-dioxo-1-λ$^6$-isothiazolidine-3-carboxylic acid methyl ester (0.170 g, 56%). FIA-MS (+1 mode): m/z=270 [M+1].

Step 2: To a stirred solution of 2-benzyl-1,1-dioxo-1-λ$^6$-isothiazolidine-3-carboxylic acid methyl ester (0.600 g, 2.23 mmol) in tetrahydrofuran-water (5:1, 20 mL) was added lithium hydroxide monohydrate (0.140 g, 3.3 mmol) at room temperature. After overnight stirring at the same temperature, the reaction mixture was acidified with 2N hydrochloric acid (pH~3), extracted with ethyl acetate (3×25 mL). The combined organic parts were washed with water, dried over anhydrous sodium sulfate and concentrated under reduced pressure to provide 2-benzyl-1,1-dioxo-1-λ$^6$-isothiazolidine-3-carboxylic acid (0.420 g, 74%) as a crude product, which was carried on to the next step without further purification. FIA-MS (+1 mode): m/z=254 [M+1].

Intermediate 3

(S)-4,4,N1,N1-Tetramethyl-pentane-1,2-diamine hydrochloride salt

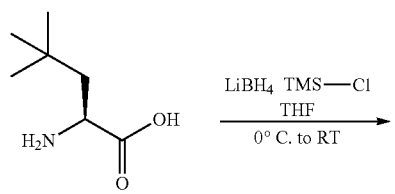

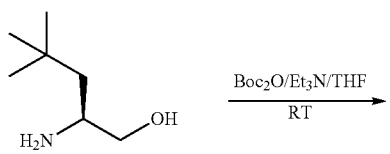

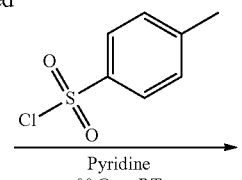

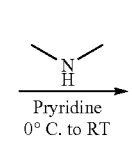

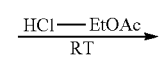

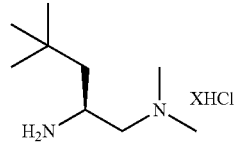

Step 1: (S)-2-Amino-4,4-dimethyl-pentan-1-ol

To a stirred suspension of lithium borohydride (0.75 g, 34.4 mmol, 2.0 equiv.) in tetrahydrofuran (60 mL) was added trimethylsilyl chloride (7.48 g, 68.85 mmol, 4.0 equiv.) slowly over a period of 5 minutes at 0° C. under argon. To the reaction mixture was added (S)-2-amino-4,4-dimethyl-pentanoic acid (available from Chem-Impex International, Inc., Wood Dale, Ill., USA; 2.50 g, 17.2 mmol, 1.0 equiv.) in portions over a span of 10 minutes at the same temperature and the reaction was allowed to stir for 24 hours at room temperature. The reaction mixture was quenched with the slow addition of methanol (50 mL) at 0° C., and volatiles were removed by vacuum distillation. The obtained residue was treated with an aqueous solution of 20% potassium hydroxide (w/v; 10 mL) and extracted with dichloromethane (3×20 mL). The combined organic phases were dried over anhydrous sodium sulfate and concentrated under reduced pressure to give (S)-2-amino-4,4-dimethyl-pentan-1-ol (1.9 g, 84%).

Step 2: ((S)-1-Hydroxymethyl-3,3-dimethyl-butyl)-carbamic acid tert-butyl ester

To a stirred solution of (S)-2-amino-4,4-dimethyl-pentan-1-ol (2.0 g, 15.2 mmol, 1.0 equiv.) and triethylamine (1.85 g, 18.3 mmol, 1.2 equiv.) in dry tetrahydrofuran (50 mL) was added di-tert-butyl dicarbonate (3.99 g, 18.3 mmol, 1.2 equiv.) slowly at 0° C. under nitrogen. After 4 hours of stirring at room temperature, the tetrahydrofuran was distilled off under reduced pressure and the crude reaction mixture was purified by silica gel column chromatography (100-200 mesh) using a gradient of 10-25% ethyl acetate/hexanes to give ((S)-1-hydroxymethyl-3,3-dimethyl-butyl)-carbamic acid tert-butyl ester (2.8 g, 79%).

Step 3: Toluene-4-sulfonic acid(S)-2-tert-butoxycarbonylamino-4,4-dimethyl-pentyl ester To a stirred solution of ((S)-1-hydroxymethyl-3,3-dimethyl-butyl)-carbamic acid tert-butyl ester (3.0 g, 13.0 mmol, 1.0 equiv.) in dry pyridine (14.8 mL) was added tosyl chloride (3.7 g, 19.4 mmol, 1.5 equiv) portionwise at 0° C. under nitrogen. After 4 hours of stirring at room temperature, the reaction mixture was extracted with ethyl acetate (200 mL), washed with water (3×200 mL) followed by brine (2×100 mL), and dried over anhydrous sodium sulfate to give a crude residue. The residue was purified by silica gel column chromatography (100-200 mesh) using a gradient of 5-10% ethyl acetate/hexanes to give toluene-4-sulfonic acid(S)-2-tert-butoxycarbonylamino-4,4-dimethyl-pentyl ester (3 g, 60%).

Step 4: ((S)-1-Dimethylaminomethyl-3,3-dimethyl-butyl)-carbamic acid tert-butyl ester Dimethylamine (11.2 g, 249.3 mmol, 30.0 equiv) was added portionwise to a stirred solution of toluene-4-sulfonic acid (S)-2-tert-butoxycarbonylamino-4,4-dimethyl-pentyl ester (3.2 g, 8.31 mmol, 1.0 equiv.) in pyridine (9.6 mL) at 0° C. The reaction mixture was slowly warmed to room temperature and stirred for an additional 20 hours at the same temperature. The reaction mixture was diluted with the addition of an aqueous solution of 10% potassium hydroxide (w/v; 30 mL) and was extracted with dichloromethane (3×150 mL). The collected organic extracts were dried over anhydrous sodium sulfate, concentrated under reduced pressure to obtain a crude mass. This was purified by purified by silica gel column chromatography (100-200 mesh) using a gradient of 2-5% methanol/dichloromethane to give ((S)-1-dimethylaminomethyl-3,3-dimethyl-butyl)-carbamic acid tert-butyl ester (1.4 g, 65%).

Step 5: (S)-4,4,N1,N1-Tetramethyl-pentane-1,2-diamine hydrochloride salt

A solution of ((S)-1-dimethylaminomethyl-3,3-dimethyl-butyl)-carbamic acid tert-butyl ester (1.6 g, 6.20 mmol, 1.0 equiv.) in dry HCl-ethyl acetate (31 mL) was stirred overnight at room temperature under nitrogen. Ethyl acetate was distilled off under reduced pressure to give crude (S)-4,4,N1,N1-tetramethyl-pentane-1,2-diamine hydrochloride salt (1.4 g) as a white solid.

Intermediate 4

6-Chloro-2-fluoro-3-methoxy-benzaldehyde

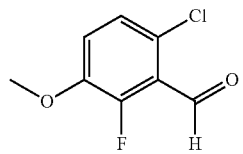

A solution of 4-chloro-2-fluoro-1-methoxy-benzene (Aldrich; 10.2 g, 63.5 mmol) in dry tetrahydrofuran (500 mL) was cooled to −78° C. under a nitrogen atmosphere. A solution of lithium diisopropylamide (1.8 M in tetrahydrofuran/heptane/ethylbenzene, 39.9 mL, 70.2 mmol) was added dropwise by syringe. The reaction mixture was warmed to −55° C. and held at this temperature for 1 h. The mixture was then cooled again to −78° C., and dry N,N-dimethylformamide (10.7 mL, 139 mmol) was added by syringe. The cooling bath was removed and the reaction was allowed to warm to −10° C. and quenched by the addition of ice flakes (~200 mL) and a solution of saturated ammonium chloride (200 mL). Ethyl acetate (200 mL) was added, the layers were separated and the aqueous later was extracted with ethyl acetate (200 mL). The combined organic layers were washed with brine, dried over sodium sulfate, filtered, evaporated, and purified by silica gel chromatography, eluting with 0-30% ethyl acetate/hexanes to give 6-chloro-2-fluoro-3-methoxy-benzaldehyde (5.6 g, 47% yield) as an oil that solidified upon standing.

Intermediate 5

2-(3-Formyl-benzyl)-1,1-dioxo-1$\lambda^6$ isothiazolidine-3-carboxylic acid ethyl ester

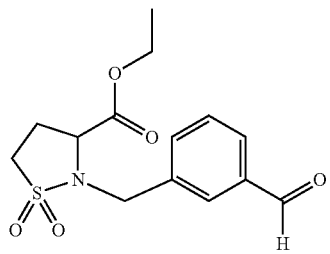

Step 1: 3-Bromomethyl-benzaldehyde

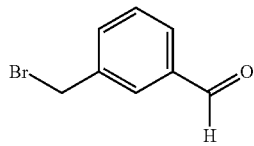

A solution of 3-cyanobenzyl bromide (available from Aldrich; 10.1 g, 51.5 mmol) in chlorobenzene (100 mL) was cooled in an ice-water bath. A solution of diisobutylaluminum hydride in hexanes (available from Aldrich; 1 M; 65 mL, 65 mmol) was added over 25 minutes, and the reaction mixture was stirred below 5° C. for 1 h. Chloroform (100 mL) was added, followed by 10% aqueous hydrochloric acid (dropwise). The layers were separated and the organic layer was washed with water. Each aqueous layer was back extracted with chloroform, and the organic phases were combined, dried over sodium sulfate, filtered, evaporated and purified by chromatography, eluting with 0-40% ethyl acetate/hexanes to give pure fractions and a number of impure fractions. The impure fractions were chromatographed a second time, eluting with 0-27% ethyl acetate/hexanes. Fractions homogeneous for the product from the two chromatographic separations were combined and concentrated. The residue was dissolved in ether and layered with hexane. The mixture was chilled overnight and the solid was filtered off, washed with hexane and dried under high vacuum at room temperature to give 3-bromomethyl-benzaldehyde (7.32 g, 71%).

Step 2: 2-(3-Formyl-benzyl)-1,1-dioxo-1λ⁶ isothiazolidine-3-carboxylic acid ethyl ester

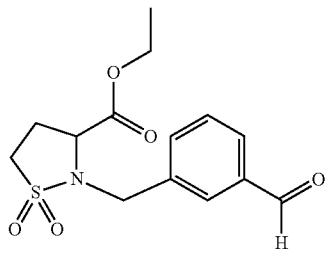

3-Bromomethyl-benzaldehyde (2.44 g, 12.3 mmol) and cesium carbonate (9.08 g, 27.9 mmol) were added to a solution of a 4:3 mixture of 1,1-dioxo-isothiazolidine-3-carboxylic acid methyl ester and 1,1-dioxo-isothiazolidine-3-carboxylic acid ethyl ester (Intermediate 7 Step 2; 2.01 g, 10.8 mmol) in N,N-dimethylformamide (60 mL). The mixture was stirred at room temperature for 20 h and then dichloromethane (100 mL) was added. Saturated aqueous ammonium chloride solution (25 mL) was added followed by 1 M hydrochloric acid to bring the pH to 2-3. The two layers were separated and the organic layer was washed twice with brine. The solution was dried over sodium sulfate, and filtered. Celite was added and the solvents were evaporated under reduced pressure. The residue (containing the mixture of crude products coated onto Celite) was purified using flash chromatography (Analogix SF40-240 g Si), eluting with 30-70% ethyl acetate/hexanes to give 2-(3-formyl-benzyl)-1,1-dioxo-1λ⁶ isothiazolidine-3-carboxylic acid ethyl ester (first eluting peak; 1.26 g, 37%) and 2-(3-formyl-benzyl)-1,1-dioxo-1λ⁶ isothiazolidine-3-carboxylic acid methyl ester (second eluting peak; 1.69 g, 53%).

Intermediate 6

2-{3-[((S)-1-Dimethylaminomethyl-2-phenyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide

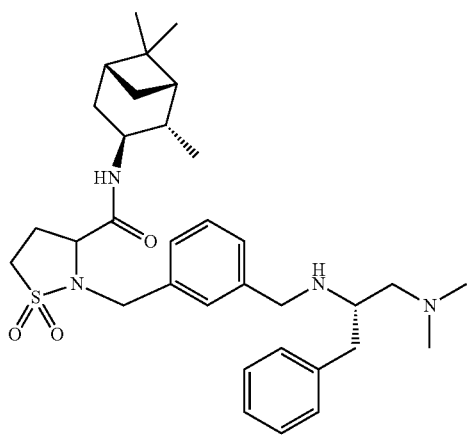

Step 1: ((S)-1-Dimethylcarbamoyl-2-phenyl-ethyl)-carbamic acid tert-butyl ester

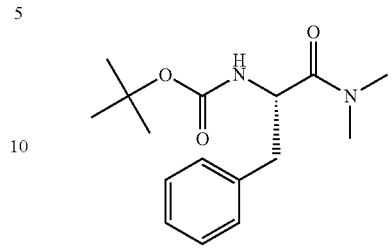

To a cooled solution of (S)-2-tert-butoxycarbonylamino-3-phenylpropionic acid (available from Aldrich; 5.3 g, 20 mmol) in dimethylformamide (50 mL) at 0° C. were added 1-hydroxybenzotriazole (available from 3B Scientific Corporation, Libertyville, Ill. 60048, USA; 2.97 g, 22 mmol) and O-benzotriazol-1-yl-N,N,N',N'-tetramethyluronium hexafluororophosphate (available from Aldrich; 8.30 g, 22 mmol). Diisopropylethylamine (10.7 mL, 61.4 mmol) and dimethylamine in tetrahydrofuran (2M, 15 mL, 30 mmol) were added dropwise. The mixture was stirred for 1 h at 0° C. and ethyl acetate was added. The mixture was washed with water and brine, and dried over sodium sulfate. Evaporation of the solvents gave ((S)-1-dimethylcarbamoyl-2-phenyl-ethyl)-carbamic acid tert-butyl ester as a yellow oil (5.52 g) which was used in the next step without further purification.

Step 2: (S)-2-Amino-N,N-dimethyl-3-phenyl-propionamide

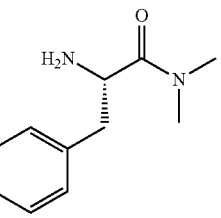

((S)-1-Dimethylcarbamoyl-2-phenyl-ethyl)-carbamic acid tert-butyl ester (2.0 g, 6.85 mmol) was dissolved in methylene chloride (20 mL) at 0° C. Trifluoroacetic acid (20 mL) was added. The mixture was stirred for 2 h and evaporated. The residue was dissolved in methylene chloride and very carefully basified using saturated aqueous sodium bicarbonate. The organic layer was separated and the aqueous layer was extracted using methylene chloride. The combined organic extracts were washed with water and brine, and then dried over sodium sulfate to give (S)-2-amino-N,N-dimethyl-3-phenyl-propionamide (1.0 g, 76%) as yellow oil.

Step 3: (S)—N1,N1-Dimethyl-3-phenyl-propane-1,2-diamine

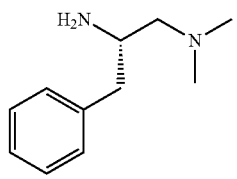

To a solution of (S)-2-amino-N,N-dimethyl-3-phenyl-propionamide (1.0 g, 5.2 mmol) in tetrahydrofuran (10 mL) was added a solution of lithium aluminum hydride in tetrahydrofuran and toluene (3.5 M, 7.4 mL, 26 mmol) dropwise. The mixture was heated to reflux for 4 h after addition and then cooled. Ether (20 mL) was added. Ethyl acetate was added dropwise until all the lithium aluminum hydride was consumed. Sodium hydroxide (1M, 20 mL) was added and the mixture was stirred for 30 min. The mixture was extracted three times with ether. The combined organic extracts were washed with brine, dried over sodium sulfate and evaporated to give (S)—N1,N1-dimethyl-3-phenyl-propane-1,2-diamine (0.60 g, 65%)

Step 4: 2-{3-[((S)-1-Dimethylaminomethyl-2-phenyl-ethylamino)-methyl]-benzyl}-1,1-dioxo-1λ$^6$-isothiazolidine-3-carboxylic acid ethyl ester

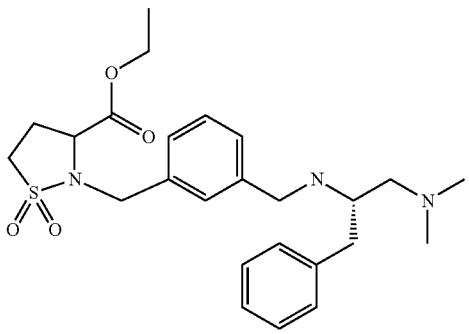

To a solution of (S)—N,N'-dimethyl-3-phenyl-propane-1,2-diamine (120 mg, 0.673 mmol) in methanol (2 mL) under argon was added a solution of 2-(3-formyl-benzyl)-1,1-dioxo-1λ$^6$-isothiazolidine-3-carboxylic acid ethyl ester (Intermediate 4; 230.5 mg, 0.740 mmol) in methanol (4 mL). The solution was cooled 0° C. in an ice bath and to this was added sodium cyanoborohydride (63.4 mg, 1.01 mmol) and acetic acid (0.3 mL). The solution was allowed to warm to room temperature and stirred for 16 h under argon. The reaction mixture was diluted with ethyl acetate (50 mL), washed with water (2×10 mL) and the aqueous layer was extracted with ethyl acetate (50 mL). The combined organics were dried over sodium sulfate, filtered and concentrated to give crude 2-{3-[((S)-1-dimethylaminomethyl-2-phenyl-ethylamino)-methyl]-benzyl}-1,1-dioxo-1λ$^6$-isothiazolidine-3-carboxylic acid ethyl ester (360 mg) as colorless oil.

Step 5: 2-{3-[((S)-1-Dimethylaminomethyl-2-phenyl-ethylamino)-methyl]-benzyl}-1,1-dioxo-1λ$^6$-isothiazolidine-3-carboxylic acid

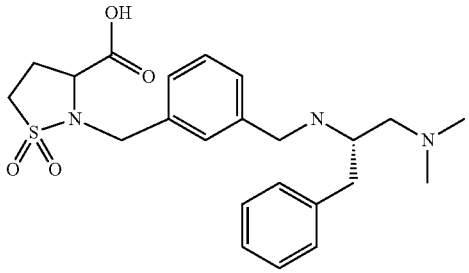

To a solution of crude 2-{3-[((S)-1-dimethylaminomethyl-2-phenyl-ethylamino)-methyl]-benzyl}-1,1-dioxo-1λ$^6$-isothiazolidine-3-carboxylic acid ethyl ester (360 mg, approx. 0.67 mmol) in tetrahydrofuran (4 mL) was added lithium hydroxide hydrate (57.4 mg, 1.37 mmol) followed by water (1 mL). It was stirred at room temperature for 2 h. To the stirred solution was added ~15 drops 1N hydrochloric acid to bring the pH to 4.5. The sample was concentrated to dryness and dried over phosphorus pentoxide overnight. The crude 2-{3-[((S)-1-dimethylaminomethyl-2-phenyl-ethylamino)-methyl]-benzyl}-1,1-dioxo-1λ$^6$-isothiazolidine-3-carboxylic acid (350 mg, ca 80% pure) (LiCl present) was used in the next step.

Step 6: 2-{3-[((S)-1-Dimethylaminomethyl-2-phenyl-ethylamino)-methyl]-benzyl}-1,1-dioxo-1λ$^6$-isothiazolidine-3-carboxylic acid((1S,2S,3S,5R)-2,6,6-trimethyl-bicylo[3.1.1]hept-3-yl)amide

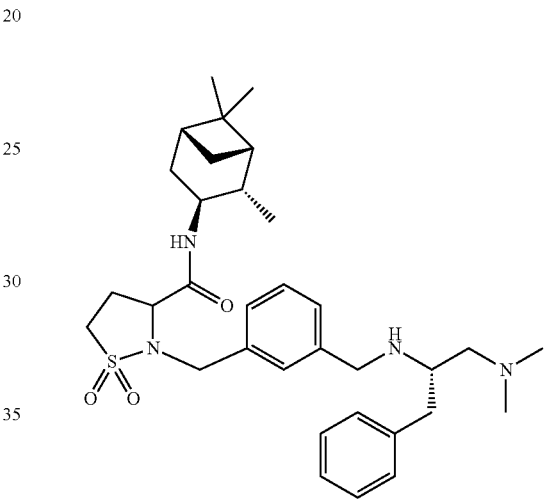

(+)-Isopinocampheylamine (Aldrich; 29 mg, 0.19 mmol), O-(benzotriazol-1-yl)-N,N,N',N'-tetramethyluronium tetrafluoroborate (available from Aldrich; 58.4 mg, 0.18 mmol), N-hydroxybenzotriazole (available from 3B Scientific Corporation, Libertyville, Ill. 60048, USA; 24.3 mg, 0.18 mmol) were added to a cooled (0° C.) solution of 2-{3-[((S)-1-dimethylaminomethyl-2-phenyl-ethylamino)-methyl]-benzyl}-1,1-dioxo-1λ$^6$-isothiazolidine-3-carboxylic acid (100 mg 80% pure, 0.18 mmol) in dry N,N-dimethylformamide (3 mL) under argon. N,N-Diisopropylethylamine (70 µL, 0.4 mmol) was then added. The solution was then stirred at room temperature. After 30 minutes more (+)-isopinocampheylamine (6 mg, 0.04 mmol), O-(benzotriazol-1-yl)-N,N,N',N'-tetramethyluronium tetrafluoroborate (available from Aldrich; 6 mg, 0.002 mmol) and N-hydroxybenzotriazole (available from 3B Scientific Corporation, Libertyville, Ill. 60048, USA; 3 mg, 0.002 mmol) were added. After 90 minutes all of the starting material had been consumed. The reaction mixture was diluted with ethyl acetate (50 mL) and washed with 1N NaOH (3×15 mL), and brine (20 mL). The organic phase was dried over sodium sulfate, filtered and concentrated to give the crude product (132 mg). This material was combined with the crude product from an identical experiment using 2-{3-[((S)-1-dimethylaminomethyl-2-phenyl-ethylamino)-methyl]-benzyl}-1,1-dioxo-1λ$^6$-isothiazolidine-3-carboxylic acid (250 mg). The combined lots were chromatographed, eluting with 0-10% methanol/dichloromethane to give 2-{3-[((S)-1-dimethylaminomethyl-2-phenyl-ethylamino)-methyl]-benzyl}-1,1-dioxo-1λ$^6$-isothiazolidine-3-carboxylic acid((1S,2S,3S,5R)-2,6,6-trimethyl-bicylo[3.1.1]hept-3-yl)amide (256 mg, 60%) as a tan foam.

Intermediate 7

2-{3-[((S)-1-Dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide

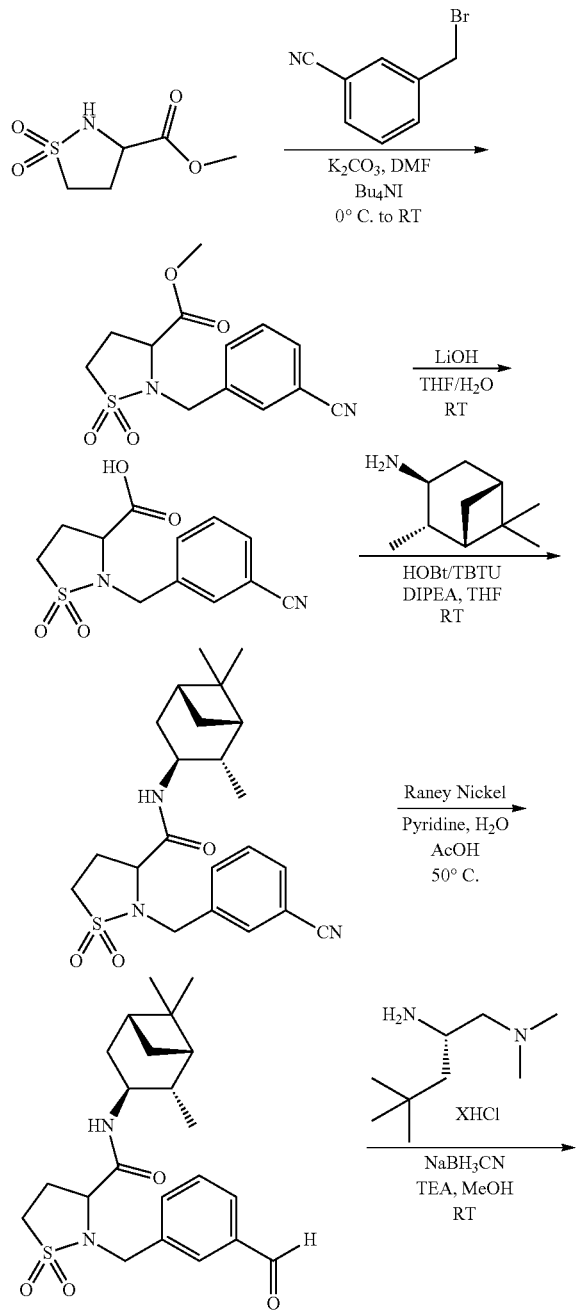

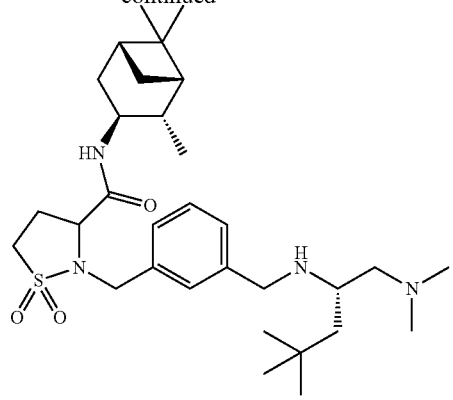

Step 1: 2-(3-Cyano-benzyl)-1,1-dioxo-1λ$^6$-isothiazolidine-3-carboxylic acid methyl ester To a stirred solution of 1,1-dioxo-1λ$^6$-isothiazolidine-3-carboxylic acid methyl ester (Intermediate 1, 0.200 g, 1.10 mmol) in N,N-dimethylformamide (5 mL) was added potassium carbonate (0.450 g, 3.20 mmol) at room temperature under nitrogen. The reaction mixture was cooled to 0° C. and 3-cyano benzyl bromide (available from Aldrich; 0.240 g, 1.22 mmol) was added into the reaction mixture slowly and followed by the addition of tetra-n-butylammonium (0.025 g, 0.07 mmol). The reaction was completed in 5 h at room temperature as monitored by silica TLC. The reaction mixture was diluted with ethyl acetate (25 mL), washed with water (3×15 mL), dried over sodium sulfate and concentrated under reduced pressure to provide crude material, which was purified by silica gel column chromatography (100-200 mesh) using a gradient of 20-30% ethyl acetate/hexanes to give 2-(3-cyano-benzyl)-1,1-dioxo-1λ$^6$-isothiazolidine-3-carboxylic acid methyl ester (0.170 g, 56%).

Step 2: 2-(3-Cyano-benzyl)-1,1-dioxo-1λ$^6$-isothiazolidine-3-carboxylic acid

To a stirred solution of 2-(3-cyano-benzyl)-1,1-dioxo-1λ$^6$-isothiazolidine-3-carboxylic acid methyl ester (6.0 g, 20.4 mmol) in a tetrahydrofuran-water mixture (4:1, 50 mL), lithium hydroxide monohydrate (2.5 g, 59.6 mmol) was added at room temperature and stirred at this temperature for 4 h. Then tetrahydrofuran was removed from the reaction mixture under reduced pressure. The residual reaction mixture was cooled to 0° C. and 1N hydrochloric acid was added to make the pH~2. The acidified reaction mixture was extracted with ethyl acetate (3×150 mL). The combined organic layers were washed with water (2×50 mL) followed by brine (50 mL) and then dried over sodium sulfate and concentrated under reduced pressure to provide 2-(3-cyano-benzyl)-1,1-dioxo-1λ$^6$-isothiazolidine-3-carboxylic acid (5.2 g, 91%).

Step 3: 2-(3-Cyano-benzyl)-1,1-dioxo-1λ$^6$-isothiazolidine-3-carboxylic acid ((1S,2S,3S,5R)-2,6,6-trimethyl-bicyclo[3.1.1]hept-3-yl)-amide To a stirred solution of 2-(3-cyano-benzyl)-1,1-dioxo-1λ$^6$-isothiazolidine-3-carboxylic acid (6.0 g, 21.4 mmol) in tetrahydrofuran (40 mL) was added 1-hydroxybenzotriazole (available from 3B Scientific Corporation, Libertyville, Ill. 60048, USA; 2.8 g, 20.72 mmol), TBTU (6.8 g, 21.18 mmol) and diisopropylethylamine (8.3 g, 64.21 mmol) simultaneously at room temperature. After 16 h of stirring at the same temperature, tetrahydrofuran was distilled off under reduced pressure. The obtained crude residue was extracted with ethyl acetate (120 mL), washed with an aqueous solution of 1N NaOH (50 mL), brine (50 mL), dried over anhydrous sodium sulfate and concentrated under reduced pressure to give a crude mass. The crude mass was purified by silica gel column chromatography (100-200 mesh) using a gradient of 50-70% ethyl acetate/hexanes to give 2-(3-cyano-benzyl)-1,1-dioxo-$1\lambda^6$-isothiazolidine-3-carboxylic acid((1S,2S,3S,5R)-2,6,6-trimethyl-bicyclo[3.1.1]hept-3-yl)-amide (7.0 g, 79.5%).

Step 4: 2-(3-Formyl-benzyl)-1,1-dioxo-$1\lambda^6$-isothiazolidine-3-carboxylic acid ((1S,2S,3S,5R)-2,6,6-trimethyl-bicyclo[3.1.1]hept-3-yl)-amide
To a stirred solution of 2-(3-cyano-benzyl)-1,1-dioxo-$1\lambda^6$-isothiazolidine-3-carboxylic acid ((1S,2S,3S,5R)-2,6,6-trimethyl-bicyclo[3.1.1]hept-3-yl)-amide (0.200 g, 0.48 mmol) in a mixture of pyridine-acetic acid-water (2:1:1; 7.2 mL) was added sodium hypophosphate hydrate (0.400 g, 3.77 mmol) at room temperature. The reaction mixture was cooled to 0° C. and Raney Nickel (0.200 g) was added under an argon atmosphere. After stirring at 0° C. for 10 min, the temperature was raised to 40-45° C. and the reaction mixture was stirred for an additional 2.5 h at the same temperature (with monitoring by silica TLC). The reaction mixture was cooled, filtered through a pad of celite and the residue was washed with methanol (5 mL). The combined filtrates were concentrated to provide the crude material, which was purified by silica gel column chromatography (100-200 mesh) using a gradient of 50-60% ethyl acetate/hexanes to give 2-(3-formyl-benzyl)-1,1-dioxo-$1\lambda^6$-isothiazolidine-3-carboxylic acid((1S,2S,3S,5R)-2,6,6-trimethyl-bicyclo[3.1.1]hept-3-yl)-amide (0.100 g, 49%).

Step 5: 2-{3-[((S)-1-Dimethylaminomethyl-3,3-dimethyl-butylamino)methyl]-benzyl}-1,1-dioxo-$1\lambda^6$-isothiazolidine-3-carboxylic acid((1S,2S,3S,5R)-2,6,6-trimethyl-bicyclo[3.1.1]hept-3-yl)-amide To a stirred solution of (S)-4,4,N1,N1-tetramethyl-pentane-1,2-diamine hydrochloride salt (Intermediate 2, 0.100 g, 0.43 mmol) in methanol (5 mL) at 0° C. was added triethylamine (0.12 g, 0.16 ml, 1.2 mmol). After 10 min of stirring at the same temperature, a solution of 2-(3-formyl-benzyl)-1,1-dioxo-$1\lambda^6$-isothiazolidine-3-carboxylic acid((1S,2S,3S,5R)-2,6,6-trimethyl-bicyclo[3.1.1]hept-3-yl)-amide (0.181 g, 0.43 mmol) in methanol (1 mL) was added and stirring was continued for an additional 15 min at room temperature. The reaction mixture was again brought into 0° C. and sodium cyanoborohydride (0.022 g, 0.35 mmol) and acetic acid (0.2 mL) were added simultaneously into the reaction mixture. After stirring overnight at room temperature, the reaction mixture was concentrated under reduced pressure, the residue was diluted with ethyl acetate (5 mL), washed with water (3 mL), dried over anhydrous sodium sulfate and concentrated under reduced pressure to provide crude 2-{3-[((S)-1-dimethylaminomethyl-3,3-dimethyl-butylamino)methyl]-benzyl}-1,1-dioxo-$1\lambda^6$-isothiazolidine-3-carboxylic acid((1S,2S,3S,5R)-2,6,6-trimethyl-bicyclo[3.1.1]hept-3-yl)-amide (0.216 g, 89%).

Intermediate 8

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-$1\lambda^6$-isothiazolidine-3-carboxylic acid

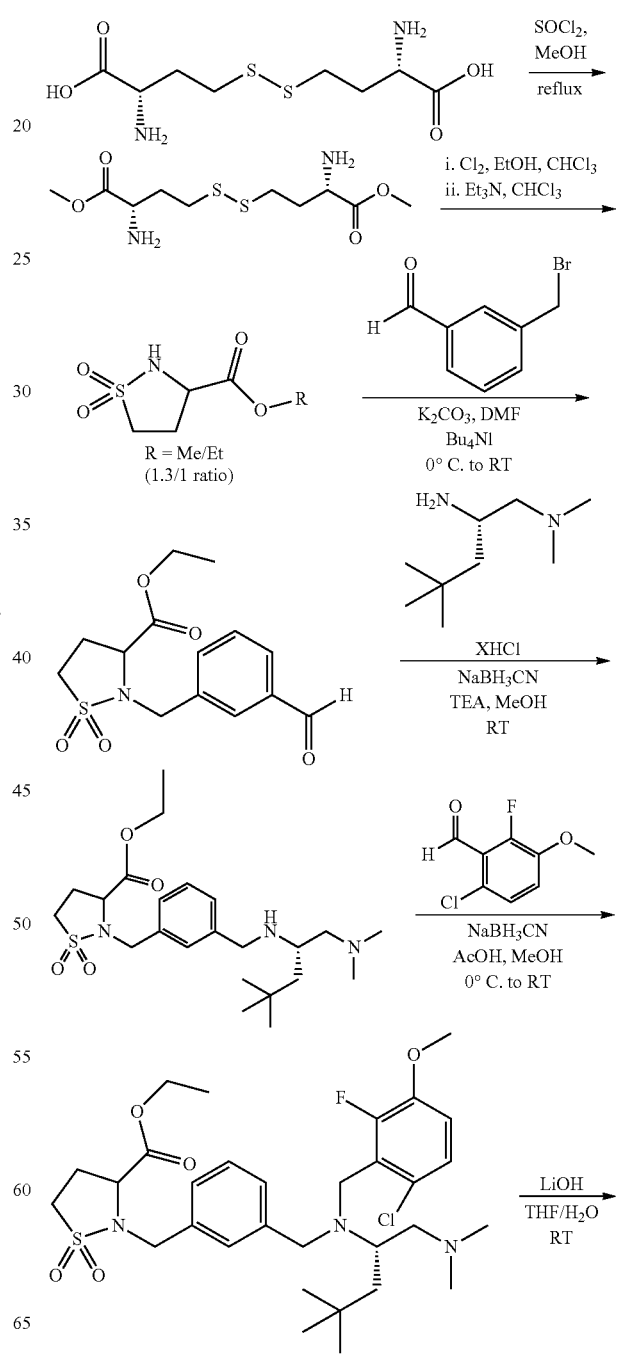

-continued

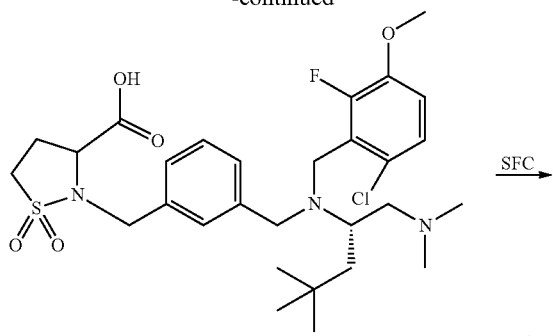

Step 1: (S)-2-Amino-4-((S)-3-amino-3-methoxycarbonyl-propyldisulfanyl)-butyric acid methyl ester To a stirred solution of (S)-2-Amino-4-((S)-3-amino-3-carboxy-propyldisulfanyl)-butyric acid (6.0 g, 22.3 mmol) in methanol (156 mL) at 0° C. thionyl chloride (6.5 mL, 89.5 mmol) was added slowly. The mixture was then stirred at room temperature overnight. The reaction mixture was concentrated under reduced pressure to provide crude (S)-2-amino-4-((S)-3-amino-3-methoxycarbonyl-propyldisulfanyl)-butyric acid methyl ester, which was carried on to the next step without further purification.

Step 2: 1,1-Dioxo-1λ⁶-isothiazolidine-3-carboxylic acid methyl ester and 1,1-Dioxo-1λ⁶-isothiazolidine-3-carboxylic acid ethyl ester To a cooled solution of (S)-2-amino-4-((S)-3-amino-3-methoxycarbonyl-propyldisulfanyl)-butyric acid methyl ester (crude material from Step 1, 22.3 mmol) in ethanol-chloroform (1:2, 135 mL) at 0° C., a stream of chlorine was bubbled through the reaction mixture for 1 h. The solvent was distilled off under reduced pressure and the crude material placed under high vacuum for 1 h. The resulting residue was diluted with chloroform (30 mL) and cooled to 0° C. Triethylamine (16 mL, 111.8 mmol) was added drop wise at the same temperature. The reaction temperature was brought to room temperature and stirred overnight. Solvents were concentrated in vacuo and the crude was carried on to the next step in the sequence as a mixture (1.3 to 1; methyl:ethyl) of the 1,1-dioxo-1λ⁶-isothiazolidine-3-carboxylic acid methyl and ethyl esters (6.4 g, 80%).

Step 3: 2-(3-Formyl-benzyl)-1,1-dioxo-1λ⁶-isothiazolidine-3-carboxylic acid ethyl ester To a stirred solution of a mixture (1.3 to 1; methyl:ethyl) of the 1,1-dioxo-1λ⁶-isothiazolidine-3-carboxylic acid methyl and ethyl esters 0.085 g, 0.45 mmol) in anhydrous N,N-dimethylformamide (2.5 mL) was added 3-bromomethyl-benzaldehyde (0.100 g, 0.50 mmol). The solution was stirred at room temperature under an argon atmosphere for 20 hours. The reaction was diluted with dichloromethane. Saturated ammonium chloride was added followed by hydrochloric acid (1.0 M) until the mixture reached a pH~2-3. The organic layer was separated, washed with brine, dried over anhydrous sodium sulfate and concentrated over celite. The product was purified by column chromatography on silica gel to provide 2-(3-formyl-benzyl)-1,1-dioxo-1λ⁶-isothiazolidine-3-carboxylic acid ethyl ester (0.053 g, 42%)

Step 4: 2-{3-[((S)-1-Dimethylaminomethyl-3,3-dimethyl-butylamino)-methyl]-benzyl}1,1-dioxo-1λ⁶-isothiazolidine-3-carboxylic acid ethyl ester To a stirred solution of (S)-4,4,N1,N1-tetramethyl-pentane-1,2-diamine hydrochloride salt (Intermediate 2, 0.921 g, 4.73 mmol) in methanol (10 mL) cooled in an ice bath (0° C.) was added triethylamine (2.19 mL, 15.7 mmol) and the solution was stirred at this temperature for 25 minutes. To this cooled solution was added 2-(3-formyl-benzyl)-1,1-dioxo-1λ⁶-isothiazolidine-3-carboxylic acid ethyl ester (0.937 g, 3.15 mmol) in methanol (35 mL) after which the solution was allowed to warm to room temperature and stirred for 2 hours. The solution was cooled to 0° C. and sodium cyanoborohydride (0.461 g, 7.3 mmol) and acetic acid (4 mL) were added and the solution was allowed to warm to room temperature and stirred overnight. The reaction was then concentrated under reduced pressure, partitioned between dichloromethane and saturated aqueous sodium bicarbonate and the layers were separated. The organic phase was washed with brine, dried over anhydrous sodium sulfate and concentrated under reduced pressure to provide crude 2-{3-[((S)-1-Dimethylaminomethyl-3,3-dimethyl-butylamino)-methyl]-benzyl}1,1-dioxo-1λ⁶-isothiazolidine-3-carboxylic acid ethyl ester, which was carried on to the next step without further purification.

Step 5: 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid ethyl ester 2-{3-[((S)-1-Dimethylaminomethyl-3,3-dimethyl-butylamino)-methyl]-benzyl}1,1-dioxo-1λ⁶-isothiazolidine-3-carboxylic acid ethyl ester (1.1 g, 2.4 mmol) was dissolved in methanol (60 mL) and the solution was cooled to 0° C. and 6-chloro-2-fluoro-3-methoxy-benzaldehyde (Intermediate 4; 0.750 g, 3.98 mmol) was added all at once. The ice bath was removed and the solution was allowed to stir at room temperature for 40 minutes after which the solution was cooled to 0° C. To the cooled solution was added sodium cyanoborohydride (0.400 g, 6.37 mmol) and acetic acid (0.485 mL) and the solution was allowed to stir at room temperature for 5 hours after which another portion of sodium cyanoborohydride was added (0.200 g, 3.18 mmol). The solution was allowed to stir at room temperature overnight after which it was concentrated under reduced pressure. The reaction mixture was partitioned between dichloromethane and water, rinsed with saturated aqueous sodium bicarbonate and the layers were separated. The combined organic extracts were washed with brine, dried over anhydrous sodium sulfate, filtered and concentrated under reduced pressure to provide crude material, which was purified by reverse phase chromatography (Gilson; 50 Polaris C18A (50 g), 40%-100% acetonitrile/water (0.1% TFA) over 6 minutes) to provide 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid ethyl ester (0.87 g, 58%) after neutralization with sodium bicarbonate to remove trifluoroacetic acid.

Step 6: 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid ethyl ester (0.865 g, 1.4 mmol) was dissolved in tetrahydrofuran (5.6 mL). Water (5.6 mL) and lithium hydroxide (0.050 g, 2.07 mmol) and methanol (1.2 mL) were added. The reaction was stirred at room temperature for 2.5 hours after which the reaction was concentrated under reduced pressure. To the residue was added dichloromethane and aqueous hydrochloric acid (pH~7) resulting in an emulsion. The reaction was then concentrated to dryness under reduced pressure. The crude material was purified by supercritical fluid chromatography into the corresponding Epimer 1 and Epimer 2 of 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid (0.084 g (Epimer 1) and 0.089 g (Epimer 2), respectively, 99% (combined yield)).

Preparation of Preferred Compounds of the Invention

General Methods for Reductive Alkylation of 2-{3-[((S)-1-Dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide Method A. Sodium triacetoxyborohydride (available from Aldrich; 1.5 equiv.) was added to a stirred solution of 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 1.0 equiv.) and aldehyde (1.2 equiv.) in methanol (25 mL/mmol), at 0° C. The reaction mixture was stirred at room temperature for 16 h and monitored by LCMS. The reaction mixture was then evaporated completely under reduced pressure, diluted with ethyl acetate (30 mL/mmol) and washed with water (15 mL/mmol). The ethyl acetate layer was dried over anhydrous sodium sulfate and concentrated under reduced pressure. The crude reaction mixture was purified by Prep HPLC to provide the desired compound.

Method B. To a stirred solution of 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 1.0 equiv.) and aldehyde (1.2 equiv.) in methanol (25 ml/mmol) was added sodium cyanoborohydride (available from Aldrich; 1.5 equiv.) followed by acetic acid (0.2 mL/mmol), at 0° C. The reaction mixture was stirred at room temperature for 16 h and monitored by LCMS. The reaction mixture was then evaporated completely under reduced pressure, diluted with ethyl acetate (30 mL/mmol) and washed with water (15 mL/mmol). The ethyl acetate layer was dried over anhydrous sodium sulfate and concentrated under reduced pressure. The crude reaction mixture was purified by Prep HPLC to provide the desired compound.

Example 1

2-(3-{[(5-Chloro-2-hydroxy-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide

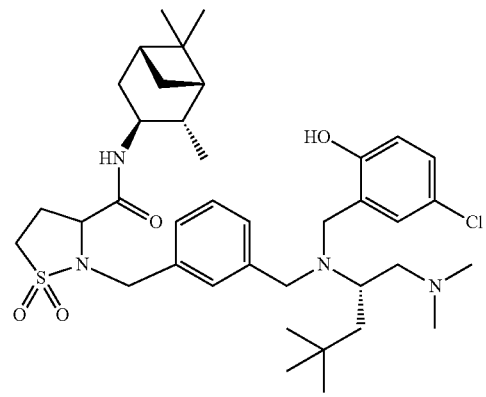

Using Method A, 2-{3-[((S)-1-Dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 5-chloro-2-hydroxy-benzaldehyde (available from Aldrich; 0.066 g, 0.430 mmol) were reacted to form 2-(3-{[(5-Chloro-2-hydroxy-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide (0.0450 g, 18%). Mass spectrum: m/Z: 701.5 (M+1)

Example 2

2-(3-{[((S)-1-Dimethylaminomethyl-3,3-dimethyl-butyl)-(2-iodo-benzyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

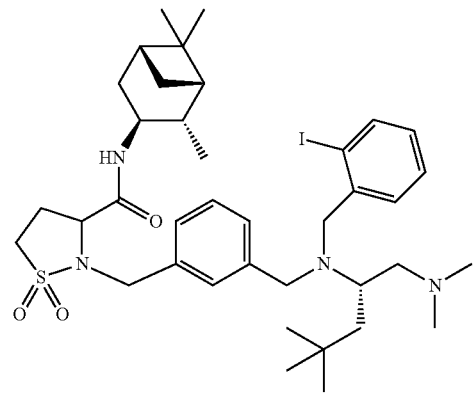

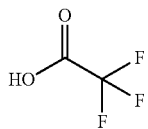

Using Method A, 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-iodobenzaldehyde (available from Aldrich; 0.099 g, 0.430 mmol) were reacted to form 2-(3-{[((S)-1-dimethylaminomethyl-3,3-dimethyl-butyl)-(2-iodo-benzyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.070 g, 25%). Mass spectrum: m/Z: 777.4 (M+1).

Example 3

2-(3-{[((S)-1-Dimethylaminomethyl-3,3-dimethyl-butyl)-(2-ethoxy-benzyl)-amino]methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

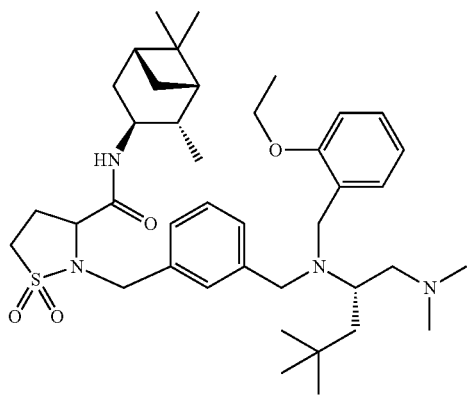

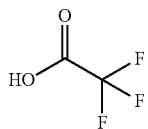

Using Method A, 2-{3-[((S)-1-Dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-ethoxy-benzaldehyde (available from Aldrich; 0.0640 g, 0.430 mmol) were reacted to form 2-(3-{[((S)-1-Dimethylaminomethyl-3,3-dimethyl-butyl)-(2-ethoxy-benzyl)-amino]methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.050 g, 21%). Mass spectrum: m/Z: 695.2 (M+1).

Example 4

2-(3-{[((S)-1-Dimethylaminomethyl-3,3-dimethyl-butyl)-(5-isopropyl-2-methoxy-benzyl)-amino]-methyl}-benzyl)-1,1-1λ⁶-isothiazolidine-3-carboxylic acid((1S,2S,3S,5R)-2,6,6-trimethyl-bicyclo[3.1.1]hept-3-yl)-amide trifluoroacetate salt

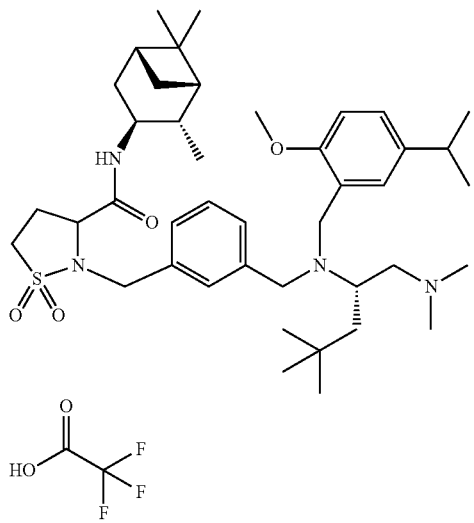

Using Method A, 2-{3-[((S)-1-Dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 5-isopropyl-2-methoxy-benzaldehyde (available from 3B Scientific Corporation, Libertyville, Ill. 60048, USA; 0.0760 g, 0.430 mmol) were reacted to form 2-(3-{[((S)-1-Dimethylaminomethyl-3,3-dimethyl-butyl)-(5-isopropyl-2-methoxy-benzyl)-amino]-methyl}-benzyl)-1,1-1λ⁶-isothiazolidine-3-carboxylic acid((1S,2S,3S,5R)-2,6,6-trimethyl-bicyclo[3.1.1]hept-3-yl)-amide trifluoroacetate salt (0.075 g, 29%). Mass spectrum: m/Z: 723.2 (M+1).

Example 5

2-(3-{[(2-Difluoromethoxy-benzyl)-((S)-1-dimethylaminomethyl-3,3-dimethyl-butyl)amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

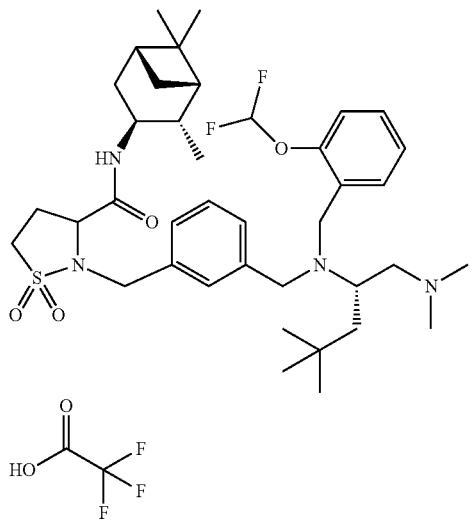

Using Method A, 2-{3-[((S)-1-Dimethylaminomethyl-3,3-dimethyl-butylamino)methyl]-benzyl}-1,1-dioxo-1$\lambda^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-difluoromethoxy-benzaldehyde (available from Aldrich; 0.0730 g, 0.430 mmol) were reacted to form 2-(3-{[(2-Difluoromethoxy-benzyl)-((S)-1-dimethylaminomethyl-3,3-dimethyl-butyl)amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt (0.061 g, 24%). Mass spectrum: m/Z: 717.5 (M+1).

Example 6

2-[3-({((S)-1-Dimethylaminomethyl-3,3-dimethyl-butyl)-[2-(4-fluoro-phenoxy)-benzyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt

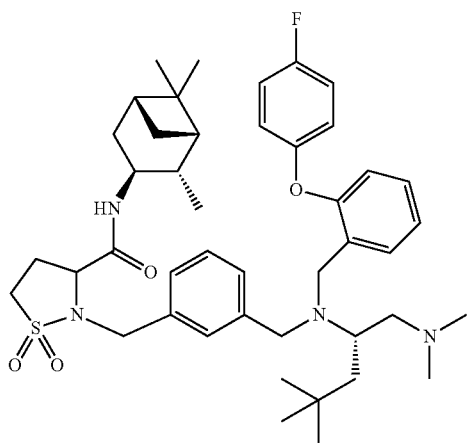

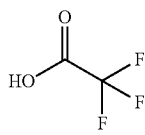

Using Method A, 2-{3-[((S)-1-dimethylaminomethyl-3,3-dimethyl-butylamino)methyl]-benzyl}-1,1-dioxo-1$\lambda^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-(4-fluoro-phenoxy)-benzaldehyde (available from Aldrich; 0.093 g, 0.430 mmol) were reacted to form 2-[3-({((S)-1-dimethylaminomethyl-3,3-dimethyl-butyl)-[2-(4-fluoro-phenoxy)-benzyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt (0.060 g, 22%). Mass spectrum: m/Z: 761.5 (M+1).

Example 7

2-(3-{[((S)-1-Dimethylaminomethyl-3,3-dimethyl-butyl)-(2-p-tolyloxy-benzyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt

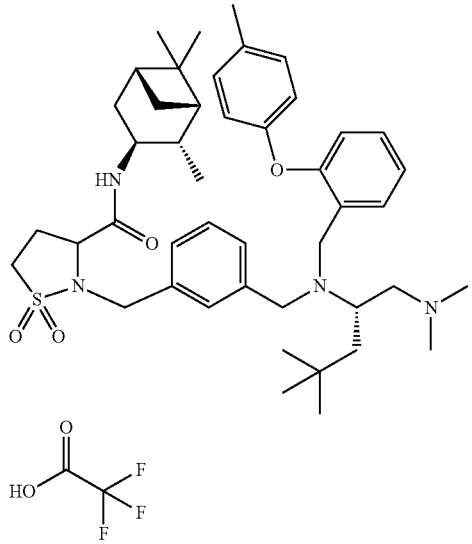

Using Method A, 2-{3-[((S)-1-dimethylaminomethyl-3,3-dimethyl-butylamino)methyl]-benzyl}-1,1-dioxo-1$\lambda^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-(4-methylphenoxy)benzene carbaldehyde (available from Alfa Aesar, 26 Parkridge Road, Ward Hill, Mass. 01835, USA; 0.091 g, 0.430 mmol) were reacted to form 2-(3-{[((S)-1-Dimethylaminomethyl-3,3-dimethyl-butyl)-(2-p-tolyloxy-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt (0.080 g, 30%). Mass spectrum: m/Z: 757.5 (M+1).

Example 8

2-(3-{[((S)-1-Dimethylaminomethyl-3,3-dimethyl-butyl)-(4'-fluoro-biphenyl-2 ylmethyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt

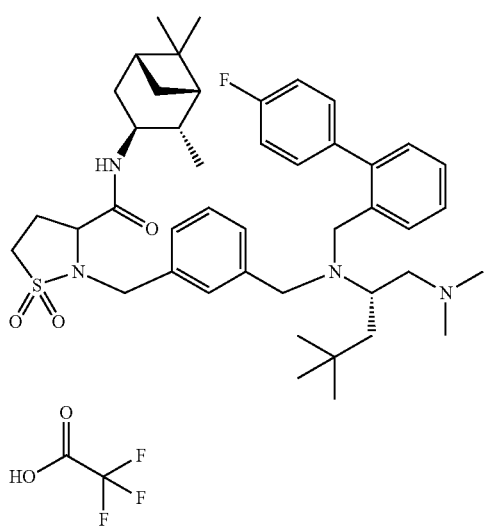

Using Method A, 2-{3-[((S)-1-dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-(available from Alfa Aesar, 26 Parkridge Road, Ward Hill, Mass. 01835, USA; 4-fluorophenyl)benzaldehyde (0.086 g, 0.430 mmol) were reacted to form 2-(3-{[((S)-1-Dimethylaminomethyl-3,3-dimethyl-butyl)-(4'-fluoro-biphenyl-2 ylmethyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate (0.045 g, 17%). Mass spectrum: m/Z: 745.5 (M+1).

Example 9

2-(3-{[((S)-1-Dimethylaminomethyl-3,3-dimethyl-butyl)-(2-hydroxy-4-methylbenzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt

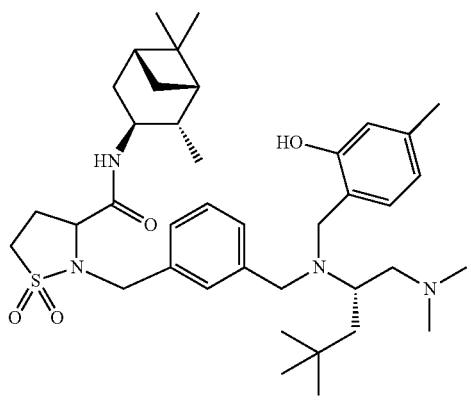

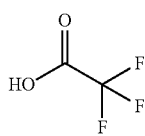

Using Method B, 2-{3-[((S)-1-dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-hydroxy-4-methylbenzaldehyde (available from Aldrich Chemical Company, Inc., 1001 West Saint Paul Avenue, Milwaukee, Wis. 53233, USA; 0.058 g, 0.430 mmol) were reacted to form 2-(3-{[((S)-1-Dimethylaminomethyl-3,3-dimethyl-butyl)-(2-hydroxy-4-methyl-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt (0.035 g, 15%). Mass spectrum: m/Z: 681.6 (M+1).

Example 10

2-(3-{[((S)-1-Dimethylaminomethyl-3,3-dimethyl-butyl)-(2-hydroxy-5-methyl-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt

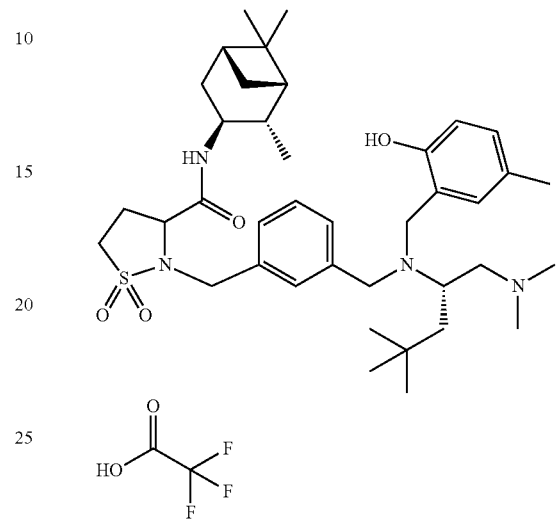

Using Method B, 2-{3-[((S)-1-dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-hydroxy-5-methylbenzaldehyde (available from Aldrich Chemical Company, Inc., 1001 West Saint Paul Avenue, Milwaukee, Wis. 53233, USA; 0.058 g, 0.430 mmol) were reacted to form 2-(3-{[((S)-1-Dimethylaminomethyl-3,3-dimethyl-butyl)-(2-hydroxy-5-methyl-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt (0.050 g, 21%). Mass spectrum: m/Z: 681.4 (M+1).

Example 11

2-(3-{[((S)-1-Dimethylaminomethyl-3,3-dimethyl-butyl)-(2'-methyl-biphenyl-2 ylmethyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt

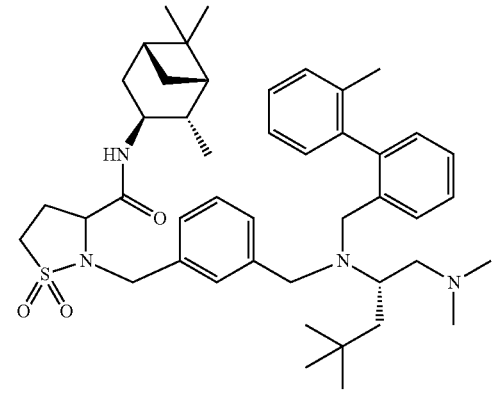

-continued

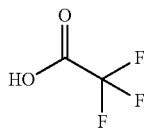

Using Method A, 2-{3-[((S)-1-dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2'-methyl-biphenyl-2-carboxaldehyde (available from Alfa Aesar, 26 Parkridge Road, Ward Hill, Mass. 01835, USA; 0.084 g, 0.430 mmol) were reacted to form 2-(3-{[((S)-1-Dimethylaminomethyl-3,3-dimethyl-butyl)-(2'-methyl-biphenyl-2ylmethyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt (0.034 g, 13%). Mass spectrum: m/Z: 741.6 (M+1).

Example 12

2-(3-{[((S)-1-Dimethylaminomethyl-3,3-dimethyl-butyl)-(2-fluoro-6-phenoxy-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt

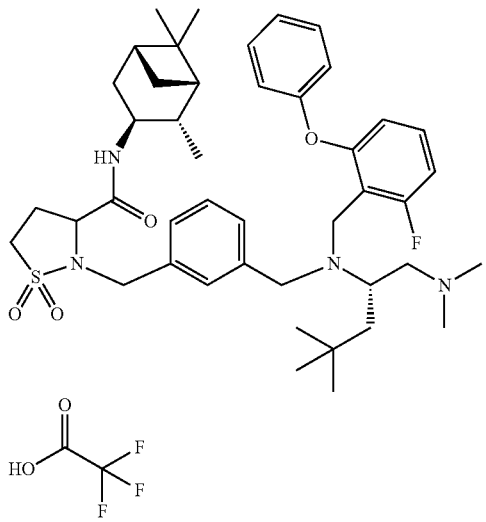

Using Method B, 2-{3-[((S)-1-dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2-fluoro-6-phenoxybenzaldehyde (available from Alfa Aesar, 26 Parkridge Road, Ward Hill, Mass. 01835, USA; 0.093 g, 0.430 mmol) were reacted to form 2-(3-{[((S)-1-Dimethylaminomethyl-3,3-dimethyl-butyl)-(2-fluoro-6-phenoxy-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt (0.016 g, 6%). Mass spectrum: m/Z: 761.6 (M+1).

Example 13

2-(3-{[((S)-1-Dimethylaminomethyl-3,3-dimethyl-butyl)-(2,3,6-trifluoro-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt

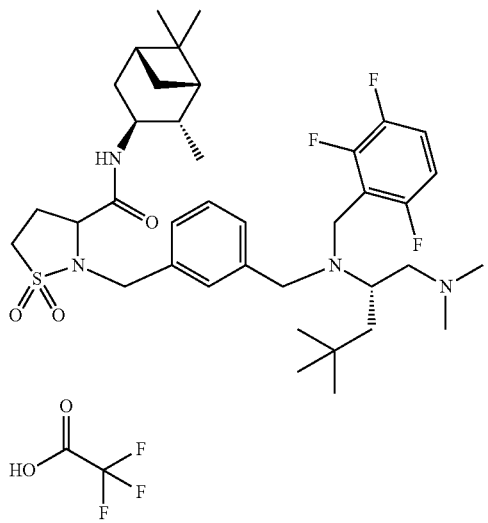

Using Method A, 2-{3-[((S)-1-dimethylaminomethyl-3,3-dimethyl-butylamino)methyl]-benzyl}-1,1-dioxo-1λ$^6$-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2,3,6-trifluorobenzaldehyde (available from Alfa Aesar, 26 Parkridge Road, Ward Hill, Mass. 01835, USA; 0.068 g, 0.430 mmol) were reacted to form 2-(3-{[((S)-1-Dimethylaminomethyl-3,3-dimethyl-butyl)-(2,3,6-trifluoro-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt (0.025 g, 10%). Mass spectrum: m/Z: 705.5 (M+1).

Example 14

2-(3-{[(6-Bromo-2-hydroxy-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt

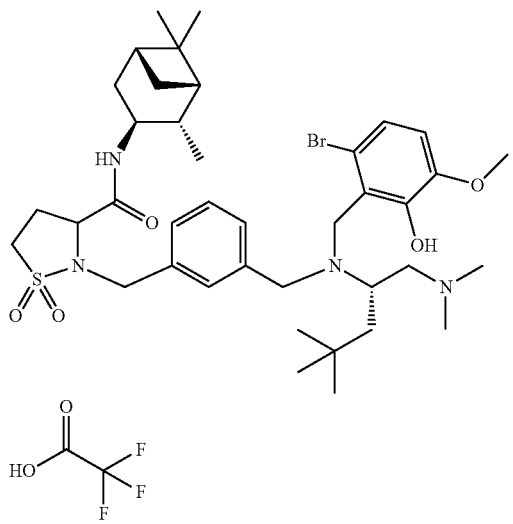

Using Method B, 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 6-bromo-2-hydroxy-3-methoxy-benzaldehyde (available from Aldrich Chemical Company, Inc., 1001 West Saint Paul Avenue, Milwaukee, Wis. 53233, USA; 0.099 g, 0.430 mmol) were reacted to form 2-(3-{[(6-bromo-2-hydroxy-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.055 g, 20%). Mass spectrum: m/Z: 775.4 (M+1).

Example 15

2-(3-{[(6-Chloro-2-fluoro-3-methyl-benzyl)-((S)-1-dimethylaminomethyl-3,3-dimethyl butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

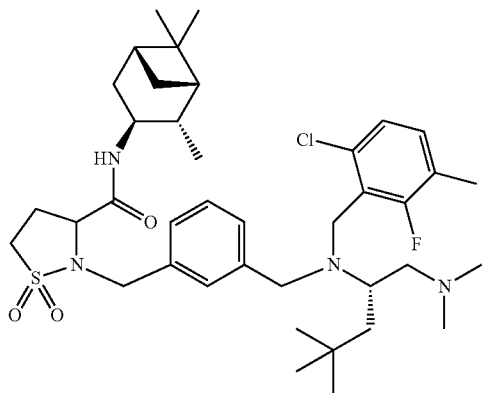

Using Method B, 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 6-chloro-2-fluoro-3-methylbenzaldehyde (available from Aldrich Chemical Company, Inc., 1001 West Paul Avenue, Milwaukee, Wis. 53233, USA; 0.024 g, 0.430 mmol) were reacted to form 2-(3-{[(6-chloro-2-fluoro-3-methyl-benzyl)-((S)-1-dimethylaminomethyl-3,3-dimethyl butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.060 g, 24%). Mass spectrum: m/Z: 717.4 (M+1).

Example 16

2-(3-{[[2-(4-Cyano-phenoxy)-benzyl]-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

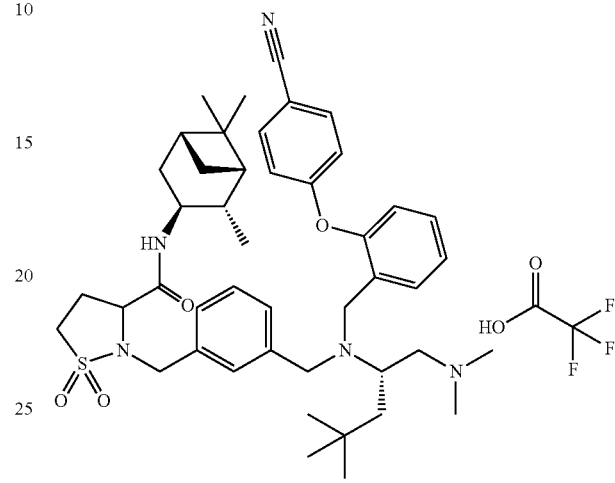

Using Method B, 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 4-(2-formylphenoxy)benzonitrile (available from Alfa Aesar, 26 Parkridge Road, Ward Hill, Mass. 01835, USA; 0.096 g, 0.430 mmol) were reacted to form 2-(3-{[[2-(4-cyano-phenoxy)-benzyl]-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.024 g, 9%). Mass spectrum: m/Z: 768.5 (M+1).

Example 17

2-(3-{[Benzo[1,3]dioxol-4-ylmethyl-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

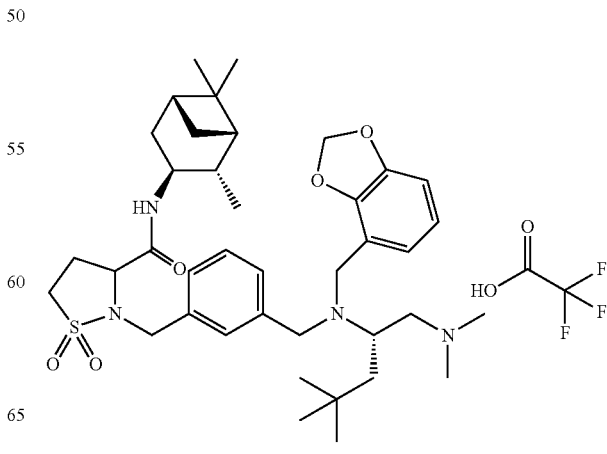

Using Method B, 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 2,3-(methylenedioxy)benzaldehyde (available from Aldrich Chemical Company, Inc., 1001 West Saint Paul Avenue, Milwaukee, Wis. 53233, USA; 0.064 g, 0.430 mmol) were reacted to form 2-(3-{[benzo[1,3]dioxol-4-ylmethyl-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.038 g, 15%). Mass spectrum: m/Z: 695.5 (M+1).

Example 18

2-(3-{[(3-Bromo-2,6-difluoro-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt

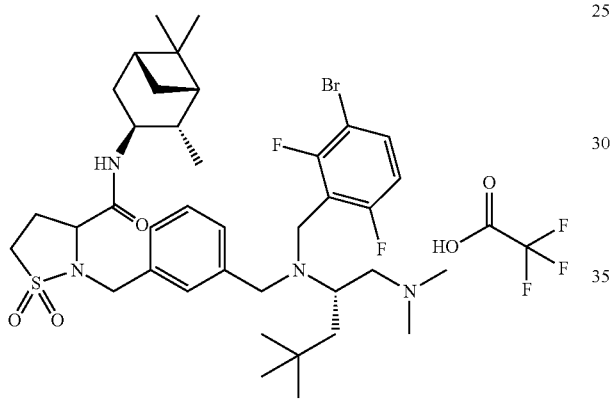

Using Method B, 2-{3-[((S)-1-dimethylaminomethyl-3,3-dimethyl-butylamino)methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 6, 0.200 g, 0.360 mmol) and 3-bromo-2,6-difluorobenzaldehyde (available from Alfa Aesar, 26 Parkridge Road, Ward Hill, Mass. 01835, USA; 0.095 g, 0.430 mmol) were reacted to form 2-(3-{[(3-bromo-2,6-difluoro-benzyl)-((S)-1-dimethylaminomethyl-3,3-dimethyl-butyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide trifluoroacetate salt (0.038 g, 15%). Mass spectrum: m/Z: 765.4 (M+1).

General Method for Coupling of Intermediate 7

2-(3-{[(6-Chloro-2-fluoro-3-methoxy-benzyl)-((S)-1 dimethylaminomethyl-3,3-dimethyl-butyl)-amino] methyl}-benzyl)-1,1-dioxo-1λ⁶-isothiazolidine-3-carboxylic acid To a stirred solution of 2-(3-{[(6-chloro-2-fluoro-3-methoxy-benzyl)-((S)-1dimethylaminomethyl-3,3-dimethyl-butyl)-amino]-methyl}-benzyl)-1,1-dioxo-1λ⁶-isothiazolidine-3-carboxylic acid (Intermediate 7, 1.0 equiv.) in anhydrous N,N-dimethylformamide (8 mL/mmol) cooled in an ice bath (0° C.) was added sequentially O-benzotriazol-1-yl-N,N,N',N'-tetramethyluronium hexafluorophosphate (available from Aldrich; 1.2 equiv.), 1-hydroxybenzotriazole (available from 3B Scientific Corporation, Libertyville, Ill. 60048, USA; 1.2 equiv.), amine (1.2 equiv.) and triethylamine (6.0 equiv.). The reaction mixture was allowed to warm to room temperature and stir until the starting material was completely consumed as determined by LCMS. To the reaction mixture was added water and ethyl acetate. The organic phase was extracted and washed with water, dried over anhydrous sodium sulfate and concentrated under reduced pressure. The crude reaction mass was purified by Prep HPLC to provide the desired compound as the TFA salt. The pure residue was taken up in ethyl acetate and washed with saturated sodium bicarbonate to remove the TFA and then with water.

The above method is the method used in Examples 19, 20, 24 to 28, and 30 to 34.

Example 19

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid((1R,2R,3R,5S)-2,6,6-trimethyl-bicyclo[3.1.1]hept-3-yl)-amide

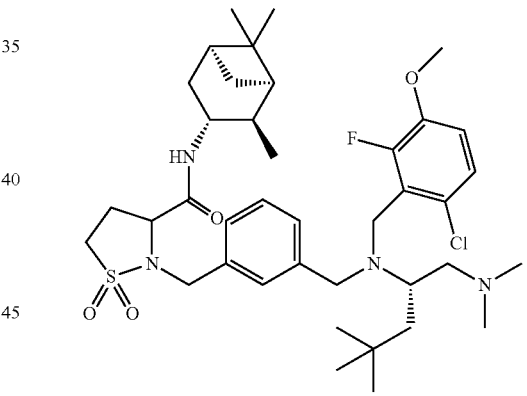

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ⁶-isothiazolidine-3-carboxylic acid (Intermediate 7, 0.089 g, 0.148 mmol) was reacted with (1R,2R,3R,5S)-2,6,6-trimethyl-bicyclo[3.1.1]hept-3-ylamine (available from Aldrich Chemical Company, Inc., 1001 West Saint Paul Avenue, Milwaukee, Wis. 53233, USA; 30 µL, 0.179 mmol) to form 2-(3-{[(6-chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid((1R,2R,3R,5S)-2,6,6-trimethyl-bicyclo[3.1.1]hept-3-yl)-amide (0.075 g, 68%). m/z=733 (M+1); HRMS: calcd for $C_{39}H_{59}ClFN_4O_4S$. Calc [M+H]⁺ 733.3924. found 733.3920.

Example 20

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothizolidine-3-carboxylic acid adamantan-1-ylamide

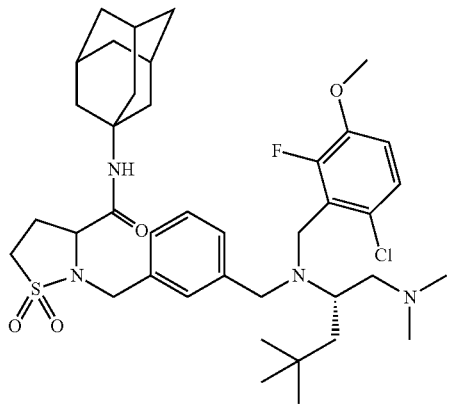

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ⁶-isothiazolidine-3-carboxylic acid (Intermediate 7, 0.080 g, 0.134 mmol) was reacted with 1-adamantanamine (available from Aldrich Chemical Company, Inc., 1001 West Saint Paul Avenue, Milwaukee, Wis. 53233, USA; 0.025 g, 0.179 mmol) to form 2-(3-{[(6-chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid adamantan-1-ylamide (0.066 g, 68%). m/z=731 (M+1); HRMS: calcd for $C_{39}H_{57}ClFN_4O_4S$. Calc [M+H+] 731.3768. found 731.3766.

Example 21

2-(3-{[(6-Chloro-2-fluoro-3-methoxy-benzyl)-((S)-1-dimethylaminomethyl-2-phenyl-ethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide

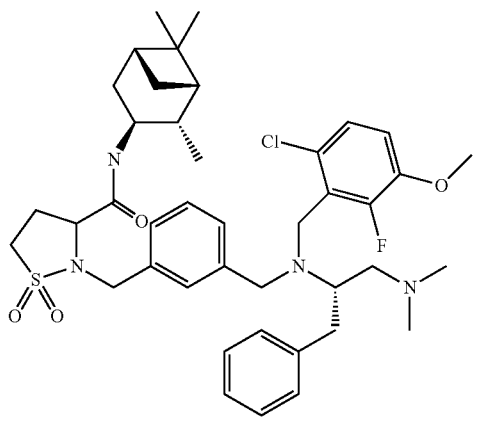

6-Chloro-2-fluoro-3-methoxy-benzaldehyde (Intermediate 4; 21 mg, 0.11 mmol) was added to a solution of 2-{3-[((S)-1-dimethylaminomethyl-2-phenyl-ethylamino)-methyl]-benzyl}-1,1-dioxo-1λ⁶-isothiazolidine-3-carboxylic acid((1S,2S,3S,5R)-2,6,6-trimethyl-bicyclo[3.1.1]hept-3-yl)-amide (Intermediate 5; 58 mg, 0.1 mmol) in methanol (3 mL) at 0° C. under argon. The mixture was stirred for a few minutes and then sodium triacetoxyborohydride (32 mg, 0.15 mmol) was added. The mixture was stirred overnight at room temperature. At this time, LCMS showed mainly starting material. The mixture was cooled in an ice-bath and sodium cyanoborohydride (3 mg, 0.05 mmol) was added. The mixture was stirred for 2 h. LCMS indicated about 50% conversion. 6-Chloro-2-fluoro-3-methoxy-benzaldehyde (Intermediate 4; 10 mg, 0.05 mmol) was added, followed by sodium cyanoborohydride (3 mg, 0.05 mmol) and acetic acid (50 μL). The reaction mixture was stirred for 4 h at room temperature, and it was then concentrated under reduced pressure to remove methanol. Ethyl acetate (50 mL) was added and the mixture was washed with water (2×25 mL), and brine (25 mL). The organic phase was dried over sodium sulfate, filtered and concentrated to give crude product (78 mg). Chromatography on a 4 gm Isco column, eluting with 0-10% methanol/dichloromethane, followed by trituration with ether/pentane (1/1, 2 mL) gave 2-(3-{[(6-chloro-2-fluoro-3-methoxy-benzyl)-((S)-1-dimethylaminomethyl-2-phenyl-ethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide as a white solid (18 mg, 24%). HRMS: calcd for $C_{41}H_{55}ClFN_4O_4S$. Calc [M+H⁺] 753.3611. found 753.3605.

Example 22

2-[3-({(6-Chloro-2-fluoro-3-methoxy-benzyl)-[(S)-2-(3-chloro-phenyl)-1-dimethylaminomethyl-ethyl]-amino}-methyl)-benzyl]-1,1-dioxo-1λ⁶-isothiazolidine-3-carboxylic acid((1S,2S,3S,5R)-2,6,6-trimethyl-bicyclo[3.1.1]hept-3-yl)-amide

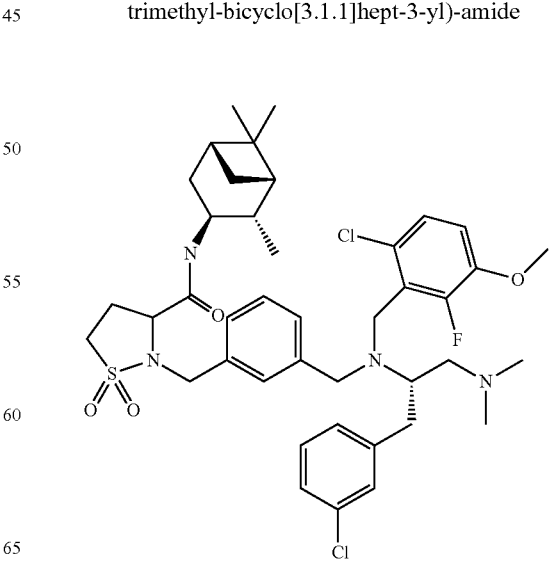

Step 1: (S)-2-Amino-3-(3-chloro-phenyl)-N,N-dimethyl-propionamide trifluoroacetate salt

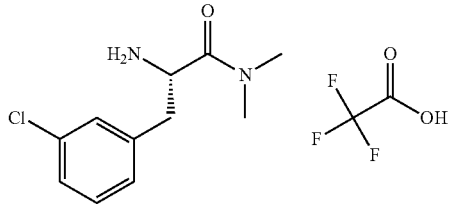

A mixture of Boc-L-4-chlorophenylalanine (Chem-Impex International, Inc., Wood Dale, Ill., USA; 5.0 g, 16.7 mmol), dimethylamine (2 M in tetrahydrofuran; 12.5 mL, 25 mmol), 1-hydroxybenzotriazole (available from 3B Scientific Corporation, Libertyville, Ill. 60048, USA; 2.69 g, 19.9 mmol), O-benzotriazol-1-yl-N,N,N',N'-tetramethyluronium hexafluororophosphate (available from Aldrich Chemical Company, Inc., 1001 West Saint Paul Avenue, Milwaukee, Wis. 53233, USA; 7.5 g, 19.8 mmol) and diisopropylethylamine (available from Aldrich Chemical Company, Inc., 1001 West Saint Paul Avenue, Milwaukee, Wis. 53233, USA; 8.8 mL, 50.5 mmol) in N,N-dimethylformamide (available from Aldrich Chemical Company, Inc., 1001 West Saint Paul Avenue, Milwaukee, Wis. 53233, USA) was stirred at 0° C. for 30 min. Ethyl acetate was added and the mixture was washed with brine. The organic phase was dried over sodium sulfate, filtered and evaporated. The residue was dissolved in dichloromethane (80 mL). Trifluoroacetic acid (80 mL) was added and the solution was stirred for 2 h at room temperature. The solvents were evaporated to give (S)-2-amino-3-(3-chloro-phenyl)-N,N-dimethyl-propionamide trifluoroacetate salt (4.0 g) as a white solid.

Step 2: (S)-3-(3-chloro-phenyl)-N1,N1-dimethyl-propane-1,2-diamine hydrochloride salt

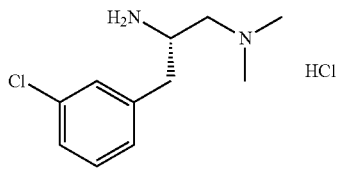

A solution of lithium aluminum hydride in tetrahydrofuran (3.5 M; 20 mL; 70 mmol) was added cautiously to an ice-bath cooled solution of (S)-2-amino-3-(3-chloro-phenyl)-N,N-dimethyl-propionamide trifluoroacetate salt (4.00 g, 11.8 mmol) in tetrahydrofuran (20 mL). The reaction mixture was heated at reflux for 4 h, and then cooled. Ethyl acetate and ether were added, and then 3 M sodium hydroxide solution (100 mL) was added. The layers were separated and the aqueous layer was back-extracted with ether. The combined organic layers were washed with brine, dried over sodium sulfate, filtered, and evaporated. The residue was taken up in 1 M HCl in ether (20 mL). The resulting white precipitate was stirred for 1 h, and then filtered to give (S)-3-(3-chloro-phenyl)-N1,N1-dimethyl-propane-1,2-diamine hydrochloride salt (1.92 g, 57%).

Step 3: 2-{3-[((S)-3-Chloro-phenyl)-1-dimethylaminomethyl-ethylamino)-methyl]-benzyl}-1,1-dioxo-1λ⁶-isothiazolidine-3-carboxylic acid ethyl ester

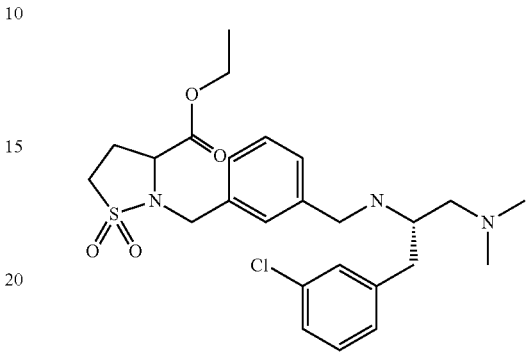

Triethylamine (338 μL, 2.4 mmol) was added to a solution of (S)-3-(3-chloro-phenyl)-N1,N1-dimethyl-propane-1,2-diamine hydrochloride salt (264 mg, 1.06 mmol) in methanol (2 mL) under argon at room temperature. The mixture was stirred for 10 min and then a solution of 2-(3-formyl-benzyl)-1,1-dioxo-1λ⁶-isothiazolidine-3-carboxylic acid ethyl ester (Intermediate 8 Step 3; 250 mg, 0.96 mmol) in methanol (4 mL) was added under argon. The mixture was stirred at room temperature for 15 min and then cooled in an ice-bath. Solid sodium cyanoborohydride (90.9 mg, 1.45 mmol) and glacial acetic acid (750 μL) were added. The reaction mixture was allowed to warm to room temperature and stir. The progress of the reaction was monitored by LCMS. When the reaction was substantially complete, the solvents were evaporated and ethyl acetate (50 mL) was added. The solution was washed with washed with water (2×10 mL) and the aqueous layer was extracted with ethyl acetate (50 mL). The combined organics were dried over sodium sulfate, filtered and concentrated to give crude 2-{3-[((S)-3-chloro-phenyl)-1-dimethylaminomethyl-ethylamino)-methyl]-benzyl}-1,1-dioxo-1λ⁶-isothiazolidine-3-carboxylic acid ethyl ester (430 mg) as a yellow foam which was used directly in the next step without further purification.

Step 4: 2-{3-[((S)-3-Chloro-phenyl)-1-dimethylaminomethyl-ethylamino)-methyl]-benzyl}-1,1-dioxo-1λ⁶-isothiazolidine-3-carboxylic acid

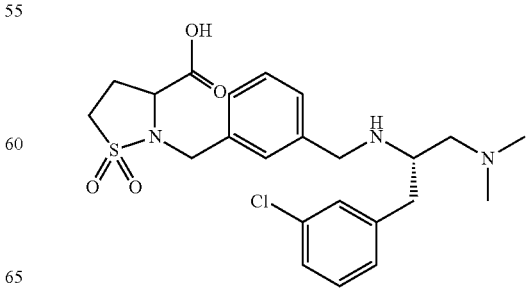

To a solution of crude 2-{3-[((S)-3-chloro-phenyl)-1-dimethylaminomethyl-ethylamino)-methyl]-benzyl}-1,1-dioxo-1λ⁶-isothiazolidine-3-carboxylic acid ethyl ester (430 mg, approx. 0.96 mmol) in tetrahydrofuran (4 mL) was added lithium hydroxide hydrate (71 mg, 1.7 mmol) followed by water (1 mL). The reaction mixture was stirred at room temperature for 2 h, and then the mixture was concentrated under reduced pressure to remove tetrahydrofuran. The remaining solution was stirred and approximately 25 drops of 1 M hydrochloric acid were added to bring the pH to 4.5. The sample was stirred for 10 min and the aqueous solution was decanted away from the yellow gum. The gum was washed with water (2 mL). The combined aqueous layers were evaporated to dryness, and dried overnight to give 2-{3-[((S)-3-chloro-phenyl)-1-dimethylaminomethyl-ethylamino)-methyl]-benzyl}-1,1-dioxo-1λ⁶-isothiazolidine-3-carboxylic acid as a white residue (200 mg).

Step 5: 2-{3-{[(S)-2-(3-Chloro-phenyl)-1-dimethylaminomethyl-ethylamino)-methyl]-benzyl}-1,1-dioxo-1λ⁶-isothiazolidine-3-carboxylic acid ((1S,2S,3S,5R)-2,6,6-trimethyl-bicylo[3.1.1]hept-3-yl)amide

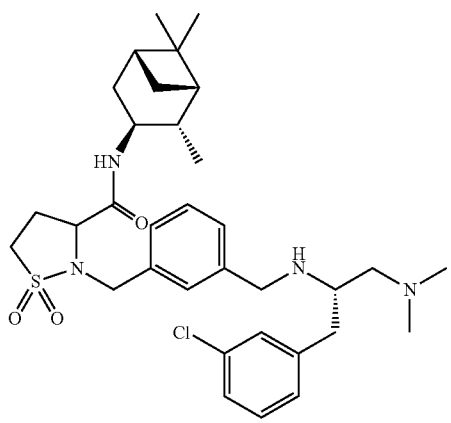

(+)-Isopinocampheylamine (Aldrich; 61 mg, 0.38 mmol), O-(benzotriazol-1-yl)-N,N,N',N'-tetramethyluronium tetrafluoroborate (available from Aldrich Chemical Company, Inc., 1001 West Saint Paul Avenue, Milwaukee, Wis. 53233, USA; 122 mg, 0.38 mmol), N-hydroxybenzotriazole (available from 3B Scientific Corporation, Libertyville, Ill. 60048, USA; 51 mg, 0.38 mmol) in dry N,N-dimethylformamide (6 mL) were added to a cooled (0° C.) solution of 2-{3-[((S)-3-chloro-phenyl)-1-dimethylaminomethyl-ethylamino)-methyl]-benzyl}-1,1-dioxo-1λ⁶-isothiazolidine-3-carboxylic acid (200 mg ~90% pure, 0.38 mmol) under argon. N,N-Diisopropylethylamine (147 μL, 0.83 mmol) was then added. The solution was then stirred at room temperature for 45 min. The reaction mixture was diluted with ethyl acetate (50 mL) and washed with 1N NaOH (3×15 mL), and brine (20 mL). The organic phase was dried over sodium sulfate, filtered and concentrated to give the crude product (160 mg) as a viscous oil. This material was combined with the crude product from an identical experiment using 2-{3-[((S)-1-dimethylaminomethyl-2-phenyl-ethylamino)-methyl]-benzyl}-1,1-dioxo-1λ⁶-isothiazolidine-3-carboxylic acid (270 mg; produced in Step 5 of the above-described process for making Intermediate 6). The combined lots were chromatographed, eluting with 0-10% methanol/dichloromethane to give 2-{3-{[(S)-2-(3-chloro-phenyl)-1-dimethylaminomethyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide (106 mg, 18%) as a tan foam.

Step 6: 2-{3-{[(S)-2-(3-Chloro-phenyl)-1-dimethylaminomethyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide

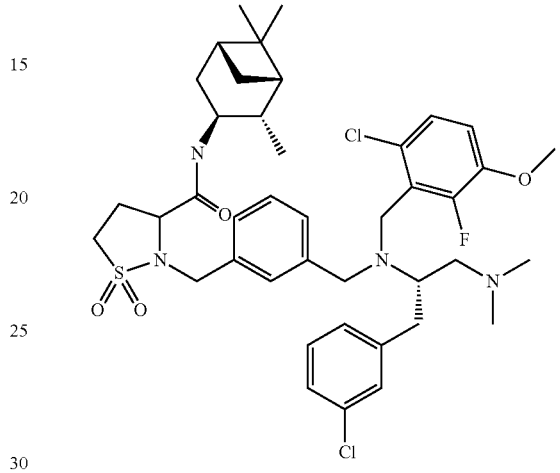

6-Chloro-2-fluoro-3-methoxy-benzaldehyde (Intermediate 4; 18 mg, 0.095 mmol) was added to a solution of 2-{3-{[(S)-2-(3-chloro-phenyl)-1-dimethylaminomethyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide (50 mg, 0.086 mmol) in methanol (3 mL) at 0° C. under argon. The mixture was stirred at 0° C. for a few minutes and then sodium cyanoborohydride (8 mg, 0.13 mmol) and glacial acetic acid (43 μL) were added. The mixture was stirred for 90 min at room temperature. The solution was cooled again to 0° C., and 6-chloro-2-fluoro-3-methoxy-benzaldehyde (Intermediate 4; 5 mg, 0.027 mmol) was added. After 5 min, sodium cyanoborohydride (5 mg, 0.08 mmol) from a fresh bottle was added. The mixture was stirred for 6 h at room temperature. The solution was cooled again to 0° C., and 6-chloro-2-fluoro-3-methoxy-benzaldehyde (Intermediate 4; 5 mg, 0.027 mmol) was added. After 5 min, sodium cyanoborohydride (5 mg, 0.08 mmol) was added. The mixture was stirred overnight at room temperature. The solution was cooled again to 0° C., and 6-chloro-2-fluoro-3-methoxy-benzaldehyde (Intermediate 4; 5 mg, 0.027 mmol) was added. After 5 min, sodium cyanoborohydride (5 mg, 0.08 mmol) was added. The mixture was stirred for 4 h at room temperature. The solution was concentrated to remove methanol. Ethyl acetate (50 mL) was added and the mixture was washed with water (2×25 mL), and brine (25 mL). The aqueous layers were back-extracted with ethyl acetate (50 mL). The combined organic phases were dried over sodium sulfate, filtered and concentrated to give crude product (82 mg). Chromatography on an 8 gm silica column, eluting with 0-10% methanol/dichloromethane, followed by trituration with ether/pentane (1/1, 2 mL) gave 2-[3-({(6-chloro-2-fluoro-3-methoxy-benzyl)-[(S)-2-(3-chloro-phenyl)-1-dimethylaminomethyl-ethyl}-amino}-methyl)-benzyl]-1,1-dioxo-1λ⁶-isothiazolidine-3-carboxylic acid((1S,2S,3S,5R)-2,6,6-trimethyl-bicyclo[3.1.1]hept-3-yl)-amide as a white solid (40 mg, 62%). HRMS: calcd for $C_{41}H_{54}Cl_2FN_4O_4S$. Calc [M+H$^+$] 787.3222. found 787.3221.

Example 23

2-[3-({(6-Chloro-2-fluoro-3-methoxy-benzyl)-[(S)-2-(4-chloro-phenyl)-1-dimethylaminomethyl-ethyl]-amino}-methyl)-benzyl]-1,1-dioxo-1λ$^6$-isothiazolidine-3-carboxylic acid((1S,2S,3S,5R)-2,6,6-trimethyl-bicyclo[3.1.1]hept-3-yl)-amide

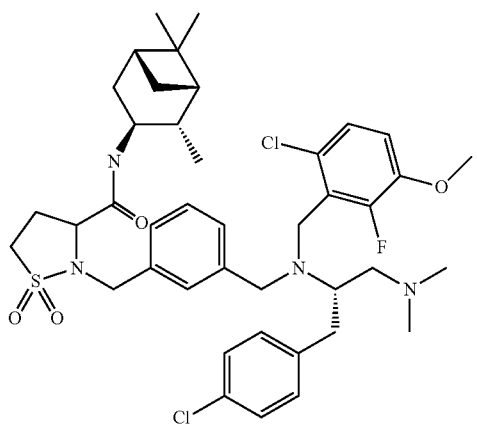

Step 1: (S)-2-Amino-3-(4-chloro-phenyl)-N,N-dimethyl-propionamide trifluoroacetate salt

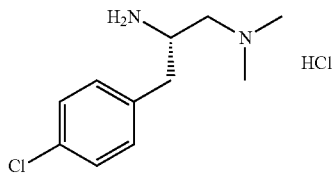

A mixture of Boc-L-4-chlorophenylalanine (Bachem California Inc., Torrance, Calif., USA; 5.0 g, 16.7 mmol), dimethylamine (2 M in tetrahydrofuran; 12.5 mL, 25 mmol), 1-hydroxybenzotriazole (available from 3B Scientific Corporation, Libertyville, Ill. 60048, USA; 2.69 g, 19.9 mmol), O-benzotriazol-1-yl-N,N,N',N'-tetramethyluronium hexafluorophosphate (available from Aldrich Chemical Company, Inc., 1001 West Saint Paul Avenue, Milwaukee, Wis. 53233, USA; 7.5 g, 19.8 mmol) and diisopropylethylamine (8.8 mL, 50.5 mmol) in N,N-dimethylformamide was stirred at 0° C. for 30 min and then at room temperature for 10 min. Ethyl acetate was added and the mixture was washed with water and brine. The organic phase was dried over sodium sulfate, filtered and evaporated to give a white solid. The solid was dissolved in dichloromethane (30 mL). Trifluoroacetic acid (30 mL) was added and the solution was stirred for 2 h at room temperature. The solvents were evaporated to give (S)-2-amino-3-(4-chloro-phenyl)-N,N-dimethyl-propionamide trifluoroacetate salt as a white solid.

Step 2: (S)-3-(4-Chloro-phenyl)-N1,N1-dimethyl-propane-1,2-diamine hydrochloride salt

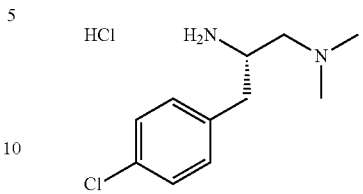

A solution of lithium aluminum hydride in tetrahydrofuran (Fluka; 3.5 M; 23 mL; 80.5 mmol) was added cautiously to an ice-bath cooled solution of (S)-2-amino-3-(4-chloro-phenyl)-N,N-dimethyl-propionamide trifluoroacetate salt (3.00 g, 13.2 mmol) in dry tetrahydrofuran (36 mL). The reaction mixture was heated at reflux for 4 h, and then cooled using an ice-bath. Ethyl acetate (25 mL) was added cautiously to destroy excess lithium aluminum hydride, and then 3 M sodium hydroxide solution (25 mL) was added. Ethyl acetate (100 mL) and saturated brine (50 mL) were added and the mixture was stirred vigorously. The layers were separated and the organic layer was washed with brine (50 mL). The brine extract was back-extracted with ethyl acetate. The combined organic layers were dried over sodium sulfate, filtered, evaporated, and concentrated to give the crude free base (1.9 g). This was taken up in dry diethyl ether (25 mL) and the mixture was stirred. A solution of HCl in ether (1 M; 25 mL) was added dropwise. The resulting white precipitate was stirred for 5 min, filtered under a stream of nitrogen, washed with ether (3×5 mL), and then dried under high vacuum to give (S)-3-(4-chloro-phenyl)-N1,N1-dimethyl-propane-1,2-diamine hydrochloride salt (2.1 g, 64%) as a pale yellow hygroscopic solid.

Step 3: 2-{3-[((S)-4-Chloro-phenyl)-1-dimethylaminomethyl-ethylamino)-methyl]-benzyl}-1,1-dioxo-1λ$^6$-isothiazolidine-3-carboxylic acid ethyl ester

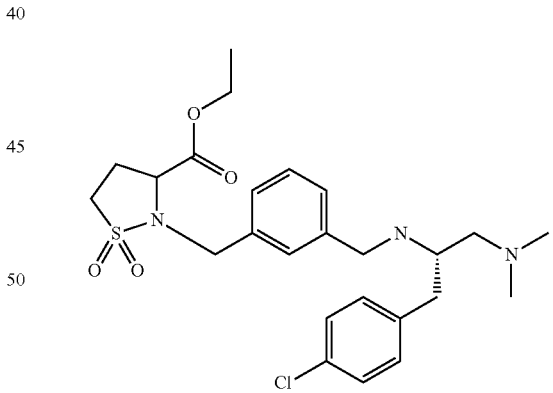

Triethylamine (214 µL, 1.5 mmol) was added to a solution of (S)-3-(4-chloro-phenyl)-N1,N1-dimethyl-propane-1,2-diamine hydrochloride salt (Intermediate X; 182 mg, 0.73 mmol) in methanol (2 mL). The mixture was stirred for 10 min and then a solution of 2-(3-formyl-benzyl)-1,1-dioxo-1λ$^6$-isothiazolidine-3-carboxylic acid ethyl ester (Intermediate 8 Step 3; 190 mg, 0.61 mmol) in methanol (4 mL) was added under argon. The mixture was stirred at room temperature for 15 min and then cooled in an ice-bath. Solid sodium cyanoborohydride (57.5 mg, 0.9 mmol) and glacial acetic acid (540 µL) were added. The reaction mixture was allowed to warm to room temperature and stir. The progress of the reaction was monitored by LCMS. When the reaction was substantially complete, the solvents were evaporated and ethyl acetate (50 mL) was added. The solution was washed with washed with water (2×10 mL) and the aqueous layer was extracted with ethyl acetate (50 mL). The combined organics were dried over sodium sulfate, filtered and concentrated to give crude 2-{3-[((S)-4-chloro-phenyl)-1-dimethylaminomethyl-ethylamino)-methyl]-benzyl}-1,1-dioxo-1λ⁶-isothiazolidine-3-carboxylic acid ethyl ester (390 mg) as a tacky yellow foam which was used directly in the next step without further purification.

Step 4: 2-{3-[((S)-4-Chloro-phenyl)-1-dimethylaminomethyl-ethylamino)-methyl]-benzyl}-1,1-dioxo-1λ⁶-isothiazolidine-3-carboxylic acid

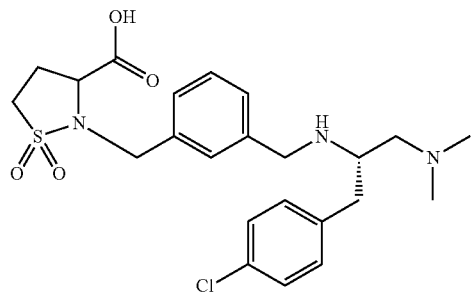

To a solution of crude 2-{3-[((S)-4-chloro-phenyl)-1-dimethylaminomethyl-ethylamino)-methyl]-benzyl}-1,1-dioxo-1λ⁶-isothiazolidine-3-carboxylic acid ethyl ester (310 mg, approx. 0.61 mmol) in tetrahydrofuran (3.6 mL) was added lithium hydroxide hydrate (51 mg, 1.2 mmol) followed by water (910 μL). The reaction mixture was stirred at room temperature for 2 h, and then the mixture was concentrated under reduced pressure to remove tetrahydrofuran. The remaining solution was stirred and approximately 25 drops of 1 M hydrochloric acid were added to bring the pH to 4.5. The sample was stirred for 10 min and the aqueous solution was decanted away from the yellow gum. The gum was washed with water (2 mL). The combined aqueous layers were evaporated to dryness, and dried overnight to give 2-{3-[((S)-4-chloro-phenyl)-1-dimethylaminomethyl-ethylamino)-methyl]-benzyl}-1,1-dioxo-1λ⁶-isothiazolidine-3-carboxylic acid as a pale yellow residue (292 mg).

Step 5: 2-{3-{[(S)-2-(4-Chloro-phenyl)-1-dimethylaminomethyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide

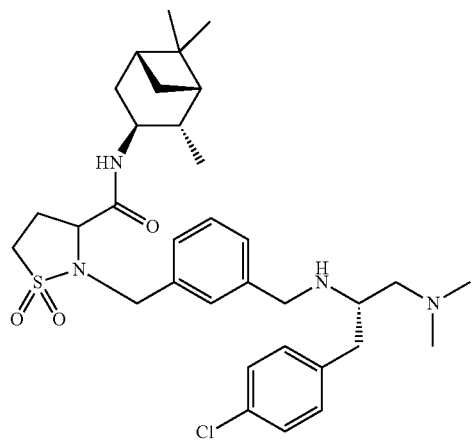

(+)-Isopinocampheylamine (Aldrich; 88 mg, 0.55 mmol), O-(benzotriazol-1-yl)-N,N,N',N'-tetramethyluronium tetrafluoroborate (available from Aldrich Chemical Company, Inc., 1001 West Saint Paul Avenue, Milwaukee, Wis. 53233, USA; 177 mg, 0.55 mmol), N-hydroxybenzotriazole (available from 3B Scientific Corporation, Libertyville, Ill. 60048, USA; 74 mg, 0.55 mmol) in dry N,N-dimethylformamide (8 mL) were added to a cooled (0° C.) solution of 2-{3-[((S)-4-chloro-phenyl)-1-dimethylaminomethyl-ethylamino)-methyl]-benzyl}-1,1-dioxo-1λ⁶-isothiazolidine-3-carboxylic acid (292 mg ~90% pure, 0.55 mmol) under argon. N,N-Diisopropylethylamine (214 μL, 1.2 mmol) was then added. The solution was then stirred at room temperature for 45 min. The reaction mixture was diluted with ethyl acetate (50 mL) and washed with 1N NaOH (3×15 mL), and brine (20 mL). The organic phase was dried over sodium sulfate, filtered and concentrated to give the crude product (370 mg) as a viscous oil. This material was purified by chromatography, eluting with 0-10% methanol/dichloromethane, to give 2-{3-{[(S)-2-(4-chloro-phenyl)-1-dimethylaminomethyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide (110 mg, 33%) as a light tan hygroscopic foam.

Step 6: 2-[3-({(6-Chloro-2-fluoro-3-methoxy-benzyl)-[(S)-2-(4-chloro-phenyl)-1-dimethylaminomethyl-ethyl]-amino}-methyl)-benzyl]-1,1-dioxo-1λ⁶-isothiazolidine-3-carboxylic acid((1S,2S,3S,5R)-2,6,6-trimethyl-bicyclo[3.1.1]hept-3-yl)-amide

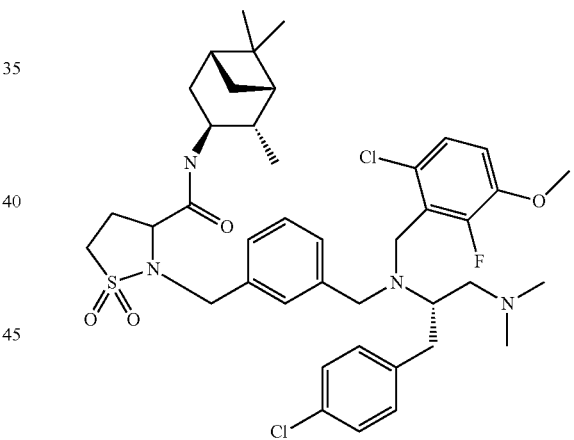

6-Chloro-2-fluoro-3-methoxy-benzaldehyde (Intermediate 4; 37 mg, 0.2 mmol) was added to a solution of 2-{3-{[(S)-2-(4-chloro-phenyl)-1-dimethylaminomethyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide (110 mg, 0.18 mmol) in methanol (3 mL) at 0° C. under argon. The mixture was stirred at 0° C. for a few minutes and then sodium cyanoborohydride (17 mg, 0.27 mmol) and glacial acetic acid (95 μL) were added. The mixture was stirred overnight at room temperature. The solution was cooled again to 0° C., and 6-chloro-2-fluoro-3-methoxy-benzaldehyde (Intermediate 4; 4 mg, 0.02 mmol) was added, followed by sodium cyanoborohydride (3 mg, 0.05 mmol) was added. The mixture was stirred for 2 h. The solution was cooled again to 0° C., and 6-chloro-2-fluoro-3-methoxy-benzaldehyde (Intermediate 4; 5 mg, 0.027 mmol) was added, followed by sodium cyanoborohydride (5 mg, 0.08 mmol)

was added. The mixture was stirred for 4 h at room temperature. The solution was cooled again to 0° C., and 6-chloro-2-fluoro-3-methoxy-benzaldehyde (Intermediate 4; 5 mg, 0.027 mmol) was added, followed by sodium cyanoborohydride (5 mg, 0.08 mmol). The mixture was stirred for 6 h at room temperature. The mixture was concentrated to remove methanol. Ethyl acetate (50 mL) was added and the mixture was washed with water (2×25 mL), and brine (25 mL). The aqueous layers were back-extracted with ethyl acetate (50 mL). The combined organic phases were dried over sodium sulfate, filtered and concentrated to give crude product. This material was purified by chromatography on an 8 gm silica column, eluting with 0-10% methanol/dichloromethane, followed by trituration with ether/pentane (1/1, 2 mL), to give 2-[3-({(6-chloro-2-fluoro-3-methoxy-benzyl)-[(S)-2-(4-chloro-phenyl)-1-dimethylaminomethyl-ethyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide as a white solid (32 mg, 25%). HRMS: calcd for $C_{41}H_{54}Cl_2FN_4O_4S$. Calc [M+H$^+$] 787.3222. found 787.3221.

Example 24

[2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-(4-phenyl-piperidin-1-yl)-methanone

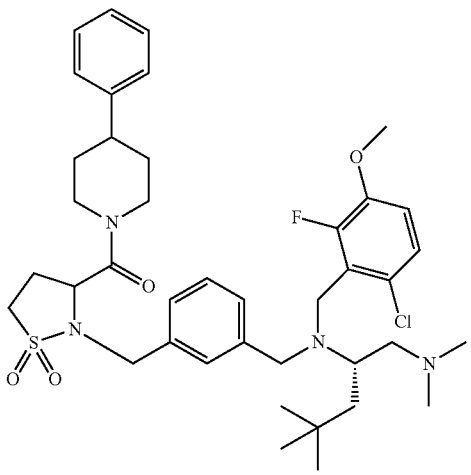

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1$\lambda^6$-isothiazolidine-3-carboxylic acid (Intermediate 7, 0.065 g, 0.108 mmol) was reacted with 4-phenylpiperidine (available from Aldrich Chemical Company, Inc., 1001 West Saint Paul Avenue, Milwaukee, Wis. 53233, USA; 0.023 g, 0.140 mmol) to form [2-(3-{[(6-chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-(4-phenyl-piperidin-1-yl)-methanone (0.018 g, 23%). m/z=741 (M+1); HRMS: calcd for $C_{40}H_{55}ClFN_4O_4S$. Calc [M+H$^+$] 741.3611. found 741.3611.

Example 25

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide (Epimer 1)

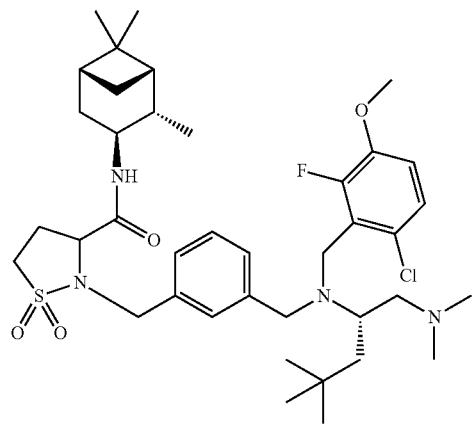

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1$\lambda^6$-isothiazolidine-3-carboxylic acid (Intermediate 7 (Epimer 1), 0.070 g, 0.117 mmol) was reacted with (1S,2S,3S,5R)-2,6,6-Trimethyl-bicyclo[3.1.1]hept-3-ylamine (available from Aldrich Chemical Company, Inc., 1001 West Saint Paul Avenue, Milwaukee, Wis. 53233, USA; 25 µL, 0.148 mmol) to form 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide (Epimer 1) (0.062 g, 72%). m/z=733 (M+1); HRMS: calcd for $C_{39}H_{59}ClFN_4O_4S$. Calc [M+H$^+$] 1733.3924. found 733.3925.

Example 26

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide (Epimer 2)

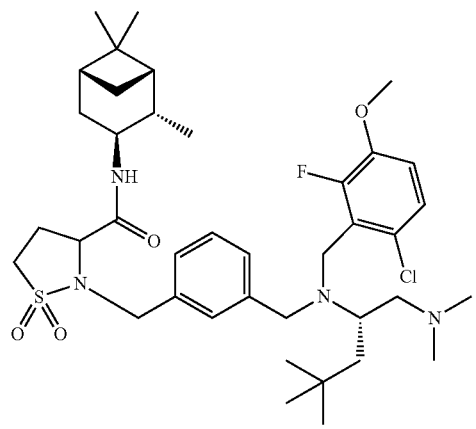

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ$^6$-isothiazolidine-3-carboxylic acid (Intermediate 7 (Epimer 2), 0.075 g, 0.125 mmol) was reacted with (1S,2S,3S,5R)-2,6,6-Trimethyl-bicyclo[3.1.1]hept-3-ylamine (available from Aldrich Chemical Company, Inc., 1001 West Saint Paul Avenue, Milwaukee, Wis. 53233, USA; 26 µL, 0.154 mmol) to form (R)-2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide (Epimer 2) (0.052 g, 57%). m/z=733 (M+1); HRMS: calcd for C$_{39}$H$_{59}$ClFN$_4$O$_4$S. Calc [M+H$^+$] 1733.3924. found 733.3925.

Example 27

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid 4-chloro-benzylamide

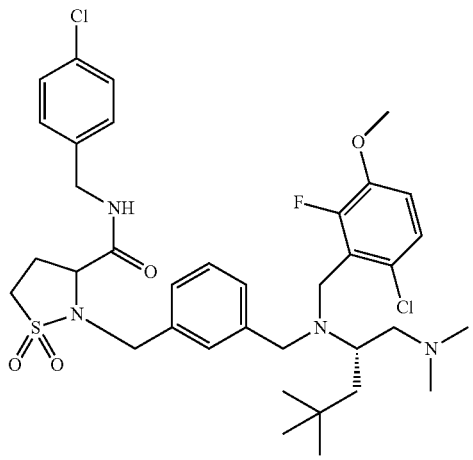

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ$^6$-isothiazolidine-3-carboxylic acid (Intermediate 7, 0.085 g, 0.142 mmol) was reacted with 4-chlorobenzyl amine (available from Aldrich Chemical Company, Inc., 1001 West Saint Paul Avenue, Milwaukee, Wis. 53233, USA; 43 µL, 0.355 mmol) to form 2-(3-{[(6-chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid 4-chloro-benzylamide (0.038 g, 37%). m/z=721 (M+1); HRMS: calcd for C$_{36}$H$_{48}$Cl$_2$FN$_4$O$_4$S. Calc [M+H$^+$] 721.2752. found 721.2755.

Example 28

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((S)-1,7,7-trimethyl-bicyclo[2.2.1]hept-2-yl)-amide

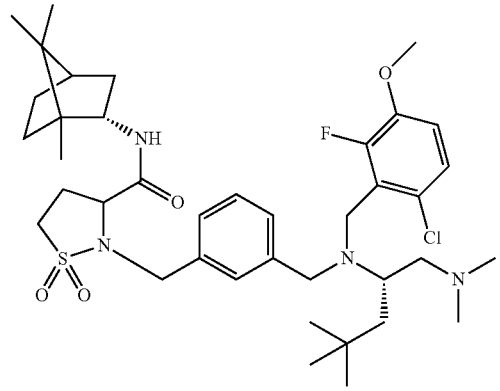

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ$^6$-isothiazolidine-3-carboxylic acid (Intermediate 7, 0.090 g, 0.150 mmol) was reacted with (R)-(+)-bornylamine (available from Aldrich Chemical Company, Inc., 1001 West Saint Paul Avenue, Milwaukee, Wis. 53233, USA; 0.034 g, 0.225 mmol) to form 2-(3-{[(6-chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid 45)-1,7,7-trimethyl-bicyclo[2.2.1]hept-2-yl)-amide (0.053 g, 49%). m/z=733 (M+1); HRMS: calcd for C$_{39}$H$_{59}$ClFN$_4$O$_4$S. Calc [M+H$^+$] 733.3924. found 733.3927.

Example 29

2-(3-{[(2,3-Difluoro-6-methoxy-benzyl)-((S)-1-dimethylaminomethyl-2-phenyl-ethyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide

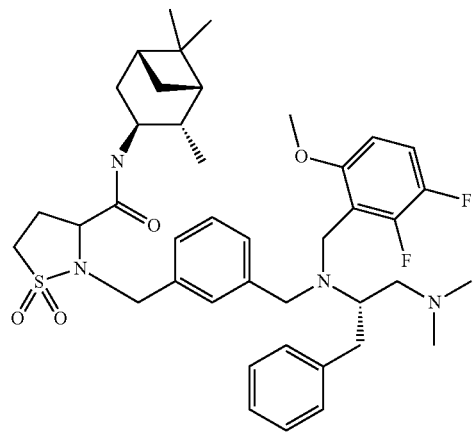

Step 1: 2,3-Difluoro-6-methoxy-benzaldehyde

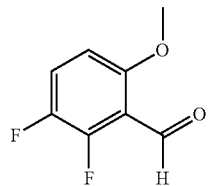

A solution of 1,2-difluoro-4-methoxy-benzene (Aldrich; 10.0 g, 69.4 mmol) in dry tetrahydrofuran (500 mL) was cooled to −78° C. under a nitrogen atmosphere. A solution of lithium diisopropylamide (available from Aldrich Chemical Company, Inc., 1001 West Saint Paul Avenue, Milwaukee, Wis. 53233, USA; 1.8 M in tetrahydrofuran/heptane/ethylbenzene, 40 mL, 72.9 mmol) was added dropwise by syringe. The reaction mixture was warmed to −55° C. and held at this temperature for 1 h. The mixture was then cooled again to −78° C., and dry N,N-dimethylformamide (10.7 mL, 139 mmol) was added by syringe. The cooling bath was removed and the reaction was allowed to warm to −10° C. and quenched by the addition of ice flakes (~200 mL) and a solution of saturated ammonium chloride (200 mL). Ethyl acetate (200 mL) was added, the layers were separated and the aqueous later was extracted with ethyl acetate (200 mL). The combined organic layers were washed with brine, dried over sodium sulfate, filtered, evaporated, and purified by silica gel chromatography, eluting with 0-30% ethyl acetate/hexanes to give 2,3-difluoro-6-methoxy-benzaldehyde (7.0 g, 59% yield) as an oil that solidified upon standing.

Step 2: 2-(3-{[(2,3-Difluoro-6-methoxy-benzyl)-((S)-1-dimethylaminomethyl-2-phenyl-ethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide

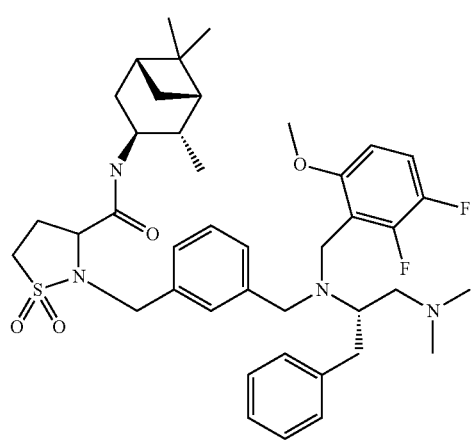

2,3-Difluoro-6-methoxy-benzaldehyde (from Step 1; 29 mg, 0.17 mmol) was added to a solution of 2-{3-[((S)-1-dimethylaminomethyl-2-phenyl-ethylamino)-methyl]-benzyl}-1,1-dioxo-1λ⁶-isothiazolidine-3-carboxylic acid((1S,2S,3S,5R)-2,6,6-trimethyl-bicylo[3.1.1]hept-3-yl)amide (Intermediate 5; 90 mg, 0.16 mmol) in methanol (3 mL) at room temperature under argon. The mixture was stirred for a few minutes and then sodium cyanoborohydride (available from Aldrich Chemical Company, Inc., 1001 West Saint Paul Avenue, Milwaukee, Wis. 53233, USA; 5 mg, 0.08 mmol) and glacial acetic acid (78 µL) were added. The mixture was stirred for 4 h at room temperature. 2,3-Difluoro-6-methoxy-benzaldehyde (from Step 1; 5 mg, 0.03 mmol) was added, followed by sodium cyanoborohydride (3 mg, 0.05 mmol) was added. The mixture was stirred for 4 h at room temperature. The mixture was stirred overnight at room temperature, and it was then concentrated under reduced pressure to remove methanol. Ethyl acetate (50 mL) was added and the mixture was washed with water (2×25 mL), and brine (25 mL). The aqueous layers were back-extracted with ethyl acetate (50 mL). The combined organic phases were dried over sodium sulfate, filtered and concentrated to give crude product. Chromatography on a 12 gm silica column, eluting with 0-10% methanol/dichloromethane, followed by trituration with ether/pentane (1/1, 2 mL) to give partially purified material. Ethyl acetate (3 mL) and saturated sodium bicarbonate solution (2 mL) were added and the mixture was stirred for 30 min. The mixture was extracted with ethyl acetate (2×25 mL) and the organic layers were washed with brine, then dried, filtered and evaporated to give 2-(3-{[(2,3-difluoro-6-methoxy-benzyl)-((S)-1-dimethylaminomethyl-2-phenyl-ethyl)-amino]-methyl}-benzyl)-1,1-dioxo-1λ⁶-isothiazolidine-3-carboxylic acid((1S,2S,3S,5R)-2,6,6-trimethyl-bicyclo[3.1.1]hept-3-yl)-amide (48 mg, 42%) as a white solid. HRMS: calcd for $C_{41}H_{55}F_2N_4O_4S$. Calc [M+H⁺] 737.3907. found 737.3906.

Example 30

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid adamantan-2-ylamide

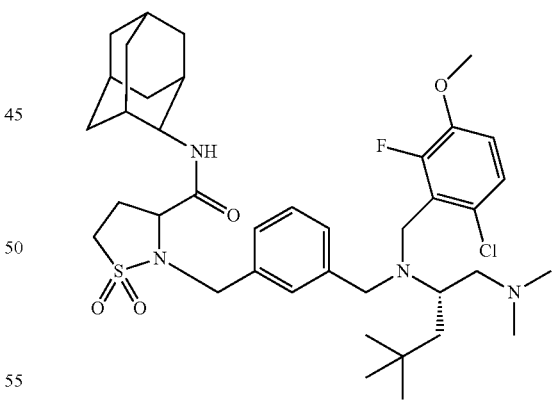

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ⁶-isothiazolidine-3-carboxylic acid (Intermediate 7, 0.093 g, 0.155 mmol) was reacted with 2-adamantanamine hydrochloride (available from Aldrich Chemical Company, Inc., 1001 West Saint Paul Avenue, Milwaukee, Wis. 53233, USA; 0.036, 0.192 mmol) to form 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ⁶-isothiazolidine-3-carboxylic acid adamantan-2-ylamide (0.075 g, 66%). m/z=731 (M+1); HRMS: calcd for $C_{39}H_{57}ClFN_4O_4S$. Calc [M+H$^+$] 731.3768. found 731.3773.

Example 31

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((1R,2R,3R,4S)-3-isopropyl-bicyclo[2.2.1]hept-2-yl)-amide and 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((1S,2S,3S,4R)-3-isopropyl-bicyclo[2.2.1]hept-2-yl)-amide

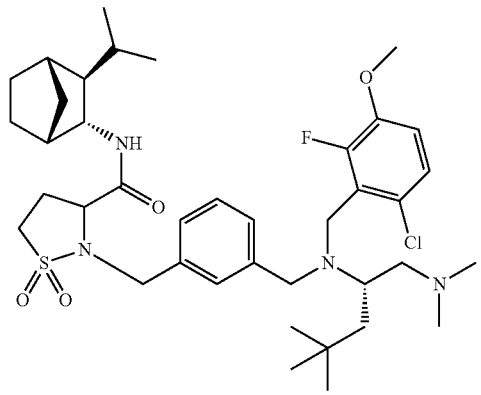

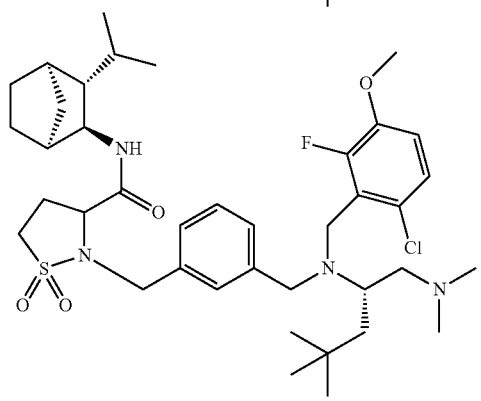

2-(3-{[(6-Chloro-2-fluoro-3-methoxy-benzyl)-((S)-1dimethylaminomethyl-3,3-dimethyl-butyl)-amino]-methyl}-benzyl)-1,1-dioxo-1λ$^6$-isothiazolidine-3-carboxylic acid (Intermediate 7, 0.085 g, 0.144 mmol) was reacted with (+/−)-2-endo-amino-3-exo-isopropylbicyclo[2.2.1]heptane (Sigma-Aldrich Corporation, St. Louis, Mo., USA; 0.041 g, 0.216 mmol) to form: 2-(3-{[(6-chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((1R,2R,3R,4S)-3-isopropyl-bicyclo[2.2.1]hept-2-yl)-amide and 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ6-isothiazolidine-3-carboxylic acid((1S,2S,3S,4R)-3-isopropyl-bicyclo[2.2.1]hept-2-yl)-amide (0.048 g, 45%) as a mixture of diastereoisomers which were not separated. m/z=733 (M+1); HRMS: calcd for $C_{39}H_{59}ClFN_4O_4S$. Calc [M+H$^+$] 733.3924. found 733.3924.

Example 32

[2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidin-3-yl]-[4-(4-chloro-phenyl)-4-hydroxy-piperidin-1-yl]-methanone

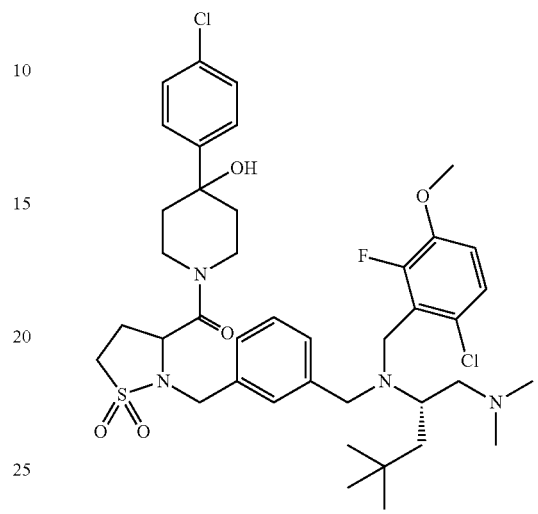

2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ$^6$-isothiazolidine-3-carboxylic acid (Intermediate 7, 0.081 g, 0.135 mmol) was reacted with 4-(4-chlorophenyl)-4-hydroxypiperidine (available from Aldrich Chemical Company, Inc., 1001 West Saint Paul Avenue, Milwaukee, Wis. 53233, USA; 0.035, 0.166 mmol) to form [2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ6-isothiazolidin-3-yl]-[4-(4-chloro-phenyl)-4-hydroxy-piperidin-1-yl]-methanone (0.066 g, 62%). m/z=791 (M+1); HRMS: calcd for $C_{40}H_{54}Cl_2FN_4O_5S$. Calc [M+H$^+$] 791.3171. found 791.3169.

Example 33

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid adamantan-1-ylamide (Epimer 1)

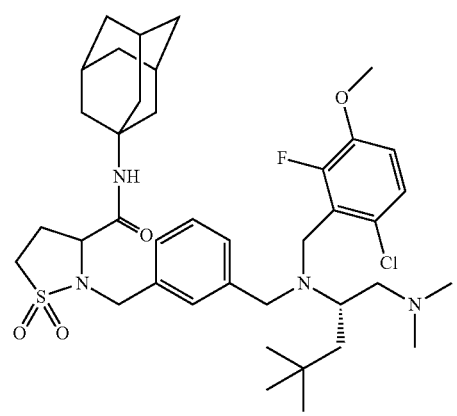

(S)-2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ$^6$-isothiazolidine-3-carboxylic acid (Intermediate 7 (Epimer 1), 0.071 g, 0.119 mmol) was reacted with 1-adamantanamine (available from Aldrich Chemical Company, Inc., 1001 West Saint Paul Avenue, Milwaukee, Wis. 53233, USA; 0.022 g, 0.144 mmol) to form (S)-2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid adamantan-1-ylamide (Epimer 1) (0.054 g, 61%). m/z=731 (M+1); HRMS: calcd for $C_{39}H_{57}ClFN_4O_4S$. Calc [M+H$^+$] 731.3768. found 731.3765.

Example 34

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid adamantan-1-ylamide (Epimer 2)

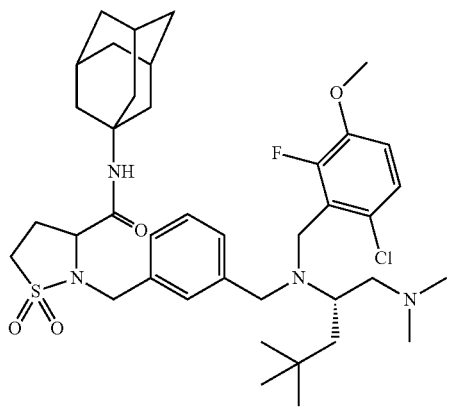

(R)-2-(3-{[(6-Chloro-2-fluoro-3-methoxy-benzyl)-((S)-1 dimethylaminomethyl-3,3-dimethyl-butyl)-amino]-methyl}-benzyl)-1,1-dioxo-1λ$^6$-isothiazolidine-3-carboxylic acid (Intermediate 7 (Epimer 2), 0.044 g, 0.073 mmol) was reacted with 1-adamantanamine (0.013 g, 0.089 mmol) to form (R)-2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid adamantan-1-ylamide (Epimer 2) (0.033 g, 61%). m/z=731 (M+1); HRMS: calcd for $C_{39}H_{57}ClFN_4O_4S$. Calc [M+H$^+$] 731.3768. found 731.3767.

Example 35

2-(3-{[(6-Chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide

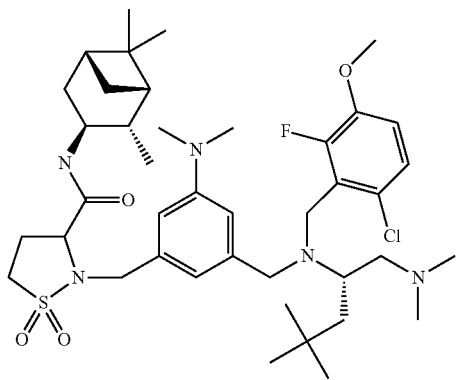

Step 1: [3-(tert-Butyl-dimethyl-silanyloxymethyl)-5-nitro-phenyl]-methanol

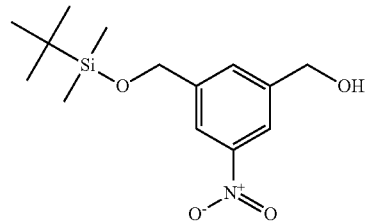

A solution of tert-butyldimethylsilyl chloride (available from Aldrich Chemical Company, Inc., 1001 West Saint Paul Avenue, Milwaukee, Wis. 53233, USA; 1.3 g, 8.6 mmol) in methylene chloride (40 mL) was added dropwise over a period of 2 hours to a magnetically stirred solution of (3-hydroxymethyl-5-nitro-phenyl)-methanol (available from Aldrich; 1.50 g, 8.19 mmol) and imidazole (0.610 g, 9.00 mmol) in methylene chloride (80 mL) at 0° C. The resulting mixture was allowed to warm up to room temperature and stirred overnight. The reaction mixture was washed with water (2×200 mL) and brine, dried over sodium sulfate, filtered, concentrated, and purified by silica gel chromatography, eluting with 10-75% ethyl acetate/hexanes to give [3-(tert-butyl-dimethyl-silanyloxymethyl)-5-nitro-phenyl]-methanol (1.20 g, 49% yield) as a viscous oil that solidified upon standing.

Step 2: [3-Amino-5-(tert-butyl-dimethyl-silanyloxymethyl)-phenyl]-methanol

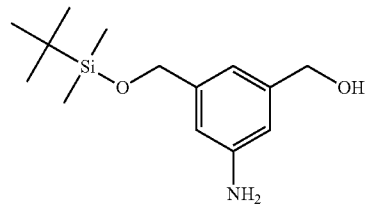

10% Palladium-on-carbon (53 mg) was added to a magnetically stirred solution of [3-(tert-butyl-dimethyl-silanyloxymethyl)-5-nitro-phenyl]-methanol (535 mg, 1.80 mmol) in ethanol (20 mL). The heterogeneous mixture was purged twice using vacuum and dry nitrogen, then stirred at room temperature under hydrogen at atmospheric pressure. After three hours, the reaction mixture was filtered through a pad of Celite®. The pad was washed with ethanol (2×20 mL) and the filtrate was concentrated to give crude [3-amino-5-(tert-butyl-dimethyl-silanyloxymethyl)-phenyl]-methanol (515 mg) as an off-white solid, which was used directly in the next step without purification.

Step 3: [3-(tert-Butyl-dimethyl-silanyloxymethyl)-5-dimethylamino-phenyl]-methanol

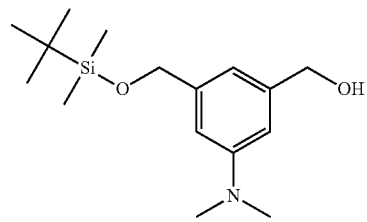

Sodium cyanoborohydride (470 mg, 7.48 mmol) was added to a magnetically stirred solution of [3-amino-5-(tert-butyl-dimethyl-silanyloxymethyl)-phenyl]-methanol (1.0 g, 3.74 mmol) in methanol (30 mL). The reaction vessel was capped with a septum and pierced with a needle. In a separate flask, parafomaldehyde (449 mg, 15.0 mmol) was heated with heat gun and the gas cannulated into the reaction vessel with a stream of nitrogen. After all the paraformaldehyde was added, a solution of zinc chloride (510 mg, 3.74 mmol) in methanol (8 mL) was added dropwise. Gas evolution was observed. After the addition was complete, TLC indicated that the starting material had been consumed. The reaction mixture was diluted with ethyl acetate (100 mL) and washed with 1% aqueous ammonium hydroxide and then with brine. The solution was dried over sodium sulfate, filtered, concentrated, and purified by silica gel chromatography, eluting with 10-60% ethyl acetate/hexanes to give [3-(tert-butyl-dimethyl-silanyloxymethyl)-5-dimethylamino-phenyl]-methanol (906 mg, 82% yield) as a viscous oil.

Step 4: 3-(tert-Butyl-dimethyl-silanyloxymethyl)-5-dimethylamino-benzaldehyde

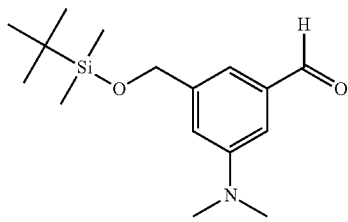

A suspension of Dess-Martin periodinane (available from Aldrich Chemical Company, Inc., 1001 West Saint Paul Avenue, Milwaukee, Wis. 53233, USA; 538 mg, 1.27 mmol) in methylene chloride (10 mL) was pipetted into a magnetically stirred solution of [3-(tert-butyl-dimethyl-silanyloxymethyl)-5-dimethylamino-phenyl]-methanol (288 mg, 0.986 mmol) in methylene chloride (20 mL). The mixture was stirred for 15 min. Powdered sodium bicarbonate (~500 mg) was added and the volatiles were removed in vacuo. The residue was purified by silica gel chromatography, eluting with 10-40% ethyl acetate/hexanes, to give 3-(tert-butyl-dimethyl-silanyloxymethyl)-5-dimethylamino-benzaldehyde (187 mg, 65%) as a yellow oil.

Step 5: 3-Bromomethyl-5-dimethylamino-benzaldehyde

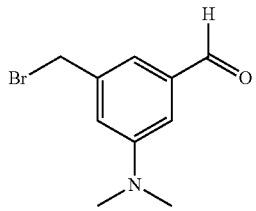

Glacial acetic acid (6 mL) and water (2 mL) were added to a magnetically stirred solution of 3-(tert-butyl-dimethyl-silanyloxymethyl)-5-dimethylamino-benzaldehyde (344 mg, 1.2 mmol) in tetrahydrofuran (2 mL). The mixture was stirred for 2 h and then additional 10 mL of glacial acetic acid was added. The reaction mixture was stirred overnight. TLC indicated a of trace starting material present and a slower moving spot. The volatiles were removed in vacuo, and glacial acetic acid (24 mL), water (8 mL), and tetrahydrofuran (8 mL) were added. The resulting mixture was warmed to 40° C. After 2.5 hours, TLC indicated complete consumption of the starting material. The volatiles were removed in vacuo and the residue was dissolved in ethyl acetate/water (100 mL 1:1 v/v). The aqueous layer was made basic using saturated aqueous sodium carbonate and the layers were separated. The aqueous layer was extracted with ethyl acetate (25 mL). The combined organic layers were dried over sodium sulfate, filtered, and concentrated in vacuo to give the intermediate alcohol (178 mg, 81%) as a pale oil. This material was dissolved in tetrahydrofuran (10 mL) and the resulting solution was added to a solution which had been prepared by adding bromine (102 µL, 1.99 mmol) dropwise by syringe under a nitrogen atmosphere to a magnetically stirred solution of triphenylphosphine (available from Aldrich Chemical Company, Inc., 1001 West Saint Paul Avenue, Milwaukee, Wis. 53233, USA; 522 mg, 1.99 mmol) in 20 mL of acetonitrile at 0° C. and stirring the solution for 10 min at 0° C. The reaction mixture was stirred at about 0° C. for 20 min, and then water (50 mL), a few crystals of sodium bisulfite, and ethyl acetate (50 mL) were added. The aqueous layer was separated and washed once with ethyl acetate (50 mL). The combined organic layers were dried over sodium sulfate, filtered, evaporated and purified by filtering through a silica gel plug, then eluting with 20% ethyl acetate/hexanes to give 3-bromomethyl-5-dimethylamino-benzaldehyde (100 mg, 35% yield over two steps).

Step 6: 2-(3-Dimethylamino-5-formyl-benzyl)-1,1-dioxo-1λ$^6$-isothiazolidine-3-carboxylic acid methyl ester and 2-(3-dimethylamino-5-formyl-benzyl)-1,1-dioxo-1λ$^6$-isothiazolidine-3-carboxylic acid ethyl ester

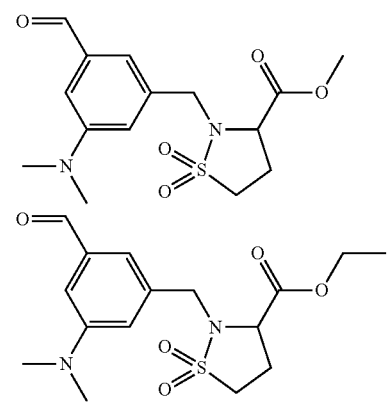

A 4:3 mixture of (S)-1,1-dioxo-1λ$^6$-isothiazolidine-3-carboxylic acid methyl ester and (S)-1,1-dioxo-1λ$^6$-isothiazolidine-3-carboxylic acid ethyl ester benzaldehyde (see Intermediate 8 Step 2; 148 mg, 0.84 mmol) and cesium carbonate (134 mg, 0.41 mmol) were added to a magnetically stirred solution of 3-bromomethyl-5-dimethylamino-benzaldehyde (100 mg, 0.413 mmol) in dry N,N-dimethylformamide (10 mL). The resulting suspension was stirred overnight. The solvent was removed in vacuo and the residue was dissolved in ethyl acetate (25 mL) and washed with water (50 mL). The aqueous layer was separated and extracted once with ethyl acetate (25 mL). The combined organic layers were dried over sodium sulfate, filtered, evaporated and purified by silica gel chromatography, eluting with 10-75% ethyl acetate/hexanes, to give a 1:1 mixture of (S)-2-(3-dimethylamino-5-formyl-benzyl)-1,1-dioxo-1λ$^6$-isothiazolidine-3-carboxylic acid methyl ester and (S)-2-(3-dimethylamino-5-formyl-benzyl)-1,1-dioxo-1λ$^6$-isothiazolidine-3-carboxylic acid ethyl ester (144 mg).

Step 7: 2-{3-Dimethylamino-5-[((S)-1-dimethylaminomethyl-3,3-dimethyl-butylamino)-methyl]-benzyl}-1,1-dioxo-1λ$^6$-isothiazolidine-3-carboxylic acid methyl ester and 2-{3-dimethylamino-5-[((S)-1-dimethylaminomethyl-3,3-dimethyl-butylamino)-methyl]-benzyl}-1,1-dioxo-1λ$^6$-isothiazolidine-3-carboxylic acid ethyl ester

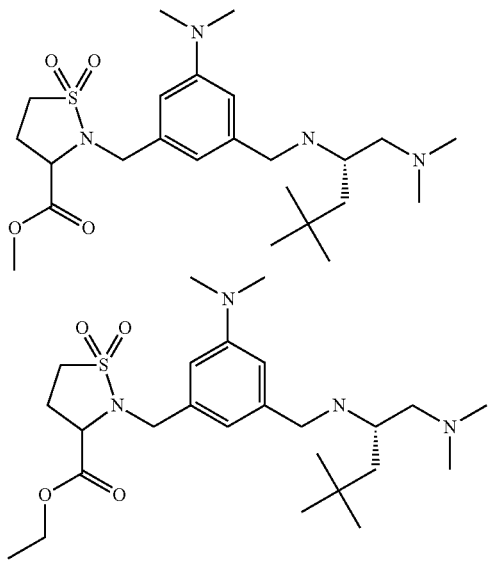

(S)-4,4,N1,N1-Tetramethyl-pentane-1,2-diamine hydrochloride salt (Intermediate 2, 0.100 g, 0.43 mmol), magnesium sulfate (100 mg) and triethylamine (118 µL, 0.847 mmol) were added to a 1:1 mixture of (S)-2-(3-dimethylamino-5-formyl-benzyl)-1,1-dioxo-1λ$^6$-isothiazolidine-3-carboxylic acid methyl ester and (S)-2-(3-dimethylamino-5-formyl-benzyl)-1,1-dioxo-1λ$^6$-isothiazolidine-3-carboxylic acid ethyl ester (144 mg) in dry dichloromethane (15 mL). The resulting turbid mixture was stirred at room temperature for 5 h. The volatiles were removed in vacuo and the residue was suspended in dry methanol (10 mL). Sodium cyanoborohydride (available from Aldrich Chemical Company, Inc., 1001 West Saint Paul Avenue, Milwaukee, Wis. 53233, USA; 53 mg, 0.85 mmol) and acetic acid (85 µL) were added and the mixture was stirred overnight. The volatiles were removed in vacuo and the residue was dissolved in ethyl acetate (50 mL). The solution was washed with saturated aqueous sodium bicarbonate, dried over sodium sulfate, filtered, and evaporated under reduced pressure to give a 1:1 mixture of 2-{3-dimethylamino-5-[((S)-1-dimethylaminomethyl-3,3-dimethyl-butylamino)-methyl]-benzyl}-1,1-dioxo-1λ$^6$-isothiazolidine-3-carboxylic acid methyl ester and 2-{3-dimethylamino-5-[((S)-1-dimethylaminomethyl-3,3-dimethyl-butylamino)-methyl]-benzyl}-1,1-dioxo-1λ$^6$-isothiazolidine-3-carboxylic acid ethyl ester (155 mg) which was used directly in the next step without further purification.

Step 8: 2-(3-{[(6-Chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid methyl ester and 2-(3-{[(6-chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid ethyl ester

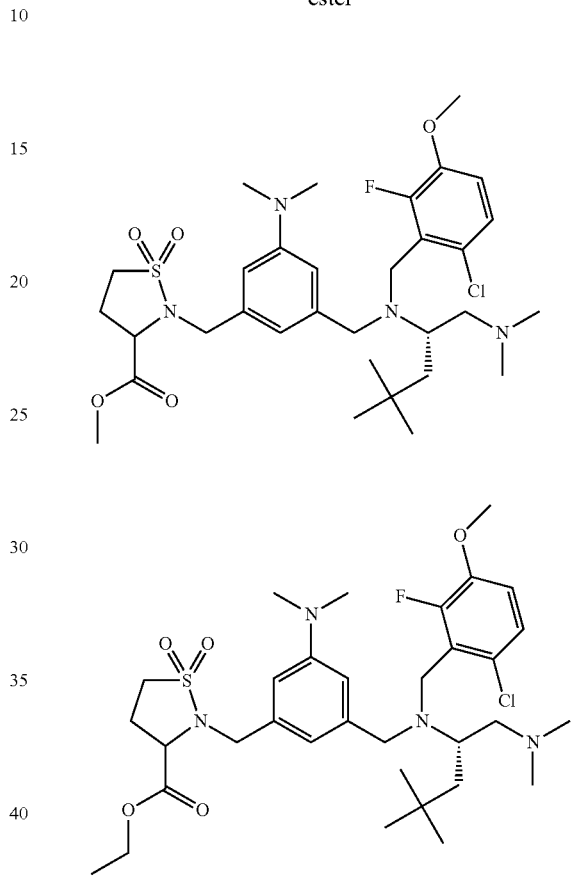

6-Chloro-2-fluoro-3-methoxy-benzaldehyde (Intermediate 4; 91 mg, 0.482 mmol) and magnesium sulfate (100 mg) were added to a magnetically stirred solution of a 1:1 mixture of 2-{3-dimethylamino-5-[((S)-1-dimethylaminomethyl-3,3-dimethyl-butylamino)-methyl]-benzyl}-1,1-dioxo-1λ$^6$-isothiazolidine-3-carboxylic acid methyl ester and 2-{3-dimethylamino-5-[((S)-1-dimethylaminomethyl-3,3-dimethyl-butylamino)-methyl]-benzyl}-1,1-dioxo-1λ$^6$-isothiazolidine-3-carboxylic acid ethyl ester (155 mg) in dry methylene chloride (15 mL). The resulting turbid mixture was stirred at room temperature for 5 h. The volatiles were removed in vacuo and the residue was suspended in dry methanol (16 mL) and treated with sodium cyanoborohydride (40 mg, 0.64 mmol) and acetic acid (128 µL). The mixture was stirred overnight. The volatiles were removed in vacuo and the residue was dissolved in ethyl acetate (50 mL). The solution was washed with saturated aqueous sodium bicarbonate, dried over sodium sulfate, filtered, and evaporated under reduced pressure to give a 1:1 mixture of 2-(3-{[(6-chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid methyl ester and of 2-(3-{[(6-chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid ethyl ester (265 mg isolated) which was used directly in the next step without further purification.

Step 9: 2-(3-{[(6-Chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ6-isothiazolidine-3-carboxylic acid((1S,2S,3S,5R)-2,6,6-trimethyl-bicyclo[3.1.1]hept-3-yl)-amide

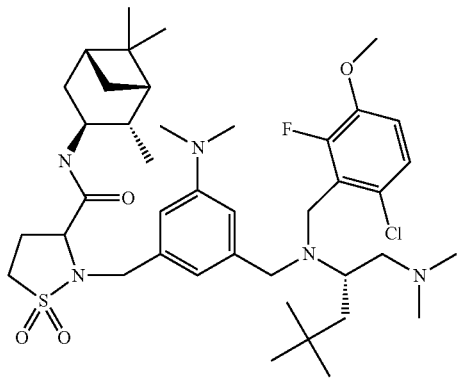

Lithium hydroxide (15 mg, 0.61 mmol) was added to a 1:1 mixture of 2-(3-{[(6-chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid methyl ester and of 2-(3-{[(6-chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid ethyl ester (265 mg) in methanol (15 mL) and water (5 mL). The reaction mixture was stirred at room temperature for 3 h and then concentrated to dryness under reduced pressure. Dry N,N-dimethylformamide (available from Aldrich Chemical Company, Inc., 1001 West Saint Paul Avenue, Milwaukee, Wis. 53233, USA; 15 mL) was added to the residue and then O-(benzotriazol-1-yl)-N,N,N',N'-tetramethyluronium hexafluorophosphate (available from Aldrich Chemical Company, Inc., 1001 West Saint Paul Avenue, Milwaukee, Wis. 53233, USA; 184 mg, 0.49 mmol), 1-hydroxybenzotriazole (available from 3B Scientific Corporation, Libertyville, Ill. 60048, USA; 74 mg, 0.49 mmol), (1S,2S,3S,5R)-(+)-isopinocampheylamine (available from Aldrich Chemical Company, Inc., 1001 West Saint Paul Avenue, Milwaukee, Wis. 53233, USA; 75 µL, 0.45 mmol) and N,N-diisopropylethylamine (available from Aldrich Chemical Company, Inc., 1001 West Saint Paul Avenue, Milwaukee, Wis. 53233, USA; 93 µL, 0.45 mmol) were added. The resulting mixture was stirred overnight. The solvent was removed in vacuo and the residue was dissolved in ethyl acetate (50 mL) and washed with water (50 mL). The aqueous layer was back-extracted with ethyl acetate (50 mL), and the combined organic layers were dried over sodium sulfate, filtered and concentrated. The crude product was purified by HPLC to give 2-(3-{[(6-chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide (300 mg, ~91% over 5 steps). HRMS: calcd for $C_{41}H_{64}ClFN_5O_4S$. Calc [M+H$^+$] 776.4346. found 776.4348.

Example 36

Testing of the Compounds of the Invention

Cytotoxicity was assessed using Promega's CellTiter-Glo® luminescent cell viability assay (Promega Corporation, Madison, Wis., USA) as described in Promega Technical Bulletin TB288, revised August 2008. The assay was performed in HeLa cells at a maximum concentration tested of 10 µM of test compound. This assay measures the amount of adenosine triphosphate (ATP) present as a way of quantifying the presence and degree of metabolic activity in cell cultures.

Viable Hela cells were plated at a density of 3000 cells/well in 96 wells in black, clear bottom plates. Cells were allowed to attach to the plate by incubating overnight at 37° C. Test compounds were diluted in DMSO then further diluted in 10% FBS media. Media was removed from the cell plates and 50 µL of the solution was added to each well manually with the exception of the control well, which contained the same volume of 10% FBS media which includes 1% DMSO. Cells were incubated in the presence of compound undisturbed for 48 hours at 37° C. After the 48 hour compound exposure, 50 µL of the pCellTiter Glo® reagent was added. The cell plates were agitated on a shaker for 2 minutes to help lyse the cells. The plate was covered and read for luminescence. The percentage inhibition of the luminescence compared to control cells was measured for each compound and is shown in the table.

Percent inhibition was calculated as follows:

$$PCT\_INHIB = 100 * [(U-T)/U]$$

Where U represents the Luminescence of wells containing untreated cells and

T represents the Luminescence of wells containing compound-treated cells

| Example | Name | Activity (PCT_INHIB @ 10 µM) |
|---|---|---|
| Example 1 | 2-(3-{[(5-Chloro-2-hydroxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid ((1S,2S,3S,5R)-2,6,6-trimethyl-bicyclo[3.1.1]hept-3-yl)-amide | 96 |
| Example 2 | 2-(3-{[((S)-1-Dimethylaminomethyl-3,3-dimethyl-butyl)-(2-iodo-benzyl)-amino]-methyl}-benzyl)-1,1-dioxo-1λ$^6$-isothiazolidine-3-carboxylic acid ((1S,2S,3S,5R)-2,6,6-trimethyl-bicyclo[3.1.1]hept-3-yl)-amide trifluoroacetate salt | 50 |
| Example 3 | 2-(3-{[((S)-1-Dimethylaminomethyl-3,3-dimethyl-butyl)-(2-ethoxy-benzyl)-amino]methyl}-benzyl)-1,1-dioxo-1λ$^6$-isothiazolidine-3-carboxylic acid ((1S,2S,3S,5R)-2,6,6-trimethyl-bicyclo[3.1.1]hept-3-yl)-amide trifluoroacetate salt | 69 |

-continued

| Example | Name | Activity (PCT_INHIB @ 10 µM) |
|---|---|---|
| Example 4 | 2-(3-{[((S)-1-Dimethylaminomethyl-3,3-dimethyl-butyl)-(5-isopropyl-2-methoxy-benzyl)-amino]-methyl}-benzyl)-1,1-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 96 |
| Example 5 | 2-(3-{[(2-Difluoromethoxy-benzyl)-((S)-1-dimethylaminomethyl-3,3-dimethyl-butyl)amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 87 |
| Example 6 | (S)-2-[3-({((S)-1-Dimethylaminomethyl-3,3-dimethyl-butyl)-[2-(4-fluoro-phenoxy)-benzyl]-amino}-methyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 82 |
| Example 7 | 2-(3-{[((S)-1-Dimethylaminomethyl-3,3-dimethyl-butyl)-(2-p-tolyloxy-benzyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 58 |
| Example 8 | 2-(3-{[((S)-1-Dimethylaminomethyl-3,3-dimethyl-butyl)-(4'-fluoro-biphenyl-2ylmethyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 97 |
| Example 9 | 2-(3-{[((S)-1-Dimethylaminomethyl-3,3-dimethyl-butyl)-(2-hydroxy-4-methylbenzyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 96 |
| Example 10 | 2-(3-{[((S)-1-Dimethylaminomethyl-3,3-dimethyl-butyl)-(2-hydroxy-5-methyl-benzyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 96 |
| Example 11 | 2-(3-{[((S)-1-Dimethylaminomethyl-3,3-dimethyl-butyl)-(2'-methyl-biphenyl-2ylmethyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 97 |
| Example 12 | 2-(3-{[((S)-1-Dimethylaminomethyl-3,3-dimethyl-butyl)-(2-fluoro-6-phenoxy-benzyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 96 |
| Example 13 | 2-(3-{[((S)-1-Dimethylaminomethyl-3,3-dimethyl-butyl)-(2,3,6-trifluoro-benzyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 93 |
| Example 14 | 2-(3-{[(6-Bromo-2-hydroxy-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 75 |
| Example 15 | 2-(3-{[(6-Chloro-2-fluoro-3-methyl-benzyl)-((S)-1-dimethylaminomethyl-3,3-dimethylbutyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 91 |
| Example 16 | 2-(3-{[[2-(4-Cyano-phenoxy)-benzyl]-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 97 |
| Example 17 | 2-(3-{[Benzo[1,3]dioxol-4-ylmethyl-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 96 |
| Example 18 | 2-(3-{[(3-Bromo-2,6-difluoro-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt | 94 |
| Example 19 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1R,2R,3R,5S)-2,6,6-trimethyl-bicyclo[3.1.1]hept-3-yl)-amide | 73 |
| Example 20 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-1-ylamide | 95 |
| Example 21 | 2-(3-{[(6-Chloro-2-fluoro-3-methoxy-benzyl)-((S)-1-dimethylaminomethyl-2-phenyl-ethyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide | 77 |
| Example 22 | 2-[3-({(6-Chloro-2-fluoro-3-methoxy-benzyl)-[(S)-2-(3-chloro-phenyl)-1-dimethylaminomethyl-ethyl]-amino}-methyl)-benzyl]-1,1-dioxo-1$\lambda^6$-isothiazolidine-3-carboxylic acid ((1S,2S,3S,5R)-2,6,6-trimethyl-bicyclo[3.1.1]hept-3-yl)-amide | 93 |
| Example 23 | 2-[3-({(6-Chloro-2-fluoro-3-methoxy-benzyl)-[(S)-2-(4-chloro-phenyl)-1-dimethylaminomethyl-ethyl]-amino}-methyl)-benzyl]-1,1-dioxo-1$\lambda^6$-isothiazolidine-3-carboxylic acid ((1S,2S,3S,5R)-2,6,6-trimethyl-bicyclo[3.1.1]hept-3-yl)-amide | 96 |
| Example 24 | [2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-(4-phenyl-piperidin-1-yl)-methanone | 96 |

-continued

| Example | Name | Activity (PCT_INHIB @ 10 µM) |
|---|---|---|
| Example 25 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide (Epimer 1) | 96 |
| Example 26 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide (Epimer 2) | 97 |
| Example 27 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid 4-chloro-benzylamide | 95 |
| Example 28 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((S)-1,7,7-trimethyl-bicyclo[2.2.1]hept-2-yl)-amide | 96 |
| Example 29 | 2-(3-{[(2,3-Difluoro-6-methoxy-benzyl)-((S)-1-dimethylaminomethyl-2-phenyl-ethyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide | 95 |
| Example 30 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-2-ylamide | 96 |
| Example 31 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1R,2R,3R,4S)-3-isopropyl-bicyclo[2.2.1]hept-2-yl)-amide | 97 |
| Example 32 | [2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-[4-(4-chloro-phenyl)-4-hydroxy-piperidin-1-yl]-methanone | 96 |
| Example 33 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-1-ylamide (Epimer 1) | 96 |
| Example 34 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-1-ylamide (Epimer 2) | 97 |
| Example 35 | 2-(3-{[(6-Chloro-2-fluoro-3-methoxy-benzyl)-((S)-1-dimethylaminomethyl-3,3-dimethyl-butyl)-amino]-methyl}-5-dimethylamino-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide hydrochloride salt | 86 |

Example 37

MTT Tetrazolium Dye Proliferation Assay

Proliferation was evaluated in an adherent cell line by the tetrazolium dye assay according to the procedure of Denizot and Lang (F. Denizot and R. Lang *J. Immunol. Methods* 1986, 89, 271-277). The cell line used was H196, a small cell lung cancer cell line obtained from the ATCC (ATCC Number CRL-5823™). The cells were grown in RPMI 1640 medium supplemented with 2.5% fetal bovine serum.

Cells were seeded into clear 96 well tissue culture treated plates at 20,000 cells per well. Plates were incubated overnight at 37° C. in a humidified incubator with 5% $CO_2$. The next day, test compounds were serially diluted to three times the final concentration in the appropriate growth medium. 50 µL of a 3× dilution of drug was added per well for a final volume of 150 uL/well. Six concentrations were tested for each compound ranging from 10 µM to 30 nM. Control wells (containing no inhibitor) had a final DMSO concentration of 0.25%. 50 µL of 0.75% DMSO in growth media was added per well for a final volume of 150 uL/well. The plates were returned to the incubator and, after 5 days, the plates were analyzed as follows: 3-(4,5-dimethylthiazol-2-yl)-2,5-diphenyl-2H-tetrazolium bromide (thiazolyl blue; MTT; Sigma) was added to each well to yield a final concentration of 1.25 mg/mL. Plates were returned to the incubator for 3 hours. The MTT-containing medium was removed and the resulting formazan metabolite was solubilized in 100% ethanol while shaking for 10 minutes at room temperature. Absorbances were read in a plate reader at a wavelength of 570 nm with a 660 nm reference. The concentrations of compounds leading to 50% and 90% inhibition of cell proliferation were determined by using the curve-fitting functionality of Microsoft Excel from plots of the logarithm of the concentration versus percent inhibition. These concentrations represent the $IC_{50}$ and $IC_{90}$ values, respectively.

| Example | Name | IC50 (µM) | IC90 (µM) |
|---|---|---|---|
| Example 25 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide (Epimer 1) | 1.4 | 1.9 |
| Example 26 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide (Epimer 2) | 1.3 | 1.8 |

Example 38

MTS Tetrazolium Assay

Proliferation was evaluated in a non-adherent cell line using the MTS tetrazolium dye assay according to the procedure of Malich and colleagues (G. Malich et al. *Toxicology* 1997, 124, 179-192). The cell line used was H146 (ATCC Number HTB-173™). The cells were grown in RPMI 1640 medium supplemented with 2.5% fetal bovine serum.

Cells were seeded into clear 96 well tissue culture treated plates at 20,000 cells per well. Plates were incubated overnight at 37° C. in a humidified incubator with 5% $CO_2$. The next day, test compounds were serially diluted to three times the final concentration in the appropriate growth medium. 50 µL of a 3× dilution of drug was added per well for a final volume of 150 uL/well. Control wells (containing no inhibitor) had a final DMSO concentration of 0.25%. 50 µL of 0.75% DMSO in growth media was added per well for a final volume of 150 uL/well. The plates were returned to the incubator. After 5 days CellTiter 96® AQ$_{ueous}$ One Solution (Promega Corporation, Madison, Wis., USA) (25 μL/well) was added to each well and the plates were placed back in the incubator for 2-3 h. The absorbance at 490 nm was measured for each well using a plate reader. The concentrations of compounds leading to 50% and 90% inhibition of cell proliferation were determined by using the curve-fitting functionality of Microsoft Excel from plots of the logarithm of the concentration versus percent inhibition. These concentrations represent the IC$_{50}$ and IC$_{90}$ values, respectively.

| Example | Name | IC50 (μM) | IC90 (μM) |
|---|---|---|---|
| Example 25 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid ((1S,2S,3S,5R)-2,6,6-trimethyl-bicyclo[3.1.1]hept-3-yl)-amide (Epimer 1) | 1.6 | 3.1 |
| Example 26 | 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid ((1S,2S,3S,5R)-2,6,6-trimethyl-bicyclo[3.1.1]hept-3-yl)-amide (Epimer 2) | 0.7 | 1.2 |

The invention claimed is:

1. A compound according to formula 1,

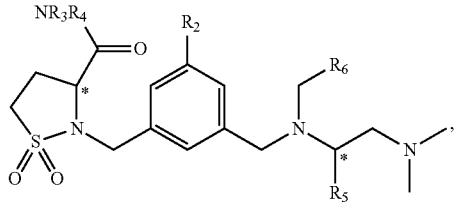

Formula 1 wherein the compound exhibits cytotoxic activity and:
$R_2$ is hydrogen or dimethylamino;
$R_3$ is hydrogen;
$R_4$ is cycloalkyl optionally substituted with alkyl, or benzyl optionally substituted with halogen;
or $R_3$ and $R_4$, together with the nitrogen atom to which they are attached, form piperidinyl substituted with one or more substituents independently selected from the group consisting of: hydroxyl and phenyl optionally substituted with halogen;
$R_5$ is alkyl or benzyl optionally substituted with halogen; and
$R_6$ is benzodioxolyl or phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen;
or a pharmaceutically-acceptable salt thereof.

2. A compound according to claim 1 wherein $R_2$ is hydrogen.

3. A compound according to claim 1 wherein $R_2$ is dimethylamino.

4. A compound according to claim 1 wherein $R_2$ is alkoxy.

5. A compound according to claim 1 wherein $R_3$ is hydrogen.

6. A compound according to claim 1 wherein $R_4$ is cycloalkyl optionally substituted with alkyl.

7. A compound according to claim 1 wherein $R_4$ is benzyl optionally substituted with halogen.

8. A compound according to claim 1 wherein $R_3$ and $R_4$, together with the nitrogen atom to which they are attached, form piperidinyl substituted with one or more substituents independently selected from the group consisting of: hydroxyl and phenyl optionally substituted with halogen.

9. A compound according to claim 1 wherein $R_5$ is benzyl optionally substituted with halogen.

10. A compound according to claim 1 wherein $R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

11. A compound according to claim 1 wherein $R_4$ is bicycloheptyl substituted three times with methyl.

12. A compound according to claim 1 wherein $R_4$ is adamantanyl.

13. A compound according to claim 1 wherein $R_4$ is bicyclo[3.1.1]hept-3-yl.

14. A compound according to claim 1 wherein $R_5$ is 2,2-dimethylpropyl.

15. A compound according to claim 1 wherein:
$R_2$ is hydrogen;
$R_3$ is hydrogen;
$R_4$ is 2,6,6-trimethyl-bicyclo[3.1.1]hept-3-yl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

16. A compound according to claim 15 selected from the group consisting of:
2-(3-{[(5-Chloro-2-hydroxy-benzyl)-((S)-1-dimethylaminomethyl-3,3-dimethyl-butyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide;
2-(3-{[((S)-1-Dimethylaminomethyl-3,3-dimethyl-butyl)-(2-iodo-benzyl)-amino]-methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt;
2-(3-{[((S)-1-Dimethylaminomethyl-3,3-dimethyl-butyl)-(2-ethoxy-benzyl)-amino]methyl}-benzyl)-1,1-dioxo-1λ$^6$-isothiazolidine-3-carboxylic acid((1S,2S,3S,5R)-2,6,6-trimethyl-bicyclo[3.1.1]hept-3-yl)-amide trifluoroacetate salt;
2-(3-{[((S)-1-Dimethylaminomethyl-3,3-dimethyl-butyl)-(5-isopropyl-2-methoxy-benzyl)-amino]-methyl}-benzyl)-1,1-1λ$^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(2-Difluoromethoxy-benzyl)-((S)-1-dimethylaminomethyl-3,3-dimethyl-butyl)amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt;

2-[3-({((S)-1-Dimethylaminomethyl-3,3-dimethyl-butyl)-[2-(4-fluoro-phenoxy)-benzyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-p-tolyloxy-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(4'-fluoro-biphenyl-2 ylmethyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-hydroxy-4-methylbenzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-hydroxy-5-methyl-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(S)-1-Dimethylaminomethyl-3,3-dimethyl-butyl)-(2'-methyl-biphenyl-2 ylmethyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2-fluoro-6-phenoxy-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[((S)-1-Dimethylaminomethyl-3,3-dimethyl-butyl)-(2,3,6-trifluoro-benzyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(6-Bromo-2-hydroxy-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(6-Chloro-2-fluoro-3-methyl-benzyl)-((S)-1-dimethylaminomethyl-3,3-dimethyl butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[[2-(4-Cyano-phenoxy)-benzyl]-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(3-Bromo-2,6-difluoro-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide trifluoroacetate salt;

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1R,2R,3R,5S)-2,6,6-trimethyl-bicyclo[3.1.1]hept-3-yl)-amide; and 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide.

17. A compound according to claim 1 wherein:
$R_2$ is hydrogen;
$R_3$ is hydrogen;
$R_4$ is adamantanyl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

18. A compound according to claim 17 selected from the group consisting of:
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-1-ylamide;

2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-2-ylamide; and 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid adamantan-1-ylamide.

19. A compound according to claim 1 wherein:
$R_2$ is hydrogen;
$R_3$ is hydrogen;
$R_4$ is 2,6,6-trimethyl-bicyclo[3.1.1]hept-3-yl;
$R_5$ is 2,2-dimethylpropyl; and
$R_6$ is benzodioxolyl.

20. A compound according to claim 1 wherein:
$R_2$ is hydrogen;
$R_3$ is hydrogen;
$R_4$ is 2,6,6-trimethyl-bicyclo[3.1.1]hept-3-yl;
$R_5$ is benzyl optionally substituted with halogen; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

21. A compound according to claim 20 selected from the group consisting of:
2-(3-{[(6-Chloro-2-fluoro-3-methoxy-benzyl)-((S)-1-dimethylaminomethyl-2-phenyl-ethyl)-amino]-methyl}-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide;

2-[3-({(6-Chloro-2-fluoro-3-methoxy-benzyl)-[(S)-2-(3-chloro-phenyl)-1-dimethylaminomethyl-ethyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide;

2-[3-({(6-Chloro-2-fluoro-3-methoxy-benzyl)-[(S)-2-(4-chloro-phenyl)-1-dimethylaminomethyl-ethyl]-amino}-methyl)-benzyl]-1,1-dioxo-1$\lambda^6$-isothiazolidine-3-carboxylic acid((1S,2S,3S,5R)-2,6,6-trimethyl-bicyclo[3.1.1]hept-3-yl)-amide; and 2-(3-{[(2,3-Difluoro-6-methoxy-benzyl)-((S)-1-dimethylaminomethyl-2-phenyl-ethyl)-amino]-methyl}-benzyl)-1,1-dioxo-1$\lambda^6$-isothiazolidine-3-carboxylic acid ((1S,2S,3S,5R)-2,6,6-trimethyl-bicyclo[3.1.1]hept-3-yl)-amide.

22. A compound according to claim 1 wherein:
$R_2$ is hydrogen;
$R_3$ and $R_4$, together with the nitrogen atom to which they are attached, form piperidinyl substituted with one or more substituents independently selected from the group consisting of: hydroxyl and phenyl optionally substituted with halogen;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

23. A compound according to claim 22 wherein said compound is:
[2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-(4-phenyl-piperidin-1-yl)-methanone; or
[2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidin-3-yl]-[4-(4-chloro-phenyl)-4-hydroxy-piperidin-1-yl]-methanone.

24. A compound according to claim 1 wherein:
$R_2$ is hydrogen;
$R_3$ is hydrogen;
$R_4$ is benzyl optionally substituted with halogen;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

25. A compound according to claim 24 wherein said compound is 2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid 4-chloro-benzylamide.

26. A compound according to claim 1 wherein:
$R_2$ is hydrogen;
$R_3$ is hydrogen;
$R_4$ is bicyclo[2.2.1]hept-3-yl optionally substituted with lower alkyl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

27. A compound according to claim 26 wherein said compound is:
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((S)-1,7,7-trimethyl-bicyclo[2.2.1]hept-2-yl)-amide;
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1R,2R,3R,4S)-3-isopropyl-bicyclo[2.2.1]hept-2-yl)-amide; or
2-(3-{[(6-Chloro-2-fluoro-3-methoxy-benzyl)-((S)-1-dimethylaminomethyl-3,3-dimethyl-butyl)-amino]-methyl}-benzyl)-1,1-dioxo-1$\lambda^6$-isothiazolidine-3-carboxylic acid((1S,2S,3S,4R)-3-isopropyl-bicyclo[2.2.1]hept-2-yl)-amide.

28. A compound according to claim 1 wherein:
$R_2$ is dimethylamino;
$R_3$ is hydrogen;
$R_4$ is 2,6,6-trimethyl-bicyclo[3.1.1]hept-3-yl;
$R_5$ is 2,2-dimethylpropyl; and
$R_6$ is phenyl optionally substituted with one to three substituents independently selected from the group consisting of: halogen, hydroxyl, alkoxy optionally substituted with halogen, alkyl, phenoxy optionally substituted with halogen, cyano, or alkyl, and phenyl optionally substituted with alkyl or halogen.

29. A compound according to claim 28 wherein said compound is 2-(3-{[(6-Chloro-2-fluoro-3-methoxy-benzyl)-((S)-1-dimethylaminomethyl-3,3-dimethyl-butyl)-amino]-methyl}5-dimethylamino-benzyl)-1,1-dioxo-1$\lambda^6$-isothiazolidine-3-carboxylic acid((1S,2S,3S,5R)-2,6,6-trimethyl-bicyclo[3.1.1]hept-3-yl)-amide hydrochloride salt.

30. A compound according to claim 1 wherein the compound exhibits a "percentage of inhibition" of luminescence of at least about 75%.

31. A compound according to claim 1 wherein the compound exhibits a "percentage of inhibition" of luminescence of at least about 95%.

32. A compound according to claim 1 wherein:
$R_2$ is hydrogen or dimethylamino;
$R_3$ is hydrogen;
$R_4$ is a bicyclic or tricyclic cycloalkyl with 7 to 10 ring atoms which optionally substituted with lower alkyl or 4-chlorobenzyl;
or $R_3$ and $R_4$, together with the nitrogen atom to which they are attached, form 4-phenyl-piperidine or 4-(4-chloro-phenyl)-4-hydroxy-piperidine;
$R_5$ is selected from the group consisting of: 2,2-dimethylpropyl; benzyl; 3-chlorobenzyl; and 4-chlorobenzyl;
$R_6$ is

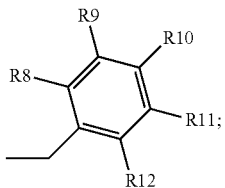

$R_8$ is selected from the group consisting of: bromo; cyanophenoxy; difluoromethoxy; ethoxy; fluoro; hydroxyl; iodo; methoxy; phenyl optionally substituted by one substituent which is halogen or lower alkyl; and phenoxy optionally substituted by one substituent which is selected from the group consisting of halogen, cyano, and lower alkyl;
$R_9$ is selected from the group consisting of hydrogen; methoxy; methyl; fluoro; and bromo;
or $R_8$ and $R_9$, taken together are —O—$CH_2$—O—;
$R_{10}$ is hydrogen or methyl;
$R_{11}$ is selected from the group consisting of: chloro; fluoro; hydrogen; isopropyl; and methyl;
$R_{12}$ is selected from the group consisting of: chloro; fluoro; hydrogen; hydroxyl; methoxy; and phenoxy.

33. A compound according to claim 32 wherein:
$R_2$ is hydrogen;
$R_9$ is selected from the group consisting of hydrogen; methoxy; and bromo;
or $R_8$ and $R_9$, taken together are —O—$CH_2$—O—; and
$R_{12}$ is selected from the group consisting of: chloro; fluoro; hydrogen; and hydroxyl.

34. A compound according to claim 32 wherein:
$R_8$ is selected from the group consisting of: bromo; difluoromethoxy; ethoxy; fluoro; iodo; phenyl substituted by one substituent which is halogen or lower alkyl; and phenoxy optionally substituted by one substituent which is selected from the group consisting of halogen, cyano, and lower alkyl;
or $R_8$ and $R_9$, taken together are —O—$CH_2$—O—;
$R_{10}$ is hydrogen; and
$R_{11}$ is hydrogen.

35. A compound according to claim 32 wherein $R_6$ is selected from the group consisting of:
2-bromo-6-hydroxy-3-methoxyphenyl;
6-chloro-2-fluoro-3-methoxyphenyl;
6-chloro-2-fluoro-3-methylphenyl;
5-chloro-2-hydroxyphenyl;
2-(4-cyanophenoxy)-phenyl;
2,6-difluoro-3-bromophenyl;
2,3-difluoro-6-methoxyphenyl;
2-difluoromethoxyphenyl;
2-ethoxyphenyl;
4'-fluoro-biphenyl-2-yl;
2-fluoro-6-phenoxyphenyl;
2-(4-fluorophenoxy)-phenyl;
2-hydroxy-4-methylphenyl;
2-hydroxy-5-methylphenyl;
2-iodophenyl;
5-isopropyl-2-methoxyphenyl;
2'-methyl-biphenyl-2-yl;
2,3-methylenedioxyphenyl;
2-(4-methylphenoxy)-phenyl; and
2,3,6-trifluorophenyl.

36. A composition comprising a therapeutically-acceptable amount of a compound according to claim 1 and a carrier.

37. A unit dose formulation comprising a therapeutically-acceptable amount of a compound according to claim 1 and a carrier.

* * * * *